US011648304B2

(12) United States Patent
Livengood et al.

(10) Patent No.: US 11,648,304 B2
(45) Date of Patent: May 16, 2023

(54) ZIKA VACCINES AND IMMUNOGENIC COMPOSITIONS, AND METHODS OF USING THE SAME

(71) Applicants: TAKEDA VACCINES, INC., Cambridge, MA (US); THE UNITED STATES OF AMERICA, AS REPRESENTED BY THE SECRETARY, DEPARTMENT OF HEALTH AND HUMAN SERVICES, Rockville, MD (US)

(72) Inventors: Jill A. Livengood, Cambridge, MA (US); Holli Giebler, Cambridge, MA (US); Whitney Baldwin, Cambridge, MA (US); Hansi Dean, Cambridge, MA (US); Claire Y. H. Kinney, Atlanta, GA (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 16/761,368

(22) PCT Filed: Nov. 5, 2018

(86) PCT No.: PCT/US2018/059219
§ 371 (c)(1),
(2) Date: May 4, 2020

(87) PCT Pub. No.: WO2019/090228
PCT Pub. Date: May 9, 2019

(65) Prior Publication Data
US 2020/0360505 A1  Nov. 19, 2020

Related U.S. Application Data

(60) Provisional application No. 62/592,995, filed on Nov. 30, 2017, provisional application No. 62/581,500, filed on Nov. 3, 2017.

(51) Int. Cl.
A61K 39/12 (2006.01)
A61P 31/14 (2006.01)
(Continued)

(52) U.S. Cl.
CPC ............ *A61K 39/12* (2013.01); *A61K 9/0019* (2013.01); *A61K 39/39* (2013.01); *A61P 31/14* (2018.01);
(Continued)

(58) Field of Classification Search
None
See application file for complete search history.

(56) References Cited

U.S. PATENT DOCUMENTS 11,219,681 B2   1/2022  Barbero Calzado et al.
2007/0110759 A1  5/2007  Sattentau et al.
(Continued)

FOREIGN PATENT DOCUMENTS

BR   102017024030 A2   6/2019
CN       105749268 A   7/2016
(Continued)

OTHER PUBLICATIONS

Haddow et al. (PLoS Neglected Tropical Diseases. 2012; 6 (2): e1477).*
(Continued)

*Primary Examiner* — Shanon A. Foley
(74) *Attorney, Agent, or Firm* — Honigman LLP; Harold H. Fox; Jonathan P. O'Brien

(57) ABSTRACT

The present disclosure relates to Zika virus vaccines and immunogenic compositions having one or more antigens from a Zika virus (e.g., a Zika virus clonal isolate, a
(Continued)

non-human cell adapted Zika virus, etc.), and methods of manufacture, formulation, testing, and uses thereof.

11 Claims, 29 Drawing Sheets
Specification includes a Sequence Listing.

(51) Int. Cl.
    *C12N 7/00*     (2006.01)
    *A61K 9/00*     (2006.01)
    *A61K 39/39*     (2006.01)
    *A61K 39/00*     (2006.01)

(52) U.S. Cl.
    CPC ........ *C12N 7/00* (2013.01); *A61K 2039/5252* (2013.01); *A61K 2039/54* (2013.01); *A61K 2039/545* (2013.01); *A61K 2039/55505* (2013.01); *C12N 2770/24034* (2013.01); *C12N 2770/24071* (2013.01); *C12N 2770/24134* (2013.01); *C12N 2770/24151* (2013.01); *C12N 2770/24163* (2013.01); *C12N 2770/24164* (2013.01)

(56) References Cited

U.S. PATENT DOCUMENTS

| | | | |
|---|---|---|---|
| 2010/0310656 | A1 | 12/2010 | Bourinbaiar et al. |
| 2013/0280295 | A1 | 10/2013 | Schlegl et al. |
| 2017/0014502 | A1* | 1/2017 | Sumathy ............... A61K 39/12 |
| 2020/0360505 | A1* | 11/2020 | Livengood ............ A61K 39/39 |
| 2021/0106669 | A1 | 4/2021 | Livengood et al. |
| 2021/0177958 | A1 | 6/2021 | Livengood et al. |
| 2021/0177959 | A1 | 6/2021 | Livengood et al. |
| 2021/0403879 | A1 | 12/2021 | Livengood et al. |

FOREIGN PATENT DOCUMENTS

| | | |
|---|---|---|
| CN | 107537029 A | 1/2018 |
| CN | 108187036 A | 6/2018 |
| CN | 108210921 A | 6/2018 |
| CN | 108503696 A | 9/2018 |
| CN | 108503697 A | 9/2018 |
| EP | 0864646 A2 | 9/1998 |
| EP | 1 724 338 A1 | 11/2006 |
| EP | 15202585.4 A1 | 6/2017 |
| EP | 16161068.8 | 6/2017 |
| EP | 16176025.1 | 6/2017 |
| EP | 16176049.1 | 6/2017 |
| EP | 16182845.4 | 6/2017 |
| JP | 2020/524598 A | 8/2020 |
| WO | WO 99/11762 A1 | 3/1999 |
| WO | WO 2007/007344 A1 | 1/2007 |
| WO | WO 2008/026225 A2 | 3/2008 |
| WO | 2010111687 A2 | 9/2010 |
| WO | 2012/160199 A1 | 11/2012 |
| WO | WO 2012/172574 A1 | 12/2012 |
| WO | WO 2013/083726 A1 | 6/2013 |
| WO | WO 2015/059714 A1 | 4/2015 |
| WO | 2016044023 A1 | 3/2016 |
| WO | WO 2016/063291 A1 | 4/2016 |
| WO | WO 2016/145149 A1 | 9/2016 |
| WO | 2016/209805 | 12/2016 |
| WO | 2017009873 A1 | 1/2017 |
| WO | 2017015463 A2 | 1/2017 |
| WO | WO 2017/009873 A1 | 1/2017 |
| WO | 2017056094 A1 | 4/2017 |
| WO | 2017070624 A1 | 4/2017 |
| WO | 2017109211 A1 | 6/2017 |
| WO | WO 2017/109223 * | 6/2017 |
| WO | WO 2017/109223 A1 | 6/2017 |
| WO | WO 2017/109224 A1 | 6/2017 |
| WO | WO 2017/109225 A1 | 6/2017 |
| WO | WO 2017/109227 A1 | 6/2017 |
| WO | WO 2017/109228 A1 | 6/2017 |
| WO | 2017132210 A1 | 8/2017 |
| WO | 2017140905 A1 | 8/2017 |
| WO | 2017147458 A1 | 8/2017 |
| WO | 2017/161151 | 9/2017 |
| WO | 2017/192856 A1 | 11/2017 |
| WO | 2017197034 A1 | 11/2017 |
| WO | 2017197035 A1 | 11/2017 |
| WO | 2017208191 A1 | 12/2017 |
| WO | 2017212291 A1 | 12/2017 |
| WO | 2017214596 A1 | 12/2017 |
| WO | WO 2017/210215 A1 | 12/2017 |
| WO | 2018007575 A1 | 1/2018 |
| WO | 2018020271 A1 | 2/2018 |
| WO | 2018022786 A1 | 2/2018 |
| WO | 2018091540 A1 | 5/2018 |
| WO | 2018115509 A2 | 6/2018 |
| WO | 2018165373 A1 | 9/2018 |
| WO | 2018187799 A1 | 10/2018 |
| WO | 2018/237039 | 12/2018 |
| WO | 2019068877 A1 | 4/2019 |
| WO | 2019/090233 A2 | 5/2019 |
| WO | 2019090238 A1 | 5/2019 |
| WO | 2019104157 A1 | 5/2019 |
| WO | 2019108970 A1 | 6/2019 |
| WO | 2019108976 A1 | 6/2019 |
| WO | 2019162465 A1 | 8/2019 |
| WO | 2019172982 A1 | 9/2019 |
| WO | 2019186199 A1 | 10/2019 |
| WO | 2019209079 A1 | 10/2019 |
| WO | 2020017765 A1 | 1/2020 |
| WO | WO 2020/226831 A1 | 11/2020 |
| WO | 2021141758 A1 | 7/2021 |

OTHER PUBLICATIONS

Borucki et al. (PLoS One. Dec. 2019; 14 (12): e0225699.*
Duggal et al. (Virology. 2019; 530: 19-26).*
Musso et al. (Clinical Microbiology Reviews. Jul. 2016; 29 (3): 487-524).*
Faye et al. (PLoS Neglected Tropical Diseases. 2014; 8(1): e2636).*
Pattnaik et al. (Vaccines. 2020; 8 (2): 266).*
Abbink et al. (Nature. Oct. 2018; 16: 594-600).*
Marban-Castro et al. (European Journal of Obstetrics and Gynecology and Reproductive Biology. 2021; 265: 162-168).*
Baldwin, Whitney R., et al. "Purified Inactivated Zika Vaccine Candidates Afford Protection Against Lethal Challenge in Mice"; Scientific Reports; Published Online Nov. 7, 2018.
Druelle, Johan, et al. "Wild Type Measles Virus Attenuation Independent of Type I IFN"; Virology Journal; Published Feb. 3, 2008.
Shan, Chao, et al. "A Live-Attenuated Zika Virus Vaccine Candidate Induces Sterilizing Immunity in Mouse Models" Nature Medicine; vol. 23, No. 6; Jun. 2017.
Weger-Lucarelli, James, et al. "Development and Characterization of Recombinant Virus Generated from a New World Zika Virus Infectious Clone"; American Society for Microbiology, Journal of Virology; vol. 91, Issue 1; Jan. 2017.
Wilder-Smith, Annelies, et al. "Epidemic Arboviral Diseases: Priorities for Research and Public Health"; The Lancet; vol. 17; Mar. 2017.
Monath, T. P., et al; "An Inactivated Cell-Culture Vaccine against Yellow Fever"; The New England Journal of Medicine 364;14; Apr. 7, 2011.
Mueller, J. A., et al; "Inactivation and Environmental Stability of Zika Virus"; Emerging Infectious Diseases; vol. 22; No. 9; Sep. 2016.
Orlinger, K. K., et al; "An inactivated West Nile Virus vaccine derived from a chemically synthesized cDNA system"; Vaccine vol. 28; (2010); p. 3318-3324.
Pereira, R. C., et al; "An inactivated yellow fever 17DD vaccine cultivated in Vero cell cultures"; Vaccine vol. 33; (2015); p. 4261-4268 (Duplicate See Part I, p. 4).
Database GenBank Accession No. MH916806.1; "Zika virus strain ZIKV/*Homo sapiens*/PRI/PRVABC59_8/2015, complete genome",

(56) References Cited

OTHER PUBLICATIONS

Retrieved from GenBank Accession No. MH916806.1; Oct. 17, 2018, https://www.ncbi.nlm.nih.gov/nuccore/MH916806.1, 8 pages.
Poore, E. A., et al; "Pre-clinical development of a hydrogen peroxide-inactivated West Nile virus vaccine"; Vaccine; Jan. 5, 2017; 35(2): 283-292; doi:10.1016/j.vaccine.2016.11.080.
Putnak, J. R., et al; "An evaluation of dengue type-2 inactivated, recombinant subunit, and live-attenuated vaccine candidates in the rhesus macaque model"; Vaccine; vol. 23; (2005); p. 4442-4452.
Rey, F. A., et al; "The bright and the dark side of human antibody responses to flaviviruses: lessons for vaccine design"; EMBO reports; vol. 19; No. 2; 2018.
Tiwari, M., et al; "Assessment of immunogenic potential of Vera adapted formalin inactivated vaccine derived from novel ECSA genotype of Chikungunya virus"; Vaccine; vol. 27; (2009); p. 2513-2522.
Trent, D. W.; "Antigenic Characterization of Flavivirus Structural Proteins Separated by Isoelectric Focusing" Journal of Virology; vol. 22; No. 3; Jun. 1977; p. 608-618.
Wang, W.; "Protein aggregation and its inhibition in biopharmaceutics"; Internaional Journal of Pharmaceutics; vol. 289; (2005); p. 1-30.
NCT02952833 "Zika Vaccine in Naive Subjects", Clinical Trials.gov, Nov. 2, 2016, Retrieved from internet Apr. 30, 2022, 11 pages.
World Health Organization; "WHO global consultation of research related to Zika virus infection"; Mar. 7-9, 2016; www.who.int.
Press Release; World Health Organization; "WHO and experts prioritize vaccines, diagnostics and innovative vector control tools for Zika R&D"; Mar. 9, 2016.
Database GenBank Accession No. MK028857.1; "Zika virus isolate Zika virus/*H. sapiens*-tc/Puerto Rico/2015/PRVABC59 polyprotein gene, complete cds", Retrieved from GenBank Accession No. MK028857.1; Oct. 17, 2018, https://www.ncbi.nlm.nih.gov/nuccore/MK028857.1, 5 pages.
Brinton, M. A.; "Replication of Flaviviruses"; The Togaviridae and Flaviviridae; Plenum Press; New York; 1986.
Juskewitch, J. E., et al; "Lessons from the Salk Polio Vaccine: Methods for and Risks of Rapid Translation"; CTS Journal; vol. 3; No. 4; p. 182-185, 2010.
Westaway, E. G., et al; "Flaviviridae"; Intervirology vol. 24; p. 183-192; 1985.
NCT04478656 "Safety and Immunogenicity of BBV121 (Zika)", Clinical Trials.gov, Jul. 21, 2020, Retrieved from internet Apr. 30, 2022, 9 pages.
Duggal, N. K., et al; "Mutations present in a low-passage Zika virus isolate result in attenuated pathogenesis in mice"; Virology vol. 530; 2019; p. 19-26.
Lanciotti, R. S., et al; "Phylogeny of Zika Virus in Western Hemisphere, 2015"; Emerging Infectious Diseases; www.cdc.gov/eid; vol. 22; No. 5; May 2016.
Yun, S.-I., et al; "Complete Genome Sequences of Three Historically Important, Spatiotemporally Distinct, and Genetically Divergent Strains of Zika Virus: MR-766, P6-740, and PRVABC-59"; Genome Announcements; vol. 4; Issue 4; Jul./Aug. 2016.
Schmaljohn, A. L., et al; "Chapter 54: Alphaviruses (Togaviridae) and Flaviviruses (Flaviviridae)"; Medical Microbiology; 4th edition; Galveston (TX): University of Texas Medical Branch at Galveston; 1996.
Berger, A.; "Science commentary: Th1 and Th2 responses: what are they?"; BMJ; vol. 321; Aug. 12, 2000.
Demicheli, V., et al; "Vaccines for preventing tick-borne encephalitis (Review)"; Cochrane Database of Systematic Reviews 2009; Issue 1; Art. No. CD000977; 2009.
Eckels, K. H., et al; "Formalin-Inactivated Whole Virus and Recombinant Subunit Flavivirus Vaccines"; Advances in Virus Research; vol. 61; 2003.
Chiron Behring Vaccines; "Fachinformation—Encepur Erwachsene"; Mar. 2005.
NCT03425149 "Randomized, Placebo-controlled, Observer-blinded Phase 1 Safety and Immunogenicity Study of Inactivated Zika Virus Vaccine Candidate in Healthy Adults", Clinical Trials.gov, Feb. 7, 2018, Retrieved from Internet Apr. 30, 2022, 9 pages.
Erra, E. O., et al; "The Vero cell-derived, inactivated, SA14-14-2 strain-based vaccine (Ixiaro) for prevention of Japanese encephalitis"; Expert Review of Vaccines; 14(9); p. 1167-1179; Jul. 10, 2015.
Eurosurveillance; "Special edition: Chikungunya and Zika virus"; www.eurosurveillance.org; Oct. 2014.
Fernandez, S., et al; "An Adjuvanted, Tetravalent Dengue Virus Purified Inactivated Vaccine Candidate Induces Long-Lasting and Protective Antibody Responses Against Dengue Challenge in Rhesus Macaques"; Am. J. Trop. Med. Hyg.; vol. 92(4); 2015; p. 698-708; doi:10.4269/ajtmh. 14-0268.
Baxter Corporation; "FSME-IMMUN; Tick-Borne Encephalitis Virus Vaccine, Inactivated, with Adjuvant"; Appendix I; Product Monograph Template; Schedule D; Jul. 7, 2010.
Glaxosmithkline; "Fachinformation—Havrix 1440"; Dec. 2008.
Heinz, F. X., et al; "Flaviviruses and flavivirus vaccines"; Vaccine vol. 30; 2012; p. 4301-4306.
Ioos, S., et al; "Current Zika virus epidemiology and recent epidemics"; Médecine et maladies infectieuses vol. 44; 2014; p. 302-307.
Ishikawa, T., et al; "A review of successful flavivirus vaccines and the problems with those flaviviruses for which vaccines are not yet available"; Vaccine vol. 32; 2014; p. 1326-1337.
European Medicines Agency; "Assessment report for IXIARO"; 2009.
Product Characteristics; "IXIARO, Annex I".
Larocca, R. A.; "Vaccine protection against Zika virus from Brazil"; Nature; vol. 536; Aug. 25, 2016.
Pivnick, H., et al; "Preservatives for Poliomyelitis (Salk) Vaccine III"; Journal of Pharmaceuticals Sciences; vol. 53; No 8; p. 899-901; Aug. 1964.
Sanders, B., et al; "Chapter 2; Inactivated Viral Vaccines"; Vaccine Analysis: Strategies, Principles, and Control; DOI 10.1007/978-3-662-45024-6_2; 2015; p. 45-80.
Database GenBank Accession No. KU501215.1; "Zika virus strain PRVABC59, complete genome", Retrieved from GenBank Accession No. KU501215.1; Feb. 1, 2016, https://www.ncbi.nlm.nih.gov/nuccore/KU501215, 4 pages.
Spellberg, B., et al; "Type 1 / Type 2 Immunity in Infectious Diseases"; Clinical Infectious Diseases; 2001; vol. 32 p. 76-102.
Srivastava, A. K., et al; "A purified inactivated Japanese encephalitis virus vaccine made in vero cells"; Vaccine vol. 19; 2001; p. 4557-4565.
NCT03008122 "Phase 1, Randomized, Double-blinded, Placebo-Controlled Dose De-escalation Study to Evaluate Safety and Immunogenicity of Alum Adjuvanted Zika Virus Purified Inactivated Vaccine (ZPIV) in Adults in a Flavivirus Endemic Area", Clinical Trials.gov, Jan. 2, 2017, Retrieved from internet Apr. 30, 2022, 10 pages.
Press Release; "Walter Reed Scientists Test Zika Vaccine Candidate"; DOD News; Jun. 9, 2016.
Database GenBank Accession No. KY583506.1; "Synthetic construct polyprotein gene, complete cds", Retrieved from GenBank Accession No. KY583506.1; Feb. 6, 2018, https://www.ncbi.nlm.nih.gov/nuccore/KY583506.1, 5 pages.
Shawan, M. M. A. K., et al; "In Silico Modeling and Immunoinformatics Probing Disclose the Epitope Based Peptide Vaccine Against Zika Virus Envelope Glycoprotein"; Indian Journal of Pharmaceutical and Biological Research (IJPBR); vol. 2(4); p. 44-57; 2014.
Database GenBank Accession No. KX087101.3; "Zika virus strain ZIKV/*Homo sapiens*/PRI/PRVABC59/2015, complete genome", Retrieved from GenBank Accession No. KX087101.3; Nov. 18, 2016, https://www.ncbi.nlm.nih.gov/nuccore/KX087101, 4 pages.
World Health Organization; "Current Zika Product Pipeline"; Product Information; Mar. 3, 2016.
Martinez, L. J., et al; "Safety and Immunogenicity of a Dengue Virus Serotype-1 Purified-Inactivated Vaccine: Results of a Phase 1 Clinical Trial"; Am. J. Trop. Med. Hyg.; vol. 93(3); 2015; p. 454-460, Copyright © 2015 by The American Society of Tropical Medicine and Hygiene.

(56) References Cited

OTHER PUBLICATIONS

Maves, R. C., et al; "Immunogenicity and protective efficacy of a psoralen-inactivated dengue-1 virus vaccine candidate in *Aotus nancymaae* monkeys"; Vaccine vol. 29; (2011); p. 2691-2696.
Monath, T. P., et al; "Inactivated yellow fever 17D vaccine: Development and nonclinical safety, immunogenicity and protective activity"; Vaccine vol. 28; (2010); p. 3827-3840.
Pereira, R. C., et al; "An inactivated yellow fever 17DD vaccine cultivated in Vero cell cultures"; Vaccine vol. 33; (2015); p. 4261-4268.
Petersen, L. R., et al; "Zika Virus"; The new england journal of medicine; Mar. 30, 2016; 374:1552-63; DOI: 10.1056/NEJMra1602113; Massachusetts Medical Society.
Pinto, A. K., et al; "A Hydrogen Peroxide-Inactivated Virus Vaccine Elicits Humoral and Cellular Immunity and Protects against Lethal West Nile Virus Infection in Aged Mice"; Journal of Virology p. 1926-1936; Feb. 2013; vol. 87; No. 4.
Press Release; "Crucell Gains Approval and Moves to Recruitment for West Nile Vaccine Phase I Clinical Study"; Leiden, The Netherlands, Dec. 16, 2005.
Hombach, J.; "WHO Draft Target Product Profile: A vaccine to protect against congenital Zika virus syndrome in neonates, for use during an emergency"; World Health Organization, Jun. 6, 2016.
Baldwin, W. R., et al; "Purified Inactivated Zika Vaccine Candidates Afford Protection against Lethal Challenge in Mice"; Scientific Reports | (2018) 8:16509 | DOI:10.1038/s41598-018-34735-7.
Han, H. H., et al; "Safety and immunogenicity of a purified inactivated Zika virus vaccine candidate in healthy adults: an observer-blind, randomised, phase 1 trial"; www.thelancet com/infection; vol. 21; May 18, 2021.
Young, G., et al; "Complete protection in Macaques Conferred by Purified Inactivated Zika Vaccine: Defining a Correlate of protection"; Scientific Reports | (2020) 10:3488 | https://doi.org/10.1038/s41598-020-60415-6.
Abbink, P., et al; "Durability and Correlates of Vaccine Protection Against Zika Virus in Rhesus Monkeys"; Sci Transl Med. Dec. 13, 2017; 9(420); available in PMC Jun. 13, 2018.
Modjarrad, K., et al; "Preliminary aggregate safety and immunogenicity results from three trials of a purified inactivated Zika virus vaccine candidate: phase 1, randomised, double-blind, placebo-controlled clinical trials"; www.thelancet.com; vol. 391; Feb. 10, 2018.
Sumathy, K.; "Protective efficacy of Zika vaccine in AG129 mouse model"; Scientific Reports (2017) | 7:46375 | DOI 10.1038/srep46375.
Abbink, P., et al; "Protective efficacy of multiple vaccine platforms against Zika virus challenge in rhesus monkeys"; sciencemag.org; Sep. 9, 2016; vol. 353; Issue 6304.
Baronti, C., et al; "Complete Coding Sequence of Zika Virus from a French Polynesia Outbreak in 2013"; Published online Jun. 5, 2014 doi: 10.1128/gen0meA.00500-14.
Cohen, J.; "The race for a Zika vaccine is on"; sciencemag.org; Feb. 5, 2016; vol. 351; Issue 6273.
Cox, B. D.; "Predicting Zika virus structural biology: Challenges and opportunities for intervention"; Antiviral Chemistry and Chemotherapy; 2015, vol. 24(3-4); pp. 118-126.
Hombach, J., et al; Report on a WHO consultation on immunological endpoints for evaluation of new Japanese encephalitis vaccines,WHO, Geneva, Sep. 2-3, 2004; Available online at www.sciencedirect.com; Vaccine vol. 23; (2005) 5205-5211; Jul. 18, 2005.
Lahon, A., et al; "Characterization of a Zika Virus Isolate from Colombia"; PLOS Neglected Tropical Diseases; DOI:10.1371/journal.pntd.0005019; Sep. 21, 2016.
Schlegl, R., et al; "Influence of elemental impurities in aluminum hydroxide adjuvant on the stability of inactivated Japanese Encephalitis vaccine, IXIARO®"; Vaccine vol. 33 (2015) 5989-5996.

Valneva Press Release; "Valneva Announces Successful Generation of a Highly-purified Zika Vaccine Candidate Using its FDA-EMA Approved Japanese Encephalitis Platform"; Lyon (France); Jul. 7, 2016.
WHO/UNICEF; Zika Virus Vaccine Target Product Profile for Emergency use; "WHO Zika Virus (ZIKV) Vaccine Target Product Profile (TPP): Vaccine to protect against congenital Zika virus syndrome for use during an emergency" Jul. 2016.
Villordo, S. M., et al; "RNA Structure Duplications and Flavivirus Host Adaptation"; Trends in Microbiology, Apr. 2016, vol. 24, No. 4.
Kuno, G., et al; "Full-length sequencing and genomic characterization of Bagaza, Kedougou, and Zika viruses"; Arch Virol (2007) 152: 687-696; DOI 10.1007/s00705-006-0903-z; Printed in the Netherlands.
Musso, D., et al; "Zika Virus"; Clinical Microbiology Reviews; Jul. 2016; vol. 29; No. 3.
Wang, L., et al; "From Mosquitos to Humans: Genetic Evolution of Zika Virus"; Cell Host & Microbe 19; May 11, 2016; Elsevier Inc.
NCT02937233 "Zika Virus Purified Inactivated Vaccine (ZPIV) Accelerated Vaccination Schedule Study (Z001)", Clinical Trials.gov, Oct. 18, 2016, Retrieved from internet Apr. 30, 2022, 11 pages.
Haddow, A. D., "Distinguishing between Zika and Spondweni viruses"; Bull World Health Organ 2016; 94:711-711A; doi: http://dx.doi.org/10.2471/BLT.16.181503.
Dowd, K. A., et al; "Broadly Neutralizing Activity of Zika Virus-Immune Sera Identifies a Single Viral Serotype"; Cells Reports 16; 1485-1491; Aug. 9, 2016.
Lednicky, J., et al; "Zika Virus Outbreak in Haiti in 2014: Molecular and Clinical Data"; PLOS Neglected Tropical Diseases | DOI:10.1371/journal.pntd.0004687; Apr. 25, 2016.
Sifferlin, A.; "U.S. Launches 'Full-court Press' for a Zika Vaccine"; The Wayback Machine; https://web.archive.org/web/20160122154151/http://time.com/4188973/zika-virus-vaccine-nih/; Jan. 21, 2016.
Intercell AG; IXIARO; (Japanese Encephalitis Vaccine, Inactivated, Adsorbed); Suspension for Intramuscular Injection; Initial U.S. Approval: 2009.
Bozzo, P., et al; "Vaccination during pregnancy"; Canadian Family Physician (Le Médecin de famille canadien); vol. 57; May 2011.
Pan American Health Organization; "Neurological syndrome, congenital malformations, and Zika virus infection. Implicatons for public health in the Americas"; Epidemiological Alert; Dec. 1, 2015.
Foy, B. D. et al; "Probable Non-Vector-borne Transmission of Zika Virus, Colorado, USA"; Emerging Infectious Diseases; www.cdc.gov/eid; vol. 17; No. 5; May 2011.
Hamel, R., et al; "Biology of Zika Virus Infection in Human Skin Cells"; Journal of Virology; vol. 89; No. 17; Sep. 2015.
Musso, D., et al; "Potential Sexual Transmission of Zika Virus"; Emerging Infectious Diseases; www.cdc.gov/eid; vol. 21; No. 2; Feb. 2015.
Oehler, E., et al; "Zika virus infection complicated by Guillain-Barré syndrome—case report, French Polynesia"; www.eurosurveillance.org; published Mar. 6, 2014.
Press Release; "An Indian biotech company has been developing Zika vaccines for over a year"; https://qz.com/india/609291/this-indian-biotech-firm-is-the-worlds-first-t . . . ; Feb. 4, 2016.
Heang, V., et al; "Zika Virus Infection, Cambodia, 2010"; Emerging Infectious Diseases; www.cdc.gov/eid; vol. 18; No. 2; Feb. 2012.
NCT03343626 "Safety, Immunogenicity, and Dose Ranging Study of Inactivated Zika Virus Vaccine in Healthy Participants", Clinical Trials.gov., Nov. 17, 2017, Retrieved from internet Apr. 30, 2022, 13 pages.
Allison, S. L., et al; "Oligomeric Rearrangement of Tick-Borne Encephalitis Virus Envelope Proteins Induced by an Acidic pH"; Journal of Virology; Feb. 1995; pp. 695-700; vol. 69; No. 2.
Cao-Lormeau, V.-M.; "Tropical Islands as New Hubs for Emerging Arboviruses"; Emerging Infectious Diseases; www.cdc.gov/eid; vol. 22; No. 5; May 2016.
Dai, L., et al; "Molecular Basis of Antibody-Mediated Neutralization and Protection Against Flavivirus"; IUBMB Life; vol. 68; No. 10; Oct. 2016; pp. 783-791.

(56) References Cited

OTHER PUBLICATIONS

Firbas, C., et al; "Product review on the JE vaccine IXIARO"; www.tandfonline.com; Human Vaccines & Immunotherapeutics 11:2, 411-420; Feb. 2015.

Kimura-Kuroda, J., et al; "Protection of Mice Against Japanese Encephalitis Virus by Passive Administration With Monoclonal Antibodies"; The Journal of Immunology; vol. 141. 3606-3610; No. 10; Nov. 15, 1988.

Maves, R. C., et al; "Immunogenicity and protective efficacy of a psoralen-inactivated dengue-1 virus vaccine candidate in *Aotus nancymaae* monkeys"; Vaccine vol. 29 (2011); 2691-2696.

Metz, S. W., et al; "Oligomeric state of the ZIKV E protein defines protective immune responses"; Nature Communications; 2019; https://doi.org/10.1038/s41467-019-12677-6.

Modis, Y., et al; "Structure of the dengue virus envelope protein after membrane fusion"; NATURE; vol. 427; Jan. 22, 2004; www.nature.com/nature.

Reagan, R. L., et al; "Electron Micrographs of Erythrocytes From Swiss Albino Mice Infected With Zika Virus"; From the Virus Laboratory, Live Stock Sani Service, University of Maryland, College Park, Maryland. Received for publication Apr. 28, 1955.

Breitt, U.; "Zika-Virus-Infektionen"; Laboratoriumsmedizin; https://www.mta-dialog.de/artikel/zika-virus-infektionen.html; Apr. 1, 2016.

CTRI/2017/05/008539 "A Phase 1 clinical trial to evaluate safety and effectiveness of ZIKA vaccine in healthy adults.", ctri.nic.in/Clinicaltrials, Jul. 18, 2018, Retrieved from internet Apr. 30, 2022, 6 pages.

Pan American Health Organization (PAHO)/World Health Organization (WHO); "Epidemiological Alert—Zika Virus Infection"; May 7, 2015.

NCT02963909 "A Phase 1, First-in-human, Double-blinded, Randomized, Placebo-controlled Trial of a Zika Virus Purified Inactivated Vaccine (ZPIV) With Alum Adjuvant in Healthy Flavivirus-naive and Flavivirus-Primed Subjects.", Clinical Trials.gov, Nov. 15, 2016, Retrieved from internet Apr. 30, 2022, 12 pages.

Yang, Z., et al; "Culture Conditions and Types of Growth Media for Mammalian Cells"; Intech open science; http://dx.doi.org/10.5772/52301; 2012.

Way, H., et al; "Comparative Studies of some African Arboviruses in Cell Culture and in Mice"; J. gen. Virol; vol. 30; 1976; p. 123-130.

WHO Technical Report; "Guidelines on viral inactivation and removal procedures intended to assure the viral safety of human blood plasma products"; Series No. 924; 2004.

Toriniwa, H., et al; "Long-term stability of Vero cell-derived inactivated Japanese encephalitis vaccine prepared using serum-free medium"; Vaccine vol. 26; 2008; p. 3680-3689.

Database GenBank Accession No. KX601168.1; "Zika virus strain ZIKV/*Homo sapiens*/PRI/PRVABC59/2015, complete genome", Retrieved from GenBank Accession No. KX601168.1; Jul. 25, 2016, https://www.ncbi.nlm.nih.gov/nuccore/KX601168.1, 5 pages.

Zent, O., et al; "Safety, immunogenicity and tolerability of a new pediatric tick-borne encephalitis (TBE) vaccine, free of protein-derived stabilizer"; Vaccine; vol. 21; (2003); p. 3584-3592.

Database GenBank Accession No. MH158237.1; "Zika virus isolate PRVABC59, complete genome", Retrieved from GenBank Accession No. MH158237.1; May 9, 2018, https://www.ncbi.nlm nih.gov/nuccore/MH158237.1, 5 pages.

Pinto, A. K., et al; A Hydrogen Peroxide-Inactivated Virus Vaccine Elicits Humoral and Cellular Immunity and Protects against Lethal West Nile Virus Infection in Aged Mice; Journal of Virology, Feb. 2013 vol. 87 No, 4, p. 1926-1936.

Abbink, P. et al., "Zika virus vaccines", Nature. Oct. 2018; 16: 594-600.

Baldwin et al., "Purified Inactivated Zika Vaccine Candidates Afford Protection against Lethal Challenge in Mice," Scientific Reports, vol. 8, No. 1, Nov. 7, 2018 (Nov. 7, 2018).

Barreto-Vieira et al: "Structural investigation of C6/36 and Vero cell cultures infected with a Brazilian Zika virus," PLOS One, vol. 12, No. 9, Sep. 12, 2017 (Sep. 12, 2017), p. e0184397.

Blümel et al., "Inactivation and removal of Zika virus during manufacture of plasma-derived medicinal products : Inactivation of Zika Virus", Transfusion., vol. 57, No. 3pt2, Oct. 12, 2016 (Oct. 12, 201), p. 790-796.

Castanha and Marques, The Lancet, Sep. 2021, vol. 21, pp. 1198-1200.

Druelle, J. et al., "Wild type measles virus attenuation independent of type I IFN", Virology Journal, vol. 5, No. 1, Jan. 1, 2008 (Jan. 1, 2008), p. 22.

Duggal, N. et al., "Mutations present in low-passage Zika virus isolated result in attenuated pathogenesis in mice", Virology. 2019; 530: 19-26.

Faye, O. et al., "Molecular Evolution of Zika Virus during its Emergence", PLoS Neglected Tropical Diseases. 2014; 8 (1): e2636.

GenBank Accession No. KX377337.1, Jun. 22, 2016.

Haddow, A. et al., "Genetic Characterization of Zika Virus Strains: Geographic Expansion of the Asian Lineage", PLoS Neglected Tropical Diseases 2012; 6 (2): e1477.

Han et al., Lancet Infect Dis, 2021, 21:1282-1292.

Marban-Castro, E. et al., "Zika Virus Infection in pregnant women and their children: A review", (European Journal of Obstetrics and Gynecology and Reproductive Biology 2021; 265:162-168).

Musso, D. et al., Clinical Microbiology Reviews. Jul. 2016; 29 (3): 487-524.

Narasimhan, H. et al., PLoS Negi Trop Dis, 2020, 14(10):e0008707.

News Release from NIAID on Aug. 3, 2016 for Clinical Trial NCT02840487, available from www.niaid.nih.gov/news-events/nih-begins-testing-investigational-zika-vaccine-humans, accessed Feb. 9, 2022, 7 pages.

Pattnaik, A. et al., "Current Status of Zika Virus Vaccines: Successes and Challenges", Vaccines. 2020; 8 (2): 266.

Shan, C. et al., "A live-attenuated Zika virus vaccine candidate induces sterilizing immunity in mouse models", Nature Medicine, vol. 23, No. 6, Apr. 10, 2017 (Apr. 10, 2017), p. 763-767.

Weger-Lucarelli, J. et al., "Development and Characterization of Recombinant Virus Generated from a New World Zika Virus Infectious Clone", Journal of Virology., vol. 91, No. 1, Oct. 19, 2016 (Oct. 19, 2016).

Wilder-Smith, A. et al, "Epidemic arboviral diseases: priorities for research and public health", The Lancet, Dec. 20, 2016 (published online), vol. 17 p. e101-e106.

Brown et al., "Extended Surface for Membrane Association in Zika Virus NS1 Structure" Nat. Struct. Mol. Biol. 2016; 23(9): 865-867, published on Jul. 25, 2016.

Gudlavalleti, S. et al., "Determining trace amounts and the origin of formaldehyde impurity in Neisseria meningitidis A/C/Y/W-135-DT conjugate vaccine formulated in isotonic aqueous 1x PBS by improved C18-UPLC method," Journal of Pharmaceutical and Biomedical Analysis, Mar. 25, 2015, vol. 107, pp. 432-436.

Hassan, J. et al., "Application of low density miniaturized dispersive liquid-liquid extraction method for determination of formaldehyde in aqueous samples (water, fruit juice and *Streptococcus* vaccine) by HPLC-UV," Journal of Analytical Chemistry, Nov. 21, 2015, vol. 70, pp. 1495-1500.

Excerpt of European Pharmacopoeia 5.4, Vaccines for human use, Apr. 2006, pp. 3838-3840.

Excerpt of European Pharmacopoeia 5.8, Vaccines for human use, Jul. 2007, pp. 5231-5233.

Mitkus, R. et al., "Pharmacokinetic modeling as an approach to assessing the safety of residual formaldehyde in infant vaccines," Vaccine, Jun. 7, 2013, 31:2738-2743.

Product Information IMOVAX® Polio, Alberta Health Services, Polio Vaccine Biological Page, Section 7: Biological Product Information, Standard #: 07.300, Mar. 1, 2013 (revised May 4, 2022), pp. 1-6.

Product Information TDVAX®, Tetanus and Diphtheria Toxoids Adsorbed, NDC 14362-0111-3 and NDC 14362-0111-4, MassBiologics, Sep. 2018, 7 pages.

Orenstein, W., et al., "Global Vaccination Recommendations and Thimerosal," Pediatrics, vol. 131, No. 1, Jan. 2013.

Pato, T., et al., "Development of a membrane adsorber based capture step for the purification of yellow fever virus," Elsevier, Vaccine 32, pp. 2789-2793, Mar. 11, 2014.

(56) References Cited

OTHER PUBLICATIONS

Pierson, T., et al., "Degrees of maturity: the complex structure and biology of flaviviruses," SciVerse ScienceDirect, pp. 168-175, 2012.
Plevka, P., et al., "Maturation of flaviviruses starts from one or more icosahedrally independent nucleation centres," EMBO Reports, vol. 12, No. 6, pp. 602-606, May 13, 2011.
Plotkin, S., et al., "The development of vaccines: how the past led to the future," Nature, vol. 9, Dec. 2011.
Poland, G., et al., "Zika Vaccine Development: Current Status," Mayo Clinic, Thematic Review On Vaccines, Mayo Foundation for Medical Education and Research, pp. 2572-2586, 2019.
Putnak, R., et al., "Development of a Purified, Inactivated, Dengue-2 Virus Vaccine Prototype in Vero Cells: Immunogenicity and Protection in Mice and Rhesus Monkeys," The Journal of Infectious Diseases, vol. 174, pp. 1176-1184, 1996.
Rasmussen, S.A., et al., "Vaccines and pregnancy: Past, present, and future," Seminars in Fetal & Neonatal Medicine, vol. 19, pp. 161-169, 2014.
Rodrigues, A., et al., "Viral vaccines and their manufacturing cell substrates: New trends and designs in modern vaccinology," Biotechnol. J vol. 10, pp. 1329-1344, Jun. 26, 2015.
Roehrig, J.T., et al., "Guidelines for Plaque-Reduction Neutralization Testing of Human Antibodies to Dengue Viruses," Viral Immunology, vol. 21, No. 2, 2008.
Salk, J., et al., Formaldehyde Treatment and Safety Testing of Experimental Poliomyelitis Vaccines, American Journal of Public Health, vol. 44, No. 5, pp. 563-570, May 1954.
Samarasekera, U., et al., "Concern over Zika virus grips the world," The Lancet, vol. 387, Feb. 6, 2016.
Schellack, C., et al., "IC31, a novel adjuvant signaling via TLR9, induces potent cellular and humoral immune responses," Vaccine, vol. 24, pp. 5461-5472, Apr. 7, 2006.
Schuller, E., et al., "Comparison of a single, high-dose vaccination regimen to the standard regimen for the investigational Japanese encephalitis vaccine, IC51: A randomized, observer-blind, controlled Phase 3 study," Vaccine, vol. 27, pp. 2188-2193, 2009.
Schuller, E., et al., "Long-term immunogenicity of the new Vero cell-derived, inactivated Japanese encephalitis virus vaccine IC51 Six and 12 month results of a multicenter follow-up phase 3 study," Vaccine, vol. 26, pp. 4382-4386, 2008.
Shan, C., et al.,"Zika Virus: Diagnosis, Therapeutics, and Vaccine," ACS Infect. Dis., vol. 2, pp. 170-172, 2016.
Shan, C., et al., "An Infectious cDNA Clone of Zika Virus to Study Viral Virulence, Mosquito Transmission, and Antiviral Inhibitors," Cell Host & Microbe, vol. 19, pp. 891-900, Jun. 8, 2016.
Sirohi, D., et al., The 3.8Å resolution cryo-EM structure of Zika Virus, Science, 352(6284), pp. 467-470, Apr. 22, 2016.
Smith, D.W., et al., "Zika virus and Guillain-Barré syndrome: another viral cause to add to the list," The Lancet, vol. 387, Apr. 9, 2016.
Sofer, G., "Virus Inactivation in the 1990s—and into the 21st Century," BioPharm International, Culture Media, Biotechnology Products, and Vaccines, Part 4, pp. 50-57, Jan. 2003.
Souza, M., et al., "Production of yellow fever virus in microcarrier-based Vero cell cultures," Elsevier, Vaccine 27, pp. 6420-6423, Jun. 24, 2009.
Stephenson, K., et al., "Safety and immunogenicity of a Zika purified inactivated virus vaccine given via standard, accelerated, or shortened schedules: a single-centre, double-blind, sequential-group, randomised, placebo-controlled, phase 1 trial," Lancet Infect Dis 2020, pp. 1061 70, May 6, 2020.
Tan, T., et al., "Capsid protein structure in Zika virus reveals the flavivirus assembly process," Nature Communications, pp. 1-13, 2020.
Tauber, E., et al., "Safety and immunogenicity of a Vero-cell-derived, inactivated Japanese encephalitis vaccine: a non-inferiority, phase III, randomised controlled trial," The Lancet, vol. 370, Dec. 1, 2007.
Thomas, S.J., "A Phase II, Randomized, Safety and Immunogenicity Study of a Re-Derived, Live-Attenuated Dengue Virus Vaccine in Healthy Adults," Am. J. Trop Med. Hyg., vol. 88, No. 1, pp. 73-88, 2013.
Wang et al.; "Development of reverse high performance liquid chromatography method for determination of free trace formaldehyde in influenza virus split vaccine", Chinese Journal of Biologicals, 2016, vol. 29, No. 11, p. 1210-1214.
Watanaveeradej, V., et al., "Safety and Immunogenicity of a Rederived, Live-Attenuated Dengue Virus vaccine in Healthy Adults Living in Thailand: A Randomized Trial," Am. J. Trop. Med. Hyg., 91(1), pp. 119-128, 2014.
World Health Organization, "Changing health systems with better data," WHO, Mar. 10, 2016.
World Health Organization; "Director-General summarizes the outcome of the Emergency Committee regarding clusters of microcephaly and Guillain-Barré syndrome," Feb. 1, 2016.
World Health Organization; "Zika Virus Microcephaly and Guillain-Barré Syndrome"Situation Report, Mar. 17, 2016.
Yoshii, K., et al., "A conserved region in the prM protein is a critical determinant in the assembly of flavivirus particles". Journal of General Virology, vol. 93, pp. 27-38, 2012.
Zhang, X., et al., "Genetic and biochemical characterizations of Zika virus NS2A protein," Emerging Microbes & Infections, vol. 8, 2019.
Annunziato, F., et al., "The 3 major types of innate and adaptive cell-mediated effector immunity," Journal of Allergy Clin. Immunology, vol. 135, No. 3, Dec. 2014.
Aubry, F., et al., "Flavivirus reverse genetic systems, construction techniques and applications: A historical perspective," Elsevier, Antiviral Research, vol. 114, pp. 67-85, Dec. 12, 2014.
Bahnemann, H., Inactivation of viral antigens for vaccine preparation with particular reference to the application of binary ethylenimine, Vaccine, vol. 8, pp. 299-303Aug. 1990.
Baldwin, W., et al., "Development, characterization, and Pre-Clinical Immunogenicity and Efficacy of a Purified, Inactivated Zika Virus Vaccines (PIZV) Candidate," Am. J. Trop. Med. Hyg. vol. 97, Issue 5, Suppl., p. 48, Nov. 2, 2017.
Barnard, T., et al., "Molecular Determinants of Flavivirus Virion Assembly," CellPress, Trends in Biochemical Sciences, vol. 46, No. 5, pp. 378-390, May 2021.
Barzon, L., et al., "Zika virus: from pathogenesis to disease control," FEMS Microbiology Letters, vol. 363, No. 18, pp. 1-17, Aug. 21, 2016.
Bauer, K., et al., "A Phase II, Randomized, Safety and Immunogenicity Trial of a Re-Derived, Live-Attenuated Dengue Virus Vaccine in Healthy Children and Adults Living in Puerto Rico," Am. J. Trop. Med. Hyg., vol. 93, No. 3, pp. 441-453, 2015.
Besnard, T.R., et al., "Evidence of perinatal transmission of Zika virus, French Polynesia," Trends in Biochemical Sciences, vol. 46, No. 5, May 2021.
Brinton, M.A., et al., "Functions of the 3' and 5' genome RNA regions of members of the genus Flavivirus," Virus Research, vol. 206, pp. 108-119, 2015.
Burton, D.R., "Antibodies, viruses and vaccines," Nature, vol. 2, Sep. 2002.
Cao-Lormeau, V-M., et al., "Emerging arboviruses in the Pacific," The Lancet, vol. 384, Nov. 1, 2014.
Chen, R., et al., "Dengue—Quo tu et quo vadis?," MDPI, Viruses, vol. 3, pp. 1562-1608, Sep. 1, 2011.
Collette, N., et al., "Single Amino Acid Mutations Affect Zika Virus Replication In Vitro and Virulence In Vivo," MDPI., Viruses, pp. 1-20, Nov. 12, 2020.
Dai, L., et al., "Structures of the Zika Virus Envelope Protein and Its Complex with a Flavivirus Broadly Protective Antibody," Cell Host & Microbe, 19, pp. 696-704, May 11, 2016.
Database GenBank Accession No. AY632535.2, Nov. 23, 2010.
Database GenBank Accession No. KJ776791.1, Jun. 13, 2014.
Database GenBank Accession No. KJ776791.2, Aug. 31, 2016.
Database GenBank Accession No. KU497555.1, Feb. 16, 2016.
DelRue, I., et al., "Inactivated virus vaccines from chemistry to prophylaxis: merits, risks and challenges," Expert Reviews, Vaccines 11(6), pp. 695-719, 2012.

(56) References Cited

OTHER PUBLICATIONS

DiNunno, N., et al., "Identification of a pocket factor that is critical to Zika virus assembly," Nature Communications, pp. 1-8, 2020.

Dufy, M.R., et al. " Zika Virus Outbreak on Yap Island, Federated States of Micronesia," The New England Journal of Medicine, vol. 360, No. 24, Jun. 11, 2009.

Duggan, S.T., et al., "Japanese Encephalitis Vaccine (Inactivated, Adsorbed) [IXIARO®]," Drugs, vol. 69, No. 1, pp. 115-122, 2009.

Dyer, O., "Zika vaccine could be in production by year's end, says Maker," The British Medical Journal, vol. 352, Feb. 2016.

Eckels, K.M., et al., "Japanese encephalitis virus live-attenuated vaccine, Chinese strain SA14-14-2; adaptation to primary canine kidney cell cultures and preparation of a vaccine for human use," Vaccine, vol. 6, Dec. 1988.

Enfissi, A., et al., Zika virus genome from the Americas, The Lancet, vol. 387, pp. 227-228, Jan. 16, 2016.

Emergent Biosolutions, Inc., "Emergent BioSolutions and Valneva Report Positive Phase 1 Results for Their Vaccine Candidate Against the Zika Virus," Emergent Biosolutions, Inc., pp. 1-3, Nov. 19, 2018.

Fauci, A.S., et al., "Zika Virus in the Americas—Yet Another Arbovirus Threat," The New England Journal of Medicine, vol. 374, vol. 7, Feb. 18, 2016.

Fox, M., Could We Have a Zika Vaccine Soon? NBC News Archive, Available at: https://web.archive.org/web/20160130130441/https://www.nbcnews.com/storyline/zika-virus-outbreak/could-we-have-zika-vaccine-soon-n507186 Dated Jan. 30, 2016.

Holloway, T., "WRAIR Technology helps create Japanese Encephalitis Vaccine," Article, Walter Reed Army nstitute of Research, Apr. 14, 2009.

Klasse, P.J., "Neutralization of Virus Infectivity by Antibodies: Old Problems in New Perspectives," Advances in Biology, vol. 2014, Sep. 9, 2014.

Klema, V.J., et al., "Dengue Virus Nonstructural Protein 5 (NS5) Assembles into a Dimer with a Unique Methyltransferase and Polymerase Interface," PLOS Pathogens, Feb. 19, 2016.

Kon, T., et al., "Influenza Vaccine Manufacturing: Effect of Inactivation, Splitting and Site of Manufacturing. Comparison of Influenza Vaccine Production Processes," PLoS One 11(3), pp. 1-19, Mar. 9, 2016.

Kostyuchenko, V., et al., "Structure of the thermally stable Zika virus," Nature, vol. 533, pp. 435-436, May 19, 2016.

Kuhn, R., et al., "Shake, rattle, and roll: Impact of the dynamics of flavivirus particles on their interactions with the host," Virology, pp. 479-480, 508-517, May 2015.

Kuhn, R., et al., "Structure of Dengue Virus: Implications for Flavivirus Organization, Maturation, and Fusion," Cell, vol. 108, pp. 717-725, Mar. 8, 2002.

Kumar, S., et al., "Metal Ion Leachates and the Physico-Chemical Stability of Biotherapeutic Drug Products," Current Pharmaceutical Design, vol. 20, pp. 1173-1181, 2014.

Laurie, K.L., et al., "International Laboratory Comparison of Influenza Microneutralization Assays for A(H1N1)pdm09, A(H3N2), and A(H5N1) Influenza Viruses by Consise, " Clinical and Vaccine Immunology, vol. 22, No. 8, Aug. 2015.

Ledgerwood, J.E., et al., A West Nile Virus DNA Vaccine Utilizing a Modified Promoter Induces Neutralizing Antibody in Younger and Older Healthy Adults in a Phase I Clinical Trial, Journal of Infectious Disease, vol. 203, May 15, 2011.

Li, X-F., et al., "Complete Genome Sequence of a Chikungunya Virus Isolated in Guangdong, China," Journal of Virology, vol. 86, No. 16, pp. 8904 8905, Aug. 2012.

Lindenbach, B.D., et al., "Molecular Biology of Flaviviruses," Advances in Research, vol. 59, 2003.

Loewe, D., et al., Forced Degradation Studies to Identify Critical Process Parameters for the Purification of Infectious Measles Virus, MDPI, Viruses, vol. 11, No. 725, 2019.

Luca, V.C., et al., "Crystal Structure of the Japanese Encephalitis Virus Envelope Protein," Journal of Virology, pp. 2337-2346, Dec. 7, 2011.

Lyons, A., et al., "A Phase 2 study of a purified, inactivated virus vaccine to prevent Japanese encephalitis," Elsevier, ScienceDirect, Vaccine 25, pp. 3445-3453, Jan. 4, 2007.

Ma, X., et al., "Identification and characterization of key residues in Zika virus envelope protein for virus assembly and entry," Emerging Microbes & Infections, vol. 11, 2022.

Markoff, L., "Ixiaro—Summary Basis for Regulatory Action," Available at https://web.archive.org/web/20090619154725/https://www.fda.gov/BiologicsBloodVaccines/Vaccines/ApprovedProducts/ucm142580.htm Dated: Mar. 30, 2009.

Maurice, J., "WHO reveals its shopping list for weapons against Zika," The Lancet, Feb. 16, 2016.

Mukhopadhyay, S., et al. , "A Structural Perspective of the Flavivirus Life Cycle," Microbiology, Mol. 3, Jan. 2005.

Musso, D., "Zika Virus Transmission from French Polynesia to Brazi," Emerging Infectious Diseases, vol. 21, No. 10, Oct. 2015.

Nema, S., et al., "Excipients and Their Role in Approved Injectable Products: Current Usage and Future Directions," PDA Journal of Pharmaceutical Science and Technology, vol. 65, No. 3, pp. 287-332 May-Jun. 2011.

Okada, K., et al., "Safety and immunogenicity of a freeze-dried, cell culture-derived Japanese encephalitis vaccine (Inactivated) (JEBIK®V) in children," Vaccine, vol. 30, pp. 5967-5972, 2012.

\* cited by examiner

FIG. 6

| | | | | | | | | | | | | | | | | Env-330 | | | | | | | | | |
|---|---|---|---|---|---|---|---|---|---|---|---|---|---|---|---|---|---|---|---|---|---|---|---|---|---|
ZIKV PRVABC59 P6e
ZIKV PRVABC59
WNV
JEV
SLEV
YFV
DENV 1 16007
DENV 2 16681
DENV 3 16562
DENV 4 1036

FIG. 7

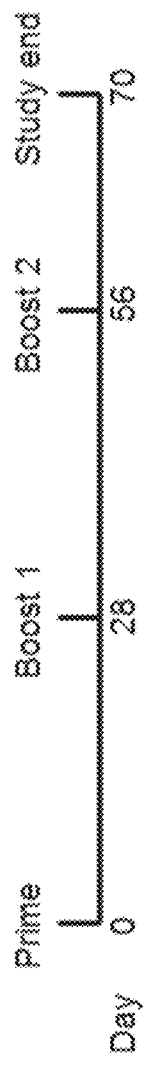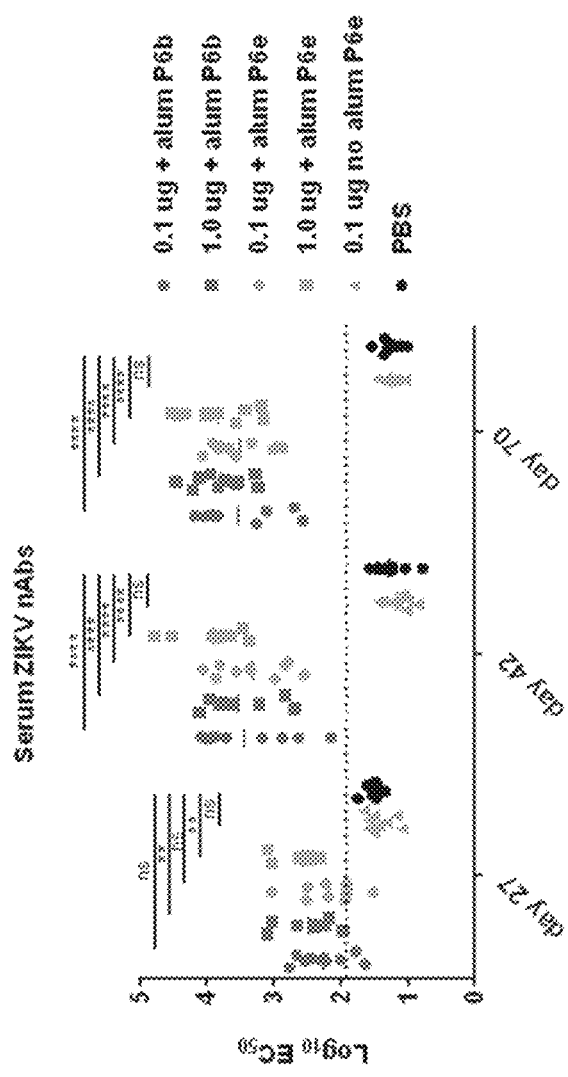

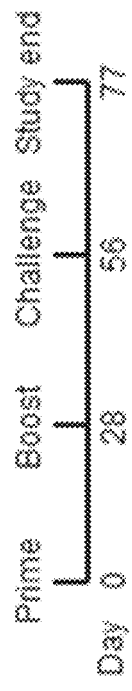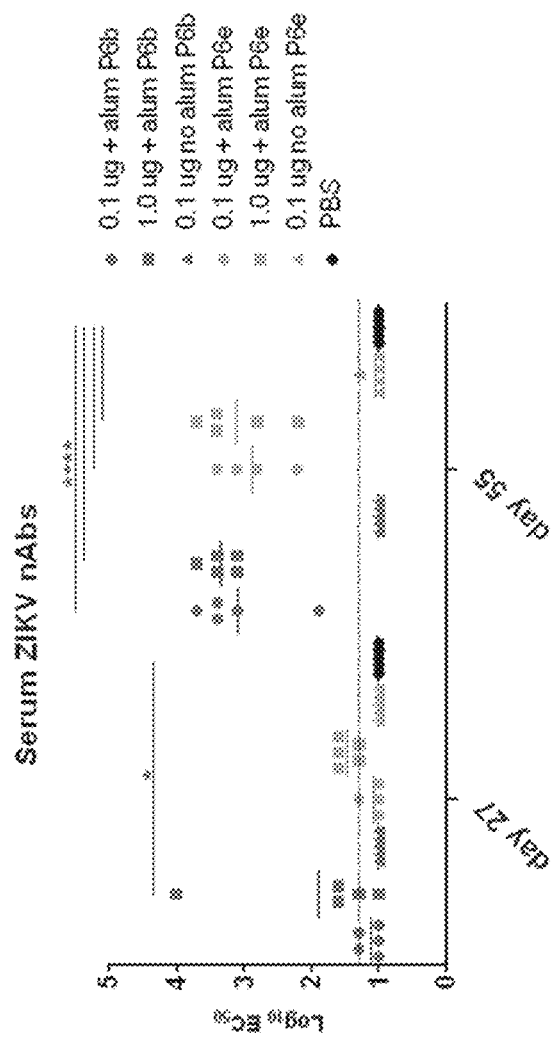
FIG. 13A
FIG. 13B

FIG. 21 correlates of D3 viremia $R^2 = 0.837$
$p < 0.0001$

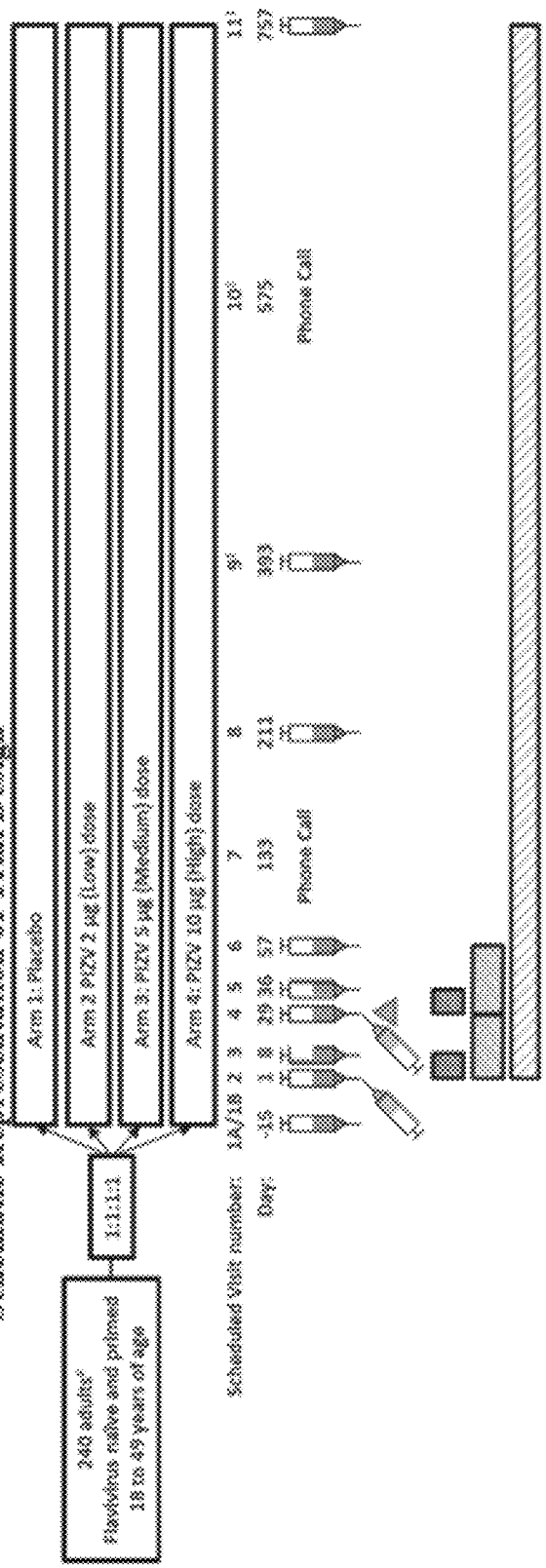
FIG. 25

ZIKA VACCINES AND IMMUNOGENIC COMPOSITIONS, AND METHODS OF USING THE SAME

This is a National Phase Application filed under 35 U.S.C. 371 as a national stage of PCT/US2018/059219, filed Nov. 5, 2018, an application claiming the benefit of Provisional Application No. 62/592,995, filed Nov. 30, 2017, and Provisional Application No. 62/581,500, filed Nov. 3, 2017, the content of each of which is hereby incorporated by reference in its entirety.

STATEMENT REGARDING FEDERALLY-SPONSORED RESEARCH

This invention was made with government support under Contract No. HHSO100201600015C with the Department of Health and Human Services, Office of the Assistant Secretary for Preparedness and Response, Biomedical Advanced Research and Development Authority. This invention was created in the performance of a Cooperative Research and Development Agreement with the Centers for Disease Control and Prevention, an Agency of the Department of Health and Human Services. The Government of the United States has certain rights in the invention.

FIELD OF THE INVENTION

The present disclosure relates to Zika virus vaccines and immunogenic compositions having one or more antigens from a Zika virus (e.g., a Zika virus clonal isolate, a non-human cell adapted Zika virus, etc.) and methods of manufacture, formulation, testing, and uses thereof.

The Sequence Listing submitted in text format (.txt) filed on Apr. 30, 2020, named "SequenceListingaspublished.txt", (created on Jun. 4, 2019, 25 KB), is incorporated herein by reference.

BACKGROUND

Zika virus, a flavivirus classified with other mosquito-borne viruses (e.g., yellow fever, dengue, West Nile, and Japanese encephalitis viruses) within the Flaviviridae family has spread rapidly in a hemispheric-wide epidemic since the virus was introduced into Brazil in 2013. The virus has reached the Central and North Americas, including territories of the United States, consequently now threatening the continental US. Indeed, Zika virus strain PRVABC59 was isolated from serum from a person who had traveled to Puerto Rico in 2015. The genome of this strain has been sequenced at least three times (See Lanciotti et al. Emerg. Infect. Dis. 2016 May; 22(5):933-5 and GenBank Accession Number KU501215.1; GenBank Accession Number KX087101.3; and Yun et al. Genome Announc. 2016 Aug. 18; 4(4) and GenBank Accession Number ANK57897.1).

Initially isolated in 1947 in Uganda, the virus was first linked to human disease in 1952, and has been recognized sporadically as a cause of mild, self-limited febrile illness in Africa and Southeast Asia (Weaver et al. (2016) Antiviral Res. 130:69-80; Faria et al. (2016) Science. 352(6283):345-349). However, in 2007, an outbreak appeared in the North Pacific island of Yap, and then disseminated from island to island across the Pacific, leading to an extensive outbreak in 2013-2014 in French Polynesia, spreading then to New Caledonia, the Cook Islands, and ultimately, to Easter Island. An Asian lineage virus was subsequently transferred to the Western Hemisphere by routes that remain undetermined (Faria et al. (2016) Science. 352(6283):345-349). The virus may be transmitted zoonotically by *Aedes aegypti*, *A. albopictus*, and possibly by *A. hensilli* and *A. polynieseinsis* (Weaver et al. (2016) Antiviral Res. 130:69-80). Additionally, it is thought that other vectors for transmitting the virus may exist, and the virus may be transmitted by blood transfusion, transplacentally, and/or through sexual transmission.

In late 2015, a significant increase in fetal abnormalities (e.g., microcephaly) and Guillain-Barre syndrome (GBS) in areas of widespread Zika virus infection raised alarm that Zika virus might be much more virulent than originally thought, prompting the World Health Organization (WHO) to declare a Public Health Emergency of International Concern (PHEIC) (Heymann et al. (2016) Lancet 387(10020): 719-21). While Zika virus poses a substantial public health threat, no FDA-approved vaccine or treatment currently exists, and the only preventative measures for controlling Zika virus involve managing mosquito populations.

In recent efforts to characterize a recombinant Zika virus for the development of a potential vaccine, a non-human cell adapted Zika virus was identified that harbors a mutation in the viral Envelope protein at position 330 (Weger-Lucarelli et al. (2017) Journal of Virology 91(1): 1-10). The authors of this study found that full-length infectious cDNA clones of Zika virus strain PRVABC59 were genetically unstable when amplified during cloning, and opted to split the viral genome to address the observed instability, developing and applying a two plasmid system. However, a two plasmid system for the development of a Zika vaccine is less desirable.

BRIEF SUMMARY

Thus, there is a need to develop vaccines and immunogenic compositions for treating and/or preventing Zika virus infection that utilize a genetically stable Zika virus that does not require a two vector system. To meet the above and other needs, the present disclosure is directed, at least in part, to a genetically stable non-human cell adapted Zika virus harboring an adaptation in the Non-structural protein 1 (with a wild-type Envelope protein), allowing for the use of a single virus/viral genome system for vaccine production. The present disclosure is also directed, at least in part, to a Zika virus clonal isolate that is genetically homogenous and/or has been purified away from one or more adventitious agents. Accordingly, the present disclosure provides vaccines and immunogenic compositions useful for treating and/or preventing Zika virus infection (e.g., in humans) that include one or more Zika virus antigens (e.g., one or more antigens from a whole inactivated Zika virus) from a Zika virus harboring at least one non-human cell adaptation mutation (e.g., a mutation in Zika virus Non-structural protein 1) and/or a Zika virus clonal isolate.

The present disclosure is based, at least in part, on the surprising finding that both high and low dose vaccines comprising one or more antigens from separately derived clonal virus populations of non-human cell adapted Zika virus were able to induce robust immune responses and provide significant protection from Zika virus infection (See Example 2 below). Clonal isolation of the Zika virus strains also allowed for: 1) the successful purification of the virus away from contaminating agents (e.g., adventitious agents that may be co-purified with the parental strain), and 2) the production of a genetically homogeneous viral population. Moreover, the present disclosure is based, at least in part, on the finding that clonal isolated Zika viruses harboring an adaptation mutation in protein NS1 grew well and predictably in Vero cells to high titer, and surprisingly, were genetically stable/genetically homogenous without any detectable mutations to in the viral envelope protein (See Examples 1 and 2 below). While a similar mutation in Zika virus Non-structural protein 1 may have been observed in the genomic sequencing analysis of 1 out of 3 published sequences of Zika virus strain PRVABC59 (Yun et al. Genome Announc. 2016 Aug. 18; 4(4)), this reference fails to teach or suggest that a mutation in NS1 may improve stability of the virus; fails to teach or suggest that a virus harboring the mutation may be used in the development of an effective vaccine against Zika virus; and fails to teach or suggest that such a vaccine may be effective in inducing a robust immune response and providing significant protection from Zika virus infection when used at both low and high doses. Thus, without wishing to be bound by theory, the inventors of the present disclosure have determined that the adaptation mutation in protein NS1 appeared to enhance genetic stability within the Zika virus, resulting in increased/enhanced replication efficiency. Further, the Zika strain harboring an adaptation mutation in protein NS1 was able to be passaged multiple times without developing further mutations. Such a stable Zika virus strain is advantageous as a master virus seed (MVS), or subsequent seeds derived from the MVS, for vaccine production and manufacturing, as the risk of the master virus seed developing undesirable mutations is reduced. Moreover, without wishing to be bound by theory, the adaptation mutation in protein NS1 of the Zika strain of the present disclosure may also reduce or otherwise inhibit the occurrence of undesirable mutations, such as a mutation within the envelope protein E (Env) of the Zika virus strain.

Accordingly, certain aspects of the present disclosure relate to a vaccine or immunogenic composition containing one or more antigen from a Zika virus, where the Zika virus contains at least one non-human cell adaptation mutation. In some embodiments, the at least one non-human cell adaptation mutation is in Zika virus Non-structural protein 1 (NS1). In some embodiments, the at least one adaptation mutation occurs at position 98 of SEQ ID NO: 1, or at a position corresponding to position 98 of SEQ ID NO: 1. In some embodiments, the at least one adaptation mutation is a Trp98Gly mutation.

In some embodiments that may be combined with any of the preceding embodiments, the at least one adaptation mutation enhances genetic stability as compared to a Zika virus lacking the at least one adaptation mutation. In some embodiments that may be combined with any of the preceding embodiments, the at least one adaptation mutation enhances viral replication as compared to a Zika virus lacking the at least one adaptation mutation. In some embodiments that may be combined with any of the preceding embodiments, the Zika virus does not comprise a mutation in Envelope protein E (Env).

In some embodiments that may be combined with any of the preceding embodiments, the non-human cell is a mammalian cell. In some embodiments that may be combined with any of the preceding embodiments, the non-human cell is a monkey cell. In some embodiments, the monkey cell is from a Vero cell line. In some embodiments, the Vero cell line is a WHO Vero 10-87 cell line.

In some embodiments that may be combined with any of the preceding embodiments, the Zika virus is an African lineage virus or an Asian lineage virus. In some embodiments, the Zika virus is an Asian lineage virus. In some embodiments, the Zika virus is from strain PRVABC59.

In some embodiments that may be combined with any of the preceding embodiments, the vaccine or immunogenic composition is a purified antigen vaccine or immunogenic composition, a subunit vaccine or immunogenic composition, an inactivated whole virus vaccine or immunogenic composition, or an attenuated virus vaccine or immunogenic composition. In some embodiments, the vaccine or immunogenic composition is an inactivated whole virus vaccine or immunogenic composition. In some embodiments, the vaccine or immunogenic composition comprises a purified inactivated whole Zika virus. In some embodiments, the vaccine or immunogenic composition comprises a purified inactivated whole Zika virus comprising a mutation at position 98 of SEQ ID NO: 1, or at a position corresponding to position 98 of SEQ ID NO: 1. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO: 1. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59 comprising the genomic sequence according to SEQ ID NO:2. In some embodiments, the vaccine or immunogenic composition comprises a purified inactivated whole Zika which differs from strain PRVABC59 in a Trp98Gly mutation at position 98 of SEQ ID NO: 1.

In some embodiments that may be combined with any of the preceding embodiments, the virus was chemically inactivated. In some embodiments, the virus was chemically inactivated with one or more of a detergent, formalin, hydrogen peroxide, beta-propiolactone (BPL), binary ethylamine (BEI), acetyl ethyleneimine, methylene blue, and psoralen. In some embodiments, the virus was chemically inactivated with formalin.

In some embodiments that may be combined with any of the preceding embodiments, the vaccine or immunogenic composition further contains an adjuvant. In some embodiments, the adjuvant is selected from aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and/or Incomplete Freund's Adjuvant (IFA). In some embodiments, the adjuvant is an aluminum salt. In some embodiments, the adjuvant is selected from the group consisting of alum, aluminum phosphate, aluminum hydroxide, potassium aluminum sulfate, and Alhydrogel 85. In some embodiments, at least 75%, at least 85%, at least 90%, at least 95%, at least 96%, at least 97%, at least 98%, at least 99%, or 100% of the one or more antigens are adsorbed to the adjuvant.

In some embodiments that may be combined with any of the preceding embodiments, the vaccine or immunogenic composition is a low dose vaccine or immunogenic composition (e.g., containing from about 1 µg to about 5 µg antigen). In some embodiments that may be combined with any of the preceding embodiments, the vaccine or immunogenic composition is a high dose vaccine or immunogenic composition (e.g., containing about 10 µg antigen). In some embodiments that may be combined with any of the preceding embodiments, the vaccine or immunogenic composition contains from about 0.1 µg to about 25 µg of the one or more antigens. In certain such embodiments the antigen is a purified inactivated whole virus, such as a Zika virus with a mutation which is a tryptophan to glycine substitution at position 98 of SEQ ID NO:1 or at a position corresponding to position 98 of SEQ ID NO: 1 as described herein. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59 comprising the genomic sequence according to SEQ ID NO:2. In certain such embodiments the Zika virus is a plaque purified clonal Zika virus isolate. In some embodiments that may be combined with any of the preceding embodiments, the vaccine or immunogenic composition contains from about 0.1 µg Zika virus or Env to about 100 µg Zika virus or Env. In some embodiments, the vaccine or immunogenic composition is unadjuvanted. In some embodiments that may be combined with any of the preceding embodiments, the Zika virus is a clonal isolate. In some embodiments, the clonal isolate is substantially free of one or more adventitious agents (e.g., free of one or more adventitious agents that may be co-purified with the parental strain).

Other aspects of the present disclosure relate to a vaccine comprising a Zika virus having a mutation at position 98 of SEQ ID NO: 1, or at a position corresponding to position 98 of SEQ ID NO: 1. In some embodiments, the vaccine comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59. In some embodiments, the vaccine Comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59 comprising the genomic sequence according to SEQ ID NO:2. In certain such embodiments the Zika virus is a plaque purified clonal Zika virus isolate.

Other aspects of the present disclosure relate to a vaccine or immunogenic composition containing: a) an aluminum salt adjuvant; and b) a purified inactivated whole Zika virus, where the Zika virus contains a non-human cell adaptation mutation, and where the non-human cell adaptation mutation is a Trp98Gly mutation at position 98 of SEQ ID NO: 1, or at a position corresponding to position 98 of SEQ ID NO: 1.

Other aspects of the present disclosure relate to a method of treating or preventing Zika virus infection in a subject in need thereof, including administering to the subject a therapeutically effective amount of any of the vaccines or immunogenic compositions described herein.

Other aspects of the present disclosure relate to a method for inducing an immune response in a subject in need thereof, including administering to the subject an immunogenic amount of any of the vaccines or immunogenic compositions described herein. In some embodiments that may be combined with any of the preceding embodiments, the subject is a human. In some embodiments, the subject is pregnant or intends to become pregnant.

In some embodiments that may be combined with any of the preceding embodiments, administration of the vaccine or immunogenic composition induces a protective immune response in the subject. In some embodiments, the protective immune response induced in the subject is greater than a protective immune response induced in a corresponding subject administered a vaccine or immunogenic composition containing one or more antigens from a Zika virus lacking the at least one non-human cell adaptation mutation. In some embodiments that may be combined with any of the preceding embodiments, administration of the vaccine or immunogenic composition induces the generation of neutralizing antibodies to Zika virus in the subject. In some embodiments, the concentration of neutralizing antibodies generated in the subject is higher than a concentration of neutralizing antibodies generated in a corresponding subject administered a vaccine or immunogenic composition comprising one or more antigens from a Zika virus lacking the at least one non-human cell adaptation mutation.

In some embodiments that may be combined with any of the preceding embodiments, the vaccine or immunogenic composition is administered by a route selected from subcutaneous administration, transcutaneous administration, intradermal administration, subdermal administration, intramuscular administration, peroral administration, intranasal administration, buccal administration, intraperitoneal administration, intravaginal administration, anal administration and/or intracranial administration. In some embodiments that may be combined with any of the preceding embodiments, the vaccine or immunogenic composition is administered one or more times. In some embodiments, the vaccine or immunogenic composition is administered as a first (prime) and a second (boost) administration. In some embodiments, the second (boost) administration is administered at least 28 days after the first (prime) administration.

Other aspects of the present disclosure relate to a method for inactivating a Zika virus preparation, including (a) isolating the Zika virus preparation from one or more non-human cells, where the cells are used to produce the virus preparation, and where the Zika virus contains at least one non-human cell adaptation mutation; and (b) treating the virus preparation with an effective amount of formalin. In some embodiments, the method further includes (c) neutralizing the formalin-treated virus preparation with sodium metabisulfite. In some embodiments, the virus preparation is neutralized at least five, at least seven, at least nine, at least 11, or at least 14 days after formalin treatment. In some embodiments, the method further includes (d) purifying the neutralized virus preparation. In some embodiments, the neutralized virus preparation is purified by a process selected from cross flow filtration (CFF), multimodal chromatography, size exclusion chromatography, cation exchange chromatography, and/or anion exchange chromatography.

Other aspects of the present disclosure relate to a method for inactivating a Zika virus preparation, including (a) isolating the Zika virus preparation from one or more non-human cells, wherein the cells are used to produce the virus preparation, and wherein the Zika virus comprises a mutation at position 98 of SEQ ID NO: 1, or at a position corresponding to position 98 of SEQ ID NO: 1; and (b) treating the virus preparation with an effective amount of formalin. In some embodiments, the method further includes (c) neutralizing the formalin-treated virus preparation with sodium metabisulfite. In some embodiments, the virus preparation is neutralized at least five, at least seven, at least nine, at least 11, or at least 14 days after formalin treatment. In some embodiments, the method further includes (d) purifying the neutralized virus preparation. In some embodiments, the neutralized virus preparation is purified by process selected from cross flow filtration (CFF), multimodal chromatography, size exclusion chromatography, cation exchange chromatography, and/or anion exchange chromatography.

In some embodiments that may be combined with any of the preceding embodiments, the virus preparation is mixed with an adjuvant. In some embodiments, the adjuvant is selected from aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly (lactide-co-glycolides) (PLG) microparticles, poloxamer particles, microparticles, liposomes, Complete Freund's Adjuvant (CFA), and/or Incomplete Freund's Adjuvant (IFA). In some embodiments, the adjuvant is an aluminum salt. In some embodiments, the adjuvant is selected from alum, aluminum phosphate, aluminum hydroxide, potassium aluminum sulfate, and/or Alhydrogel 85. In some embodiments, at least 75%, at least 85%, at least 90%, at least 95%, at least 96%, at least 97%, at least 98%, at least 99%, or 100% of one or more antigens in the virus preparation are adsorbed to the adjuvant.

In some embodiments that may be combined with any of the preceding embodiments, the at least one non-human cell adaptation mutation is in Zika virus NS1. In some embodiments, the at least one adaptation mutation occurs at position 98 of SEQ ID NO: 1, or at a position corresponding to position 98 of SEQ ID NO: 1. In some embodiments, the at least one adaptation mutation is a Trp98Gly mutation. In some embodiments that may be combined with any of the preceding embodiments, the at least one adaptation mutation enhances genetic stability as compared to a Zika virus lacking the at least one adaptation mutation. In some embodiments that may be combined with any of the preceding embodiments, the at least one adaptation mutation enhances viral replication as compared to a Zika virus lacking the at least one adaptation mutation. In some embodiments that may be combined with any of the preceding embodiments, the Zika virus does not comprise a mutation in Envelope protein E (Env).

Other aspects of the present disclosure relate to a method of purifying Zika virus, including the steps: (a) inoculating a plurality of cells with an inoculum containing a population of Zika viruses, and (b) obtaining a Zika virus clonal isolate by plaque purification from one or more of the inoculated cells. In some embodiments, the cells are non-human cells. In some embodiments, the cells are insect cells. In some embodiments, the cells are mosquito cells. In some embodiments, the cells are mammalian cells. In some embodiments, the mammalian cells are monkey cells. In come embodiments, the monkey cells are from a Vero cell line. In some embodiments, the Vero cell line is a WHO Vero 10-87 cell line.

In some embodiments that may be combined with any of the preceding embodiments, the population of Zika viruses is heterogeneous. In some embodiments that may be combined with any of the preceding embodiments, the population of Zika viruses comprises a Zika virus clinical isolate. In some embodiments, the Zika virus clinical isolate is from strain PRVABC59. In some embodiments that may be combined with any of the preceding embodiments, the population of Zika viruses comprises a Zika virus that has been previously passaged one or more times in cell culture. In some embodiments that may be combined with any of the preceding embodiments, the inoculum comprises human serum. In some embodiments that may be combined with any of the preceding embodiments, the inoculum comprises one or more adventitious agents. In some embodiments, the Zika virus clonal isolate is substantially free of the one or more adventitious agents.

In some embodiments that may be combined with any of the preceding embodiments, the methods further include one or more additional plaque purifications of the Zika virus clonal isolate. In some embodiments, the Zika virus clonal isolate is further plaque purified two or more times. In some embodiments that may be combined with any of the preceding embodiments, the methods further include passaging the Zika virus clonal isolate one or more times in cell culture. In some embodiments, the Zika virus clonal isolate is passaged two or more times.

In some embodiments that may be combined with any of the preceding embodiments, the methods further include formulating a vaccine or immunogenic composition comprising one or more antigens from the Zika virus clonal isolate. In some embodiments, the vaccine or immunogenic composition is a purified antigen vaccine or immunogenic composition, a subunit vaccine or immunogenic composition, an inactivated whole virus vaccine or immunogenic composition, or an attenuated virus vaccine or immunogenic composition. In some embodiments, the vaccine or immunogenic composition is a purified inactivated whole virus vaccine or immunogenic composition. In some embodiments, the Zika virus clonal isolate was chemically inactivated. In some embodiments, the Zika virus clonal isolate was chemically inactivated with one or more of a detergent, formalin, hydrogen peroxide, beta-propiolactone (BPL), binary ethylamine (BEI), acetyl ethyleneimine, methylene blue, and psoralen. In some embodiments, the Zika virus clonal isolate was chemically inactivated with formalin.

In some embodiments that may be combined with any of the preceding embodiments, the methods further include admixing the vaccine or immunogenic composition with an adjuvant. In some embodiments, the adjuvant is selected from aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA). In some embodiments, the adjuvant is an aluminum salt. In some embodiments, the adjuvant is selected from alum, aluminum phosphate, aluminum hydroxide, potassium aluminum sulfate, and Alhydrogel 85. In some embodiments, at least 75%, at least 85%, at least 90%, at least 95%, at least 96%, at least 97%, at least 98%, at least 99%, or 100% of the one or more antigens are adsorbed to the adjuvant. In some embodiments that may be combined with any of the preceding embodiments, the vaccine or immunogenic composition comprises from about 0.1 μg Env to about 100 μg Env. In certain such embodiments the Zika virus is a plaque purified clonal Zika virus isolate. In some embodiments, the vaccine or immunogenic composition is unadjuvanted.

In some embodiments that may be combined with any of the preceding embodiments, the Zika virus clonal isolate is a homogenous genetic population. In some embodiments, the Zika virus clonal isolate does not contain a mutation in Envelope protein E (Env). In some embodiments, the Zika virus clonal isolate contains at least one mutation. In some embodiments, the at least one mutation is in Zika virus Non-structural protein 1 (NS1). In some embodiments, the at least one mutation occurs at position 98 of SEQ ID NO: 1, or at a position corresponding to position 98 of SEQ ID NO: 1. In some embodiments, the at least one mutation is a Trp98Gly mutation. In some embodiments the at least one mutation is not in Envelope protein E (Env). In some embodiments, the at least one mutation enhances genetic stability as compared to a Zika virus lacking the at least one mutation. In some embodiments, the at least one mutation enhances viral replication as compared to a Zika virus lacking the at least one mutation.

Other aspects of the present disclosure relate to a method of purifying Zika virus for the preparation of a vaccine or immunogenic composition, including one or more (e.g., one or more, two or more, three or more, four or more, five or more, or all six) steps selected from: (a) passing a sample containing a Zika virus through a depth filter to produce an eluate, where the eluate contains the Zika virus; (b) buffer exchanging and/or diluting a sample containing a Zika virus by cross flow filtration (CFF) to produce a retentate, where the retentate contains the Zika virus; (c) binding a sample containing a Zika virus to an ion exchange membrane to produce a bound fraction, where the bound fraction contains the Zika virus, and eluting the bound fraction from the ion exchange membrane; (d) treating a sample containing a Zika virus with an effective amount of a chemical inactivator; (e) neutralizing a sample containing a chemically inactivated Zika virus with sodium metabisulfite; and/or (f) purifying a naturalized sample containing a chemically inactivated Zika virus by cross flow filtration (CFF). In some embodiments, the method includes all of the steps of: (a) passing a sample containing a Zika virus through a depth filter to produce an eluate, where the eluate contains the Zika virus; (b) buffer exchanging and/or diluting a sample containing a Zika virus by cross flow filtration (CFF) to produce a retentate, where the retentate contains the Zika virus; (c) binding a sample containing a Zika virus to an ion exchange membrane to produce a bound fraction, where the bound fraction contains the Zika virus, and eluting the bound fraction from the ion exchange membrane; (d) treating a sample containing a Zika virus with an effective amount of a chemical inactivator; (e) neutralizing a sample containing a chemically inactivated Zika virus with sodium metabisulfite; and/or (f) purifying a naturalized sample containing a chemically inactivated Zika virus by cross flow filtration (CFF), in any order. In some embodiments, the method includes the steps of: (a) passing a sample containing a Zika virus through a first depth filter to produce a first eluate, where the first eluate containing the Zika virus; (b) buffer exchanging and/or diluting the first eluate by cross flow filtration (CFF) to produce a first retentate, where the first retentate contains the Zika virus; (c) binding the first retentate to an ion exchange membrane to produce a first bound fraction, where the first bound fraction contains the Zika virus, and eluting the first bound fraction from the ion exchange membrane to produce a second eluate, where the second eluate contains the Zika virus; (d) passing the second eluate through a second depth filter to produce a second retentate, where the second retentate contains the Zika virus; (e) treating the second retentate with an effective amount of a chemical inactivator; (f) neutralizing the treated second retentate with sodium metabisulfite; and (g) purifying the neutralized second retentate by cross flow filtration (CFF). In some embodiments that may be combined with any of the preceding embodiments, the ion exchange membrane is an anion exchange membrane. In some embodiments that may be combined with any of the preceding embodiments, the anion exchange membrane comprises quaternary ammonium ligands.

In some embodiments that may be combined with any of the preceding embodiments, the bound fraction of step (c) is eluted in multiple steps, where each step includes an increasing salt concentration. In some embodiments that may be combined with any of the preceding embodiments, the salt is sodium chloride. In some embodiments that may be combined with any of the preceding embodiments, the salt concentration increases from 250 mM to 750 mM. In some embodiments that may be combined with any of the preceding embodiments, the chemical inactivator is one or more of a detergent, formalin, hydrogen peroxide, beta-propiolactone (BPL), binary ethylamine (BEI), acetyl ethyleneimine, methylene blue, and psoralen. In some embodiments that may be combined with any of the preceding embodiments, the chemical inactivator is formalin. In some embodiments that may be combined with any of the preceding embodiments, the neutralization occurs for at least five, at least seven, at least nine, at least 11, or at least 14 days. In some embodiments that may be combined with any of the preceding embodiments, the Zika virus is a Zika virus clonal isolate produced by any of the methods described herein.

Other aspects of the present disclosure relate to a vaccine or immunogenic composition containing one or more antigens from a plaque purified clonal Zika virus isolate. In some embodiments, the plaque purified clonal Zika virus isolate was plaque purified from cells contacted with an inoculum comprising a population of Zika viruses. In some embodiments, the cells are non-human cells. In some embodiments, the cells are insect cells. In some embodiments, the insect cells are mosquito cells. In some embodiments, the cells are mammalian cells. In some embodiments, the mammalian cells are monkey cells. In some embodiments, the monkey cells are from a Vero cell line. In some embodiments, the Vero cell line is a WHO Vero 10-87 cell line.

In some embodiments that may be combined with any of the preceding embodiments, the population of Zika viruses was heterogeneous. In some embodiments that may be combined with any of the preceding embodiments, the population of Zika viruses comprised a Zika virus clinical isolate. In some embodiments, the Zika virus clinical isolate is from strain PRVABC59. In some embodiments that may be combined with any of the preceding embodiments, the population of Zika viruses comprised a Zika virus that had been previously passaged one or more times in cell culture. In some embodiments that may be combined with any of the preceding embodiments, the inoculum comprised human serum. In some embodiments that may be combined with any of the preceding embodiments, the inoculum comprised one or more adventitious agents. In some embodiments, the plaque purified clonal Zika virus isolate is substantially free of the one or more adventitious agents.

In some embodiments that may be combined with any of the preceding embodiments, the plaque purified clonal Zika virus isolate is modified as compared to a wild-type Zika virus. In some embodiments that may be combined with any of the preceding embodiments, the plaque purified clonal Zika virus isolate is a homogenous genetic population. In some embodiments that may be combined with any of the preceding embodiments, the plaque purified clonal Zika virus isolate does not include a mutation in Envelope protein E (Env). In some embodiments that may be combined with any of the preceding embodiments, the plaque purified clonal Zika virus isolate comprises at least one mutation. In some embodiments, the at least one mutation is in Zika virus Non-structural protein 1 (NS1). In some embodiments, the at least one mutation occurs at position 98 of SEQ ID NO: 1, or at a position corresponding to position 98 of SEQ ID NO: 1. In some embodiments, the at least one mutation is a Trp98Gly mutation. In some embodiments, the at least one mutation is not in Zika virus Envelope protein E (Env). In some embodiments, the at least one mutation enhances genetic stability as compared to a Zika virus lacking the at least one mutation. In some embodiments, the at least one mutation enhances viral replication as compared to a Zika virus lacking the at least one mutation. In some embodiments that may be combined with any of the preceding embodiments, the plaque purified clonal Zika virus isolate is an African lineage virus or an Asian lineage virus. In some embodiments, the plaque purified clonal Zika virus isolate is an Asian lineage virus.

In some embodiments that may be combined with any of the preceding embodiments, the vaccine or immunogenic composition is a purified antigen vaccine or immunogenic composition, a subunit vaccine or immunogenic composition, an inactivated whole virus vaccine or immunogenic composition, or an attenuated virus vaccine or immunogenic composition. In some embodiments, the vaccine or immunogenic composition is an inactivated whole virus vaccine or immunogenic composition. In some embodiments that may be combined with any of the preceding embodiments, the plaque purified clonal Zika virus isolate was chemically inactivated. In some embodiments, the plaque purified Zika virus was chemically inactivated with one or more of a detergent, formalin, hydrogen peroxide, beta-propiolactone (BPL), binary ethylamine (BEI), acetyl ethyleneimine, methylene blue, and psoralen. In some embodiments, the plaque purified clonal Zika virus isolate was chemically inactivated with formalin.

In some embodiments that may be combined with any of the preceding embodiments, the vaccine or immunogenic composition further comprises an adjuvant. In some embodiments, the adjuvant is selected from aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA). In some embodiments, the adjuvant is an aluminum salt. In some embodiments, the adjuvant is selected from alum, aluminum phosphate, aluminum hydroxide, potassium aluminum sulfate, and Alhydrogel 85. In some embodiments, at least 75%, at least 85%, at least 90%, at least 95%, at least 96%, at least 97%, at least 98%, at least 99%, or 100% of the one or more antigens are adsorbed to the adjuvant. In some embodiments that may be combined with any of the preceding embodiments, the vaccine or immunogenic composition contains from about 0.1 µg Env to about 100 µg Env. In certain such embodiments the Zika virus is a plaque purified clonal Zika virus isolate. In some embodiments, the vaccine or immunogenic composition is unadjuvanted.

It is to be understood that one, some, or all of the properties of the various embodiments described above and herein may be combined to form other embodiments of the present disclosure. These and other aspects of the present disclosure will become apparent to one of skill in the art. These and other embodiments of the present disclosure are further described by the detailed description that follows.

BRIEF DESCRIPTION OF THE DRAWINGS

FIG. 6 shows an amino acid sequence alignment comparing the envelope glycoprotein sequence of Zika virus near residue 330 from Zika virus strains PRVABC59 P6e (SEQ ID NO: 8) and PRVABC59 (SEQ ID NO: 9) with several other flaviviruses (WNV (SEQ ID NO: 10); JEV (SEQ ID NO: 11); SLEV (SEQ ID NO: 12); YFV (SEQ ID NO: 13); DENV 1 16007 (SEQ ID NO: 14); DENV 2 16681 (SEQ ID NO: 15); DENV 3 16562 (SEQ IDNO: 16); and DENV 4 1036 (SEQ ID NO: 17)).

FIG. 7 shows an amino acid sequence alignment comparing the NS1 protein sequence of Zika virus near residue 98 from Zika virus strains PRVABC59 P6e (SEQ ID NO: 18) and PRVABC59 (SEQ ID NO: 19) with several other flaviviruses (WNV (SEQ ID NO: 20); JEV (SEQ ID NO: 21); SLEV (SEQ ID NO: 22); YFV (SEQ ID NO: 23); DENV 1 16007 (SEQ ID NO: 24); DENV 2 16681 (SEQ ID NO: 25); DENV 3 16562 (SEQ IDNO: 26); and DENV 4 1036 (SEQ ID NO: 27)).

FIG. 12A shows the schedule of dosing of CD-1 mice with vaccine formulations derived from the ZIKAV PRVABC59 P6b and P6e clones. PBS was used as placebo.

FIG. 12B shows the serum ZIKAV neutralizing antibody titers of CD-1 mice immunized as described in FIG. 12A using vaccine formulations derived from ZIKAV PRVABC59 P6b and P6e clones. ZIKAV neutralizing antibody titers were determined by Reporter Virus Particle (RVP) neutralization assay. Solid lines represent the geometric mean of a group. The limit of detection (1.93 $\log_{10}$) is represented by a dashed line.

FIG. 13A shows the schedule of dosing of AG129 mice with vaccine formulations derived from the ZIKAV PRV-ABC59 P6b and P6e clones. PBS was used as a placebo.

FIG. 13B shows the serum ZIKAV neutralizing antibody titers of AG129 mice immunized as described in FIG. 13A using vaccine formulations derived from ZIKAV PRV-ABC59 P6b and P6e clones. Solid lines represent the geometric mean of a group. The limit of detection (1.30 $\log_{10}$) is represented by a dashed line. Animals with no detectable titer (<1.30) were assigned a titer of 0.5.

FIG. 21 shows the correlation between ZIKAV neutralizing antibody titers and viremia observed in passive transfer mice.

FIG. 25 shows a summary of the Clinical Study Design for Example 4.

DETAILED DESCRIPTION

General Techniques

Figure 1:
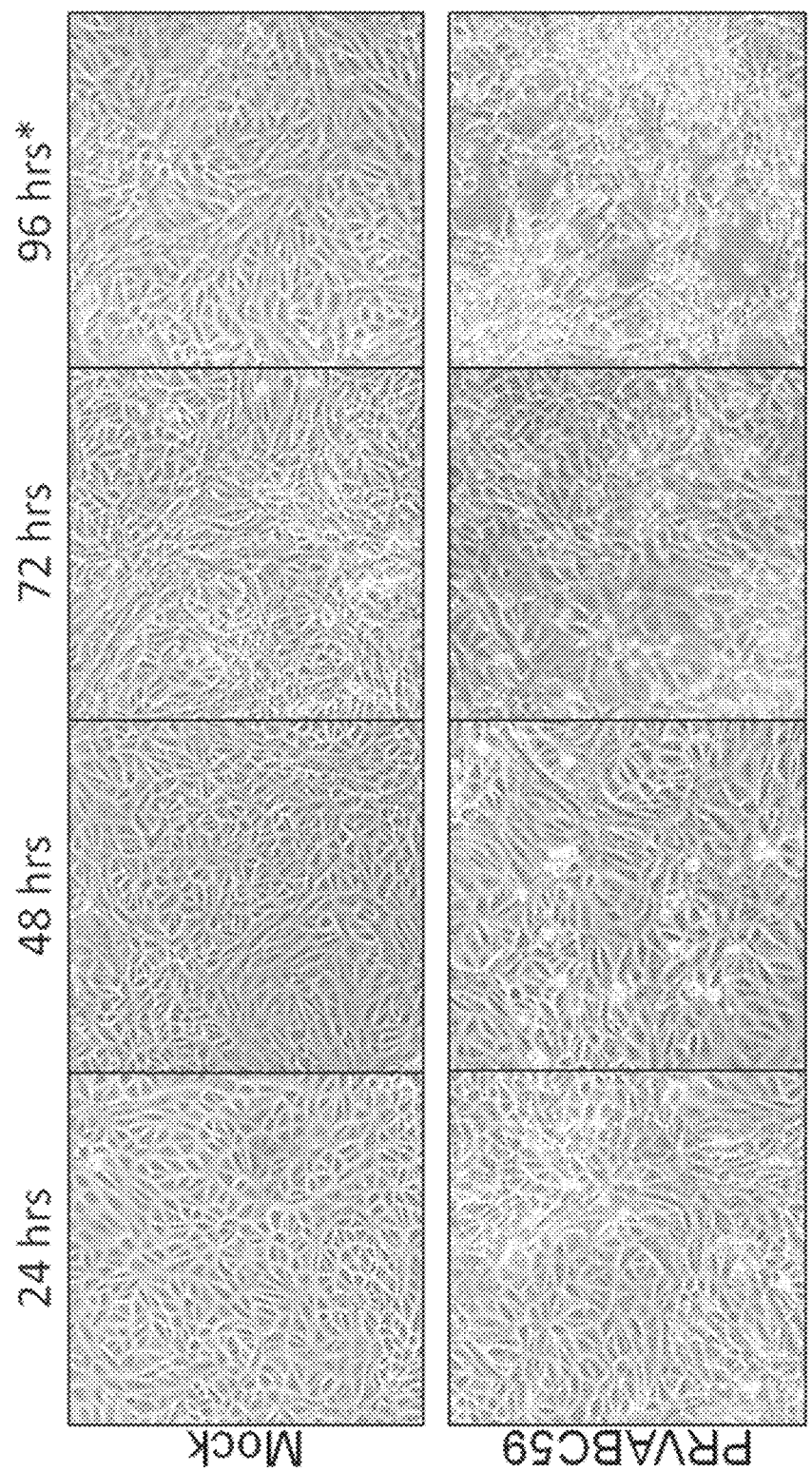
FIG. 1 shows bright field microscopy images of Vero cell monolayers mock infected (top) or infected with ZIKAV strain PRVABC59 (bottom).

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), *Antibodies, A Laboratory Manual* (Harlow and Lane, eds. (1988), and *Animal Cell Culture* (R. I. Freshney, ed. (1987)); *Oligonucleotide Synthesis* (M. J. Gait, ed., 1984); *Methods in Molecular Biology* (J. M. Walker, ed. Humana Press (1983)); *Cell Biology: A Laboratory Notebook* (J. E. Celis, ed., Academic Press (1998)) Academic Press; *Animal Cell Culture* (RI. Freshney), ed., 1987); *Introduction to Cell and Tissue Culture* (J. P. Mather and P. E. Roberts, eds. Plenum Press (1998)); *Cell and Tissue Culture: Laboratory Procedures* (A. Doyle, J. B. Griffiths, and D. G. Newell, eds., J. Wiley and Sons (1993-8)); *Handbook of Experimental Immunology* (D. M. Weir and C. C. Blackwell, eds.); *Gene Transfer Vectors for Mammalian Cells* (J. M. Miller and M. P. Calos, eds., Cold Spring Harbor Laboratory (1987)); *PCR: The Polymerase Chain Reaction*, (Mullis et al., eds., Springer (1994)); *Current Protocols in Immunology* (J. E. Coligan et al., eds., Wiley (1991)); *Short Protocols in Molecular Biology* (Wiley and Sons, 1999); *Immunobiology* (C. A. Janeway and P. Travers, (1997)); *Antibodies* (P. Finch, 1997); *Antibodies: A Practical Approach* (D. Catty., ed., IRL Press, (1988-1989)); *Monoclonal Antibodies: A Practical Approach* (P. Shepherd and C. Dean, eds., Oxford University Press, (2000)); *Using Antibodies: A Laboratory Manual* (E. Harlow and D. Lane (Cold Spring Harbor Laboratory Press, (1999)); and *The Antibodies* (M. Zanetti and J. D. Capra, eds., Harwood Academic Publishers, (1995)).

Zika Virus

Certain aspects of the present disclosure relate to at least one Zika virus (e.g., a Zika virus clonal isolate, a Zika virus purified by the methods described herein, a Zika virus comprising one or more non-human cell adaptation mutations, etc.) that may be useful in vaccines and/or immunogenic compositions including, without limitation, purified viruses, inactivated viruses, attenuated viruses, recombinant viruses, or purified and/or recombinant viral proteins for subunit vaccines.

Zika virus (ZIKV) is a mosquito-borne flavivirus first isolated from a sentinel rhesus monkey in the Zika Forest in Uganda in 1947. Since that time, isolations have been made from humans in both Africa and Asia, and more recently, the Americas. ZIKV is found in two (possibly three) lineages: an African lineage (possibly separate East and West African lineages) and an Asian lineage. Accordingly, examples of suitable Zika viruses of the present disclosure include, without limitation, viruses from the African and/or Asian lineages. In some embodiments, the Zika virus is an African lineage virus. In some embodiments, the Zika virus is an Asian lineage virus. Additionally, multiple strains within the African and Asian lineages of Zika virus have been previously identified. Any one or more suitable strains of Zika virus known in the art may be used in the present disclosure, including, for examples, strains Mr 766, ArD 41519, IbH 30656, P6-740, EC Yap, FSS13025, ArD 7117, ArD 9957, ArD 30101, ArD 30156, ArD 30332, HD 78788, ArD 127707, ArD 127710, ArD 127984, ArD 127988, ArD 127994, ArD 128000, ArD 132912, 132915, ArD 141170, ArD 142623, ArD 149917, ArD 149810, ArD 149938, ArD 157995, ArD 158084, ArD 165522, ArD 165531, ArA 1465, ArA 27101, ArA 27290, ArA 27106, ArA 27096, ArA 27407, ArA 27433, ArA 506/96, ArA 975-99, Ara 982-99, ArA 986-99, ArA 2718, ArB 1362, Nigeria68, Malaysia66, Kedougou84, Suriname, MR1429, PRVABC59, ECMN2007, DakAr41524, H/PF/2013, R103451, 103344, 8375, JMB-185, ZIKV/H, sapiens/Brazil/Natal/2015, SPH2015, ZIKV/Hu/Chiba/S36/2016, and/or Cuba2017. In some embodiments, strain PRVABC59 is used in the present disclosure.

In some embodiments, an example of a Zika virus genome sequence is set forth below as SEQ ID NO: 2:

```
   1 gttgttgatc tgtgtgaatc agactgcgac agttcgagtt tgaagcgaaa gctagcaaca
  61 gtatcaacag gttttatttt ggatttggaa acgagagttt ctggtcatga aaacccaaa
 121 aaagaaatcc ggaggattcc ggattgtcaa tatgctaaaa cgcggagtag cccgtgtgag
 181 cccctttggg ggcttgaaga ggctgccagc cggacttctg ctgggtcatg ggcccatcag
 241 gatggtcttg gcgattctag ccttttgag attcacggca atcaagccat cactgggtct
 301 catcaataga tggggttcag tggggaaaaa agaggctatg gaaacaataa agaagttcaa
 361 gaaagatctg gctgccatgc tgagaataat caatgctagg aaggagaaga agagacgagg
 421 cgcagatact agtgtcggaa ttgttggcct cctgctgacc acagctatgg cagcggaggt
 481 cactagacgt gggagtgcat actatatgta cttggacaga aacgatgctg gggaggccat
 541 atcttttcca accacattgg ggatgaataa gtgttatata cagatcatgg atcttggaca
 601 catgtgtgat gccaccatga gctatgaatg ccctatgctg gatgaggggg tggaaccaga
 661 tgacgtcgat tgttggtgca acacgacgtc aacttgggtt gtgtacggaa cctgccatca
 721 caaaaaggt gaagcacgga gatctagaag agctgtgacg ctcccctccc attccaccag
 781 gaagctgcaa acgcggtcgc aaacctggtt ggaatcaaga gaatacacaa agcacttgat
 841 tagagtcgaa aattggatat tcaggaaccc tggcttcgcg ttagcagcag ctgccatcgc
 901 ttggcttttg ggaagctcaa cgagccaaaa agtcatatac ttggtcatga tactgctgat
 961 tgccccggca tacagcatca ggtgcatagg agtcagcaat agggactttg tggaaggtat
1021 gtcaggtggg acttgggttg atgttgtctt ggaacatgga ggttgtgtca ccgtaatggc
1081 acaggacaaa ccgactgtcg acatagagct ggttacaaca acagtcagca catggcgga
1141 ggtaagatcc tactgctatg aggcatcaat atcagacatg gcttctgaca gccgctgccc
1201 aacacaaggt gaagcctacc ttgacaagca atcagacact caatatgtct gcaaaagaac
1261 gttagtggac agaggctggg gaaatggatg tggactttt ggcaaaggga gcctggtgac
1321 atgcgctaag tttgcatgct ccaagaaaat gaccgggaag agcatccagc cagagaatct
1381 ggagtaccgg ataatgctgt cagttcatgg ctcccagcac agtgggatga tcgttaatga
1441 cacaggacat gaaactgatg agaatagagc gaaagttgag ataacgccca ttcaccgag
1501 agccgaagcc accctggggg ttttggaag cctaggactt gattgtgaac cgaggacagg
1561 ccttgacttt tcagatttgt attacttgac tatgaataac aagcactggt tggttcacaa
1621 ggagtggttc cacgacattc cattaccttg gcacgctggg gcagacaccg gaactccaca
1681 ctggaacaac aaagaagcac tggtagagtt caaggacgca catgccaaaa ggcaaactgt
1741 cgtggttcta gggagtcaag aaggagcagt tcacacggcc cttgctggag ctctggaggc
1801 tgagatggat ggtgcaaagg gaaggctgtc ctctggccac ttgaaatgtc gcctgaaaat
1861 ggataaactt agattgaagg gcgtgtcata ctccttgtgt actgcagcgt tcacattcac
1921 caagatcccg gctgaaacac tgcacgggac agtcacagtg gaggtacagt acgcagggac
1981 agatggacct tgcaaggttc cagctcagat ggcggtggac atgcaaactc tgaccccagt
2041 tgggaggttg ataaccgcta accccgtaat cactgaaagc actgagaact ctaagatgat
2101 gctggaactt gatccaccat ttggggactc ttacattgtc ataggagtcg gggagaagaa
2161 gatcacccac cactggcaca gagtggcag caccattgga aaagcatttg aagccactgt
```

-continued

```
2221  gagaggtgcc aagagaatgg cagtcttggg agacacagcc tgggactttg gatcagttgg
2281  aggcgctctc aactcattgg gcaagggcat ccatcaaatt tttggagcag ctttcaaatc
2341  attgtttgga ggaatgtcct ggttctcaca aattctcatt ggaacgttgc tgatgtggtt
2401  gggtctgaac acaaagaatg gatctatttc ccttatgtgc ttggccttag ggggagtgtt
2461  gatcttctta tccacagccg tctctgctga tgtggggtgc tcggtggact tctcaaagaa
2521  ggagacgaga tgcggtacag gggtgttcgt ctataacgac gttgaagcct ggagggacag
2581  gtacaagtac catcctgact cccccgtag attggcagca gcagtcaagc aagcctggga
2641  agatggtatc tgcgggatct cctctgtttc aagaatggaa acatcatgt ggagatcagt
2701  agaaggggag ctcaacgcaa tcctggaaga gaatggagtt caactgacgg tcgttgtggg
2761  atctgtaaaa aaccccatgt ggagaggtcc acagagattg cccgtgcctg tgaacgagct
2821  gccccacggc tggaaggctt gggggaaatc gtatttcgtc agagcagcaa agacaaataa
2881  cagctttgtc gtggatggtg acacactgaa ggaatgccca ctcaaacata gagcatggaa
2941  cagctttctt gtggaggatc atgggttcgg ggtatttcac actagtgtct ggctcaaggt
3001  tagagaagat tattcattag agtgtgatcc agccgttatt ggaacagctg ttaagggaaa
3061  ggaggctgta cacagtgatc taggctactg gattgagagt gagaagaatg acacatggag
3121  gctgaagagg gcccatctga tcgagatgaa acatgtgaa tggccaaagt cccacacatt
3181  gtggacagat ggaatagaag agagtgatct gatcataccc aagtctttag ctgggccact
3241  cagccatcac aataccagag agggctacag gacccaaatg aaagggccat ggcacagtga
3301  agagcttgaa attcggtttg aggaatgccc aggcactaag gtccacgtgg aggaaacatg
3361  tggaacaaga ggaccatctc tgagatcaac cactgcaagc ggaagggtga tcgaggaatg
3421  gtgctgcagg gagtgcacaa tgcccccact gtcgttccgg gctaaagatg gctgttggta
3481  tggaatggag ataaggccca ggaaagaacc agaaagcaac ttagtaaggt caatggtgac
3541  tgcaggatca actgatcaca tggaccactt ctcccttgga gtgcttgtga tcctgctcat
3601  ggtgcaggaa gggctgaaga agagaatgac cacaaagatc atcataagca catcaatggc
3661  agtgctggta gctatgatcc tgggaggatt ttcaatgagt gacctggcta agcttgcaat
3721  tttgatgggt gccaccttcg cggaaatgaa cactggagga gatgtagctc atctggcgct
3781  gatagcggca ttcaaagtca gaccagcgtt gctggtatct ttcatcttca gagctaattg
3841  gacaccccgt gaaagcatgc tgctggcctt ggcctcgtgt cttttgcaaa ctgcgatctc
3901  cgccttggaa ggcgacctga tggttctcat caatggtttt gctttggcct ggttggcaat
3961  acgagcgatg gttgttccac gcactgataa catcaccttg gcaatcctgg ctgctctgac
4021  accactggcc cggggcacac tgcttgtggc gtggagagca ggccttgcta cttgcggggg
4081  gtttatgctc ctctctctga agggaaaagg cagtgtgaag aagaacttac catttgtcat
4141  ggcccctggga ctaaccgctg tgaggctggt cgaccccatc aacgtggtgg gactgctgtt
4201  gctcacaagg agtgggaagc ggagctggcc ccctagcgaa gtactcacag ctgttggcct
4261  gatatgcgca ttggctggag ggttcgccaa ggcagatata gagatggctg ggcccatggc
4321  cgcggtcggt ctgctaattg tcagttacgt ggtctcagga aagagtgtgg acatgtacat
4381  tgaaagagca ggtgacatca catgggaaaa agatgcggaa gtcactggaa acagtccccg
4441  gctcgatgtg gcgctagatg agagtggtga tttctccctg gtggaggatg acggtccccc
4501  catgagagag atcatactca aggtggtcct gatgaccatc tgtggcatga acccaatagc
4561  cataccctt gcagctggag cgtggtacgt atacgtgaag actggaaaaa ggagtggtgc
```

-continued

```
4621 tctatgggat gtgcctgctc ccaaggaagt aaaaaagggg gagaccacag atggagtgta 4681 cagagtaatg actcgtagac tgctaggttc aacacaagtt ggagtgggag ttatgcaaga 4741 gggggtcttt cacactatgt ggcacgtcac aaaaggatcc gcgctgagaa gcggtgaagg 4801 gagacttgat ccatactggg gagatgtcaa gcaggatctg tgtcatact gtggtccatg 4861 gaagctagat gccgcctggg atgggcacag cgaggtgcag ctcttggccg tgcccccgg 4921 agagagagcg aggaacatcc agactctgcc cggaatattt aagacaaagg atggggacat 4981 tggagcggtt gcgctggatt acccagcagg aacttcagga tctccaatcc tagacaagtg 5041 tgggagagtg ataggacttt atggcaatgg ggtcgtgatc aaaaacggga gttatgttag 5101 tgccatcacc caagggagga gggaggaaga gactcctgtt gagtgcttcg agccctcgat 5161 gctgaagaag aagcagctaa ctgtcttaga cttgcatcct ggagctggga aaaccaggag 5221 agttcttcct gaaatagtcc gtgaagccat aaaaacaaga ctccgtactg tgatcttagc 5281 tccaaccagg gttgtcgctg ctgaaatgga ggaggccctt agagggcttc cagtgcgtta 5341 tatgacaaca gcagtcaatg tcacccactc tggaacagaa atcgtcgact taatgtgcca 5401 tgccaccttc acttcacgtc tactacagcc aatcagagtc cccaactata atctgtatat 5461 tatggatgag gcccacttca cagatccctc aagtatagca gcaagaggat acatttcaac 5521 aagggttgag atgggcgagg cggctgccat cttcatgacc gccacgccac caggaacccg 5581 tgacgcattt ccggactcca actcaccaat tatggacacc gaagtggaag tcccagagag 5641 agcctggagc tcaggctttg attgggtgac ggatcattct ggaaaaacag tttggtttgt 5701 tccaagcgtg aggaacggca atgagatcgc agcttgtctg acaaaggctg aaaacgggt 5761 catacagctc agcagaaaga cttttgagac agagttccag aaaacaaaac atcaagagtg 5821 ggacttttgtc gtgacaactg acatttcaga tgggcgcc aactttaaag ctgaccgtgt 5881 catagattcc aggagatgcc taaagccggt catacttgat ggcgagagag tcattctggc 5941 tggacccatg cctgtcacac atgccagcgc tgcccagagg aggggcgca taggcaggaa 6001 tcccaacaaa cctggagatg agtatctgta tggaggtggg tgcgcagaga ctgacgaaga 6061 ccatgcacac tggcttgaag caagaatgct ccttgacaat atttacctcc aagatggcct 6121 catagcctcg ctctatcgac ctgaggccga caaagtagca gccattgagg gagagttcaa 6181 gcttaggacg gagcaaagga agacctttgt ggaactcatg aaaagaggag atcttcctgt 6241 ttggctggcc tatcaggttg catctgccgg aataacctac acagatagaa gatggtgctt 6301 tgatggcacg accaacaaca ccataatgga agacagtgtg ccggcagagg tgtggaccag 6361 acacggagag aaaagagtgc tcaaaccgag gtggatggac gccagagttt gttcagatca 6421 tgcggccctg aagtcattca aggagtttgc cgctgggaaa agaggagcgg cttttggagt 6481 gatggaagcc ctgggaacac tgccaggaca catgacagag agattccagg aagccattga 6541 caacctcgct gtgctcatgc gggcagagac tggaagcagg ccttacaaag ccgcggcggc 6601 ccaattgccg gagaccctag agaccataat gctttgggg ttgctgggaa cagtctcgct 6661 gggaatcttc ttcgtcttga tgaggaacaa gggcataggg aagatgggct ttggaatggt 6721 gactcttggg gccagcgcat ggctcatgtg gctctcggaa attgagccag ccagaattgc 6781 atgtgtcctc attgttgtgt tcctattgct ggtggtgctc atacctgagc cagaaaagca 6841 aagatctccc caggacaacc aaatggcaat catcatcatg gtagcagtag tcttctgggg 6901 cttgattacc gccaatgaac tcggatggtt ggagagaaca aagagtgacc taagccatct 6961 aatgggaagg agagaggagg gggcaaccat aggattctca atggacattg acctgcggcc 7021 agcctcagct tgggccatct atgctgcctt gacaactttc attaccccag ccgtccaaca
```

-continued

```
7081  tgcagtgacc acctcataca acaactactc cttaatggcg atggccacgc aagctggagt
7141  gttgtttggc atgggcaaag ggatgccatt ctacgcatgg gactttggag tcccgctgct
7201  aatgataggt tgctactcac aattaacacc cctgacccta atagtggcca tcatttttgct
7261  cgtggcgcac tacatgtact tgatcccagg gctgcaggca gcagctgcgc gtgctgccca
7321  gaagagaacg gcagctggca tcatgaagaa ccctgttgtg gatggaatag tggtgactga
7381  cattgacaca atgacaattg accccccaagt ggagaaaaag atgggacagg tgctactcat
7441  agcagtagcc gtctccagcg ccatactgtc gcggaccgcc tgggggtggg gggaggctgg
7501  ggctctgatc acagccgcaa cttccacttt gtgggaaggc tctccgaaca agtactggaa
7561  ctcctctaca gccacttcac tgtgtaacat ttttagggga agttacttgg ctggagcttc
7621  tctaatctac acagtaacaa gaaacgctgg cttggtcaag agacgtgggg gtggaacagg
7681  agagaccctg ggagagaaat ggaaggcccg cttgaaccag atgtcggccc tggagttcta
7741  ctcctacaaa aagtcaggca tcaccgaggt gtgcagagaa gaggcccgcc gcgcccctcaa
7801  ggacggtgtg gcaacgggag gccatgctgt gtcccgagga agtgcaaagc tgagatggtt
7861  ggtggagcgg ggatacctgc agccctatgg aaaggtcatt gatcttggat gtggcagagg
7921  gggctggagt tactacgtcg ccaccatccg caaagttcaa gaagtgaaag gatacacaaa
7981  aggaggccct ggtcatgaag aacccgtgtt ggtgcaaagc tatggtgga acatagtccg
8041  tcttaagagt ggggtggacg tctttcatat ggcggctgag ccgtgtgaca cgttgctgtg
8101  tgacataggt gagtcatcat ctagtcctga agtggaagaa gcacggacgc tcagagtcct
8161  ctccatggtg ggggattggc ttgaaaaaag accaggagcc ttttgtataa aagtgttgtg
8221  cccatacacc agcactatga tggaaaccct ggagcgactg cagcgtaggt atggggagg
8281  actggtcaga gtgccactct cccgcaactc tacacatgag atgtactggg tctctggagc
8341  gaaaagcaac accataaaaa gtgtgtccac cacgagccag ctcctcttgg ggcgcatgga
8401  cgggcctagg aggccagtga aatatgagga ggatgtgaat ctcggctctg gcacgcgggc
8461  tgtggtaagc tgcgctgaag ctcccaacat gaagatcatt ggtaaccgca ttgaaaggat
8521  ccgcagtgag cacgcggaaa cgtggttctt tgacgagaac cacccatata ggacatgggc
8581  ttaccatgga agctatgagg cccccacaca agggtcagcg tcctctctaa taaacggggt
8641  tgtcaggctc ctgtcaaaac cctgggatgt ggtgactgga gtcacaggaa tagccatgac
8701  cgacaccaca ccgtatggtc agcaaagagt tttcaaggaa aaagtggaca ctagggtgcc
8761  agaccccccaa gaaggcactc gtcaggttat gagcatggtc tcttcctggt tgtggaaaga
8821  gctaggcaaa cacaaacggc cacgagtctg caccaaagaa gagttcatca acaaggttcg
8881  tagcaatgca gcattagggg caatatttga agaggaaaaa gagtggaaga ctgcagtgga
8941  agctgtgaac gatccaaggt tctgggctct agtggacaag gaaagagagc accacctgag
9001  aggagagtgc cagagctgtg tgtacaacat gatgggaaaa agagaaaaga acaagggga
9061  atttggaaag gccaagggca gccgcgccat ctggtatatg tggctagggg ctagatttct
9121  agagttcgaa gcccttggat tcttgaacga ggatcactgg atggggagag gaactcagg
9181  aggtggtgtt gaagggctgg gattacaaag actcggatat gtcctagaag agatgagtcg
9241  tataccagga ggaaggatgt atgcagatga cactgctggc tgggacaccc gcattagcag
9301  gtttgatctg gagaatgaag ctctaatcac caaccaaatg gagaaagggc acagggcctt
9361  ggcattggcc ataatcaagt acacatacca aaacaaagtg gtaaaggtcc ttagaccagc
9421  tgaaaaaggg aaaacagtta tggacattat ttcgagacaa gaccaaaggg ggagcggaca
```

```
-continued
9481 agttgtcact tacgctctta acacatttac caacctagtg gtgcaactca ttcggaatat 9541 ggaggctgag gaagttctag agatgcaaga cttgtggctg ctgcggaggt cagagaaagt 9601 gaccaactgg ttgcagagca acggatggga taggctcaaa cgaatggcag tcagtggaga 9661 tgattgcgtt gtgaagccaa ttgatgatag gtttgcacat gccctcaggt tcttgaatga 9721 tatgggaaaa gttaggaagg acacacaaga gtggaaaccc tcaactggat gggacaactg 9781 ggaagaagtt ccgttttgct cccaccactt caacaagctc catctcaagg acgggaggtc 9841 cattgtggtt ccctgccgcc accaagatga actgattggc cgggcccgcg tctctccagg 9901 ggcgggatgg agcatccggg agactgcttg cctagcaaaa tcatatgcgc aaatgtggca 9961 gctcctttat ttccacagaa gggacctccg actgatggcc aatgccattt gttcatctgt 10021 gccagttgac tgggttccaa ctgggagaac tacctggtca atccatggaa agggagaatg 10081 gatgaccact gaagacatgc ttgtggtgtg gaacagagtg tggattgagg agaacgacca 10141 catggaagac aagacccag ttacgaaatg gacagacatt ccctatttgg gaaaaaggga 10201 agacttgtgg tgtggatctc tcataggca cagaccgcgc accacctggg ctgagaacat 10261 taaaaacaca gtcaacatgg tgcgcaggat cataggtgat gaagaaaagt acatggacta 10321 cctatccacc caagttcgct acttgggtga agaagggtct acacctggag tgctgtaagc 10381 accaatctta atgttgtcag gcctgctagt cagccacagc ttggggaaag ctgtgcagcc 10441 tgtgaccccc ccaggagaag ctgggaaacc aagcctatag tcaggccgag aacgccatgg 10501 cacggaagaa gccatgctgc ctgtgagccc ctcagaggac actgagtcaa aaaacccac 10561 gcgcttggag gcgcaggatg ggaaaagaag gtggcgacct tccccacccct tcaatctggg 10621 gcctgaactg gagatcagct gtggatctcc agaagaggga ctagtggtta gagga
```

In some embodiments, the Zika virus may comprise the genome sequence of GenBank Accession number KU501215.1. In some embodiments, the Zika virus is from strain PRVABC59. In some embodiments the genome sequence of GenBank Accession number KU501215.1 comprises the sequence of SEQ ID NO: 2. In some embodiments, the Zika virus may comprise a genomic sequence that has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with the sequence of SEQ ID NO: 2.

In some embodiments, the Zika virus may comprise at least one polypeptide encoded by the sequence of SEQ ID NO: 2. In some embodiments, the Zika virus may comprise at least one polypeptide having an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with an amino acid sequence encoded by the sequence of SEQ ID NO: 2.

Accordingly, in some embodiments, Zika viruses of the present disclosure may be used in any of the vaccines and/or immunogenic compositions disclosed herein. For example, Zika viruses of the present disclosure may be used to provide one or more antigens useful for treating or preventing Zika virus infection in a subject in need thereof and/or for inducing an immune response, such as a protective immune response, against Zika virus in a subject in need thereof.

Viral Antigens

In some embodiments, the present disclosure relates to one or more antigens from any Zika virus described herein useful in vaccines and/or immunogenic compositions including, without limitation, purified viruses, inactivated viruses, attenuated viruses, recombinant viruses, or purified and/or recombinant viral proteins for subunit vaccines. In some embodiments, the vaccines and/or immunogenic compositions include purified inactivated whole viruses. In some embodiments the virus is a plaque purified clonal Zika virus isolate.

Antigens of the present disclosure may be any substance capable of eliciting an immune response. Examples of suitable antigens include, but are not limited to, whole virus, attenuated virus, inactivated virus, proteins, polypeptides (including active proteins and individual polypeptide epitopes within proteins), glycopolypeptides, lipopolypeptides, peptides, polysaccharides, polysaccharide conjugates, peptide and non-peptide mimics of polysaccharides and other molecules, small molecules, lipids, glycolipids, and carbohydrates.

Antigens of the present disclosure may be from any Zika virus (e.g., a Zika virus clonal isolate) produced from one or more cells in cell culture (e.g., via plaque purification). Any suitable cells known in the art for producing Zika virus may be used, including, for example, insect cells (e.g., mosquito cells such as CCL-125 cells, Aag-2 cells, RML-12 cells, C6/36 cells, C7-10 cells, AP-61 cells, A.t. GRIP-1 cells, A.t. GRIP-2 cells, A.t. GRIP-3 cells, UM-AVE1 cells, Mos.55 cells, SualB cells, 4a-3B cells, Mos.42 cells, MSQ43 cells, LSB-AA695BB cells, NIID-CTR cells, TRA-171, cells, and additional cells or cell lines from mosquito species such as *Aedes aegypti, Aedes albopictus, Aedes pseudoscutellaris,*

Aedes triseriatus, Aedes vexans, Anopheles gambiae, Anopheles stephensi, Anopheles albimus, Culex quinquefasciatus, Culex theileri, Culex tritaeniorhynchus, Culex bitaeniorhynchus, and/or Toxorhynchites amboinensis), and mammalian cells (e.g., VERO cells (from monkey kidneys), LLC-MK2 cells (from monkey kidneys), MDBK cells, MDCK cells, ATCC CCL34 MDCK (NBL2) cells, MDCK 33016 (deposit number DSM ACC 2219 as described in WO97/37001) cells, BHK21-F cells, HKCC cells, or Chinese hamster ovary cells (CHO cells). In some embodiments, antigens of the present disclosure are from a Zika virus (e.g., a Zika virus clonal isolate) produced from a non-human cell (e.g., via plaque purification). In some embodiments, antigens of the present disclosure are from a Zika virus (e.g., a Zika virus clonal isolate) produced from an insect cell (e.g., via plaque purification). In some embodiments, antigens of the present disclosure are from a Zika virus (e.g., a Zika virus clonal isolate) produced from a mosquito cell (e.g., via plaque purification). In some embodiments, antigens of the present disclosure are from a Zika virus (e.g., a Zika virus clonal isolate) produced from a mammalian cell (e.g., via plaque purification). In some embodiments, antigens of the present disclosure are from a Zika virus (e.g., a Zika virus clonal isolate) produced from a VERO cell (e.g., via plaque purification). Methods of purifying a virus by performing plaque purification are known to one of ordinary skill in the art (See e.g., Example 1 below).

Antigens of the present disclosure may include at least one non-human cell adaptation mutation. Adaptation mutations may be generated by adapting a virus to growth in a particular cell line. For example, a cell may be transfected or electroporated with a virus, RNA transcribed from a virus (e.g., an infectious virus, or infectious clone), and/or RNA purified from a whole virus and passaged such that the virus and/or viral RNA replicates and its nucleic acid mutates. Nucleic acid mutations may be point mutations, insertion mutations, or deletion mutations. Nucleic acid mutations may lead to amino acid changes within viral proteins that facilitate growth of the virus in a non-human cell. Adaptation mutations may facilitate phenotypic changes in the virus, including altered plaque size, growth kinetics, temperature sensitivity, drug resistance, virulence, and virus yield in cell culture. These adaptive mutations may be useful in vaccine manufacture by increasing the speed, yield, and consistency of virus cultured in a cell line. Adaptive mutations may change (e.g., enhance or decrease) immunogenicity of viral antigens by altering the structure of immunogenic epitopes. In addition, adaptive mutations may also increase the genetic stability of the virus and/or reduce or otherwise inhibit the development of undesirable mutations in the virus through multiple (e.g., at least five, at least six, at least seven, at least eight, at least nine, at least 10, at least 11, at least 12, at least 13, at least 14, at least 15, at least 16, at least 17, at least 18, at least 19, at least 20, or more) passages.

Accordingly, in certain embodiments, antigens of the present disclosure include at least one non-human cell adaptation mutation. In certain embodiments, the adaptation mutation is a mutation of a viral antigen to a non-human cell. In some embodiments, the non-human cell is a mammalian cell. Any suitable mammalian cell known in the art may be used, including, without limitation, VERO cells (from monkey kidneys), LLC-MK2 cells (from monkey kidneys), MDBK cells, MDCK cells, ATCC CCL34 MDCK (NBL2) cells, MDCK 33016 (deposit number DSM ACC 2219 as described in WO97/37001) cells, BHK21-F cells, HKCC cells, or Chinese hamster ovary cells (CHO cells). In some embodiments, the non-human cell is a monkey cell. In some embodiments, the monkey cell is from a Vero cell line. Any suitable Vero cell line known in the art may be used, including, without limitation, WHO Vero 10-87, ATCC CCL-81, Vero 76 (ATCC Accession No. CRL-1587), or Vero C1008 (ATCC Accession No. CRL-1586). In some embodiments, the Vero cell line is WHO Vero 10-87.

Zika viruses possess a positive sense, single-stranded RNA genome encoding both structural and nonstructural polypeptides. The genome also contains non-coding sequences at both the 5'- and 3'-terminal regions that play a role in virus replication. Structural polypeptides encoded by these viruses include, without limitation, capsid (C), precursor membrane (prM), and envelope (E). Non-structural (NS) polypeptides encoded by these viruses include, without limitation, NS1, NS2A, NS2B, NS3, NS4A, NS4B, and NS5.

In certain embodiments, antigens of the present disclosure may contain at least one (e.g., at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, etc.) non-human cell adaptation mutations within one or more (e.g., one or more, two or more, three or more, four or more, five or more, six or more, seven or more, eight or more, nine or more, or all ten) viral antigens/polypeptides, including, without limitation, C, prM, E, NS1, NS2A, NS2B, NS3, NS4A, NS4B, and NS5. In some embodiments, antigens of the present disclosure include at least one non-human cell adaptation mutation in Zika virus Non-structural protein 1 (NS1). In some embodiments, antigens of the present disclosure include whole, inactivated virus that may contain at least one (e.g., at least one, at least two, at least three, at least four, at least five, at least six, at least seven, at least eight, at least nine, at least 10, etc.) non-human cell adaptation mutations. In some embodiments, antigens of the present disclosure include whole, inactivated virus that may contain at least one non-human cell adaptation mutation in Zika virus Non-structural protein 1 (NS1). In some embodiments, antigens of the present disclosure include whole, inactivated viruses that may contain a Trp98Gly mutation at position 98 of SEQ ID NO: 1, or at a position corresponding to position 98 of SEQ ID NO:1.

In some embodiments, the at least one non-human cell adaptation mutation is within the NS1 polypeptide. The amino acid sequence of a wild-type, non-cell adapted NS1 polypeptide from an exemplary Zika virus strain is set forth as:

(SEQ ID NO: 1)
DVGCSVDFSKKETRCGTGVFVYNDVEAWRDRYKYHPDSPRRLAAAVKQAW

EDGICGISSVSRMENIMWRSVEGELNAILEENGVQLTVVVGSVKNPMWRG

PQRLPVPVNELPHGWKAWGKSYFVRAAKTNNSFVVDGDTLKECPLKHRAW

NSFLVEDHGFGVFHTSVWLKVREDYSLECDPAVIGTAVKGKEAVHSDLGY

WIESEKNDTWRLKRAHLIEMKTCEWPKSHTLWTDGIEESDLIIPKSLAGP

LSHHNTREGYRTQMKGPWHSEELEIRFEECPGTKVHVEETCGTRGPSLRS

TTASGRVIEEWCCRECTMPPLSFRAKDGCWYGMEIRPRKEPESNLVRSMV

T.

In some embodiments, the amino acid sequence of the NS1 polypeptide has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with the sequence of SEQ ID NO: 1. In some embodiments, the amino acid sequence of the NS1 polypeptide may be from the amino acid sequence encoded by the sequence of GenBank Accession number KU501215.1 (SEQ ID NO: 2). In some embodiments, the amino acid sequence of the NS1 polypeptide may be amino acid positions 795 to 1145 of the amino acid sequence encoded by the sequence of GenBank Accession number KU501215.1. In some embodiments, the amino acid sequence of the NS1 polypeptide may be from Zika virus strain PRVABC59.

"Sequence Identity", "% sequence identity", "% identity", "% identical" or "sequence alignment" means a comparison of a first amino acid sequence to a second amino acid sequence, or a comparison of a first nucleic acid sequence to a second nucleic acid sequence and is calculated as a percentage based on the comparison. The result of this calculation can be described as "percent identical" or "percent ID."

Generally, a sequence alignment can be used to calculate the sequence identity by one of two different approaches. In the first approach, both mismatches at a single position and gaps at a single position are counted as non-identical positions in final sequence identity calculation. In the second approach, mismatches at a single position are counted as non-identical positions in final sequence identity calculation; however, gaps at a single position are not counted (ignored) as non-identical positions in final sequence identity calculation. In other words, in the second approach gaps are ignored in final sequence identity calculation. The difference between these two approaches, i.e. counting gaps as non-identical positions vs ignoring gaps, at a single position can lead to variability in the sequence identity value between two sequences.

A sequence identity is determined by a program, which produces an alignment, and calculates identity counting both mismatches at a single position and gaps at a single position as non-identical positions in final sequence identity calculation. For example program Needle (EMBOS), which has implemented the algorithm of Needleman and Wunsch (Needleman and Wunsch, 1970, J. Mol. Biol. 48: 443-453), and which calculates sequence identity per default settings by first producing an alignment between a first sequence and a second sequence, then counting the number of identical positions over the length of the alignment, then dividing the number of identical residues by the length of an alignment, then multiplying this number by 100 to generate the % sequence identity [% sequence identity=(# of Identical residues/length of alignment)×100)].

A sequence identity can be calculated from a pairwise alignment showing both sequences over the full length, so showing the first sequence and the second sequence in their full length ("Global sequence identity"). For example, program Needle (EMBOSS) produces such alignments; % sequence identity=(# of identical residues/length of alignment)×100)].

A sequence identity can be calculated from a pairwise alignment showing only a local region of the first sequence or the second sequence ("Local Identity"). For example, program Blast (NCBI) produces such alignments; % sequence identity=(# of Identical residues/length of alignment)×100)].

The sequence alignment is preferably generated by using the algorithm of Needleman and Wunsch (J. Mol. Biol. (1979) 48, p. 443-453). Preferably, the program "NEEDLE" (The European Molecular Biology Open Software Suite (EMBOSS)) is used with the programs default parameter (gap open=10.0, gap extend=0.5 and matrix=EBLOSUM62 for proteins and matrix=EDNAFULL for nucleotides). Then, a sequence identity can be calculated from the alignment showing both sequences over the full length, so showing the first sequence and the second sequence in their full length ("Global sequence identity"). For example: % sequence identity=(# of identical residues/length of alignment)×100)].

In some embodiments, the at least one non-human cell adaptation mutation occurs at one or more amino acid positions within the NS1 polypeptide. In some embodiments, the mutation occurs at position 98 of SEQ ID NO: 1, or at a position corresponding to position 98 of SEQ ID NO: 1 when aligned to SEQ ID NO: 1 using a pairwise alignment algorithm. In some embodiments, the mutation at position 98 is a tryptophan to glycine substitution.

Figure 7:
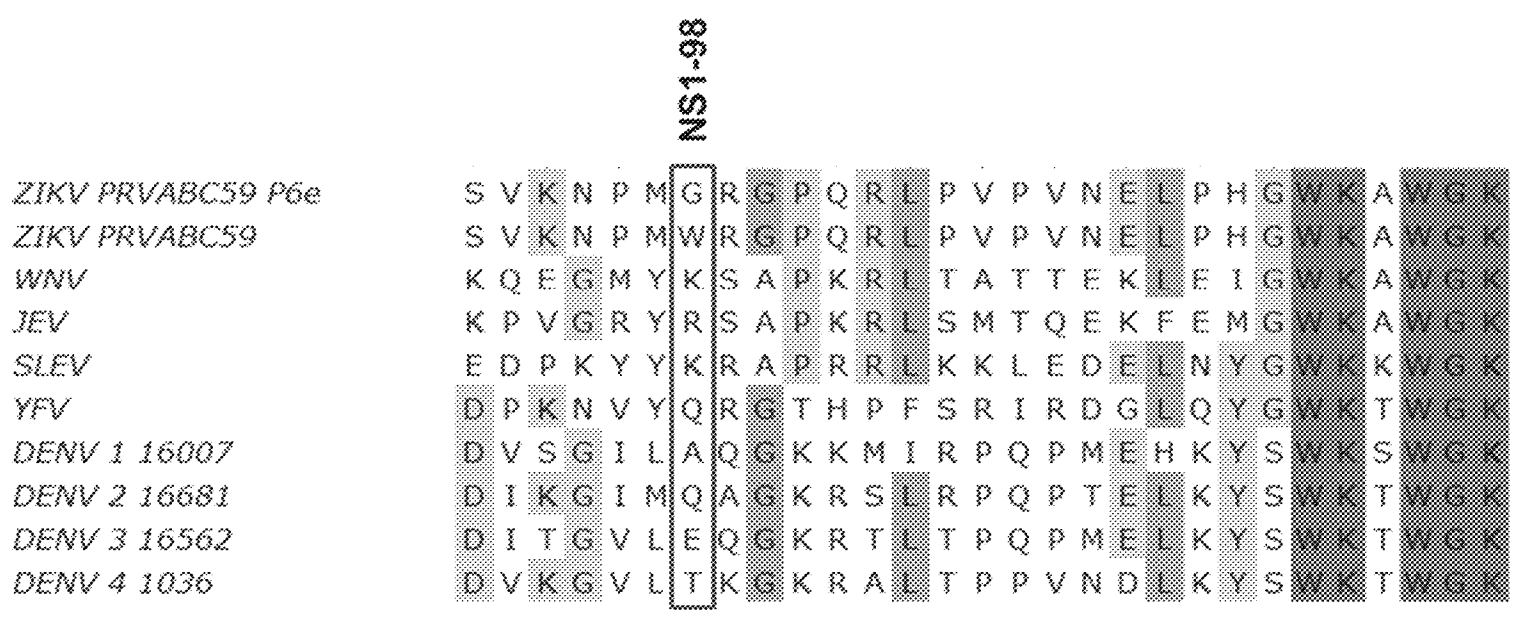

In some embodiments, the Zika virus comprises a mutation at position 98 of SEQ ID NO: 1, or at a position corresponding to position 98 of SEQ ID NO: 1. A position corresponding to position 98 of SEQ ID NO:1 can be determined by aligning the amino acid sequence of an NS-1 protein to SEQ ID NO: 1 using a pairwise alignment algorithm Amino acid residues in viruses other than Zika virus which correspond to the tryptophan residue at position 98 of SEQ ID NO:1 are shown in FIG. 7 of the present application where these residues are boxed. In some embodiments, the mutation at position 98 is a tryptophan to glycine substitution. In some embodiments, the mutation at position 98 is a tryptophan to glycine substitution at position 98 of SEQ ID NO:1.

In some embodiments, antigens of the present disclosure contain at least one non-human cell adaptation mutation within the NS1 protein, and contain at least one mutation (e.g., at least one adaptation mutation) within one or more of the C, prM, E, NS1, NS2A, NS2B, NS3, NS4A, NS4B, and NS5 viral proteins. In some embodiments, antigens of the present disclosure contain one or more non-human cell adaptation mutations within the NS1 protein, and do not contain at least one mutation (e.g., at least one non-human cell adaptation mutation) within one or more of the C, prM, E, NS1, NS2A, NS2B, NS3, NS4A, NS4B, and NS5 viral proteins. In some embodiments, antigens of the present disclosure contain at least one non-human cell adaptation mutation within the NS1 protein and do not contain at least one mutation (e.g., at least one non-human cell adaptation mutation) within the envelope protein E. In some embodiments, antigens of the present disclosure include whole, inactivated virus that contains at least one non-human cell adaptation mutation in Zika virus Non-structural protein 1 (NS1), and do not include a mutation in Zika virus envelope protein E (Env). In some embodiments, antigens of the present disclosure contain a mutation at position 98 of SEQ ID NO: 1, or at a position corresponding to position 98 of SEQ ID NO: 1 and do not contain any mutation within the envelope protein E. In some embodiments, antigens of the present disclosure include whole, inactivated virus that contains a mutation at position 98 of SEQ ID NO: 1, or at a position corresponding to position 98 of SEQ ID NO: 1 and do not include a mutation in Zika virus envelope protein E (Env). In some embodiments, whole, inactivated virus contains at least one mutation in Zika virus Non-structural protein 1 (NS1) and the sequence encoding the envelope protein is the same as the corresponding sequence in SEQ ID No. 2. In some embodiments, the Zika virus contains a mutation at position 98 of SEQ ID NO: 1, or at a position corresponding to position 98 of SEQ ID NO: 1 and the sequence encoding the envelope protein is the same as the corresponding sequence in SEQ ID No. 2. In some embodiments, whole, inactivated Zika virus contains a mutation at position 98 of SEQ ID NO: 1, or at a position corresponding to position 98 of SEQ ID NO: 1 and the sequence encoding the envelope protein is the same as the corresponding sequence in SEQ ID No. 2.

In some embodiments, antigens of the present disclosure, such as Zika virus, contain at least one non-human cell adaptation mutation that enhances genetic stability as compared to a Zika virus lacking the at least one adaptation mutation. In some embodiments, antigens of the present disclosure, such as Zika virus, contain at least one non-human cell adaptation mutation that enhances viral replication as compared to a Zika virus lacking the at least one adaptation mutation. In some embodiments, antigens of the present disclosure, such as Zika virus, contain at least one non-human cell adaptation mutation reduces or otherwise inhibits the occurrence of undesirable mutations, such as within the envelope protein E (Env) of the Zika virus.

In the above embodiments of the present disclosure, an exemplary pairwise alignment algorithm is the Needleman-Wunsch global alignment algorithm, using default parameters (e.g. with Gap opening penalty=10.0, and with Gap extension penalty=0.5, using the EBLOSUM62 scoring matrix). This algorithm is conveniently implemented in the needle tool in the EMBOSS package.

In some embodiments, antigens of the present disclosure from a Zika virus may be used in any of the vaccines and immunogenic compositions of the present disclosure. For example, the antigens of the present disclosure may be useful for treating or preventing Zika virus infection in a subject in need thereof and/or inducing an immune response, such as a protective immune response, against Zika virus in a subject in need thereof.

Production of Vaccines and Immunogenic Compositions

Other aspects of the present disclosure relate to Zika virus vaccines and immunogenic compositions containing one or more antigens of the present disclosure from at least one Zika virus in particular in the form of a purified inactivated whole virus, such as a Zika virus with a mutation which is a tryptophan to glycine substitution at position 98 of SEQ ID NO:1 or at a position corresponding to position 98 of SEQ ID NO:1 as described herein. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRV-ABC59 comprising the genomic sequence according to SEQ ID NO:2. In one embodiment, the vaccines and immunogenic compositions contain a plaque purified clonal Zika virus isolate. Such vaccines and immunogenic compositions may be useful, for example, for treating or preventing Zika virus infection in a subject in need thereof and/or inducing an immune response, such as a protective immune response, against Zika virus in a subject in need thereof. Vaccines and/or immunogenic compositions of the present disclosure may include, without limitation, purified viruses, inactivated viruses, attenuated viruses, recombinant viruses, purified and/or recombinant viral proteins for subunit vaccines. Vaccines and/or immunogenic compositions of the present disclosure may further include a purified antigen vaccine or immunogenic composition, a subunit vaccine or immunogenic composition, an inactivated whole virus vaccine or immunogenic composition, or an attenuated virus vaccine or immunogenic composition.

Production of vaccines and/or immunogenic compositions of the present disclosure includes growth of Zika virus, with antigens being prepared from the grown virus. Growth in cell culture is a method for preparing vaccines and/or immunogenic compositions of the present disclosure. Cells for viral growth may be cultured in suspension or in adherent conditions.

Cell lines suitable for growth of the at least one virus of the present disclosure are preferably of mammalian origin, and include, but are not limited to: insect cells (e.g., mosquito cells as described herein, VERO cells (from monkey kidneys), horse, cow (e.g. MDBK cells), sheep, dog (e.g. MDCK cells from dog kidneys, ATCC CCL34 MDCK (NBL2) or MDCK 33016, deposit number DSM ACC 2219 as described in WO97/37001), cat, and rodent (e.g. hamster cells such as BHK21-F, HKCC cells, or Chinese hamster ovary cells (CHO cells)), and may be obtained from a wide variety of developmental stages, including for example, adult, neonatal, fetal, and embryo. In certain embodiments, the cells are immortalized (e.g. PERC.6 cells, as described in WO 01/38362 and WO 02/40665, and as deposited under ECACC deposit number 96022940). In preferred embodiments, mammalian cells are utilized, and may be selected from and/or derived from one or more of the following non-limiting cell types: fibroblast cells (e.g. dermal, lung), endothelial cells (e.g. aortic, coronary, pulmonary, vascular, dermal microvascular, umbilical), hepatocytes, keratinocytes, immune cells (e.g. T cell, B cell, macrophage, NK, dendritic), mammary cells (e.g. epithelial), smooth muscle cells (e.g. vascular, aortic, coronary, arterial, uterine, bronchial, cervical, retinal pericytes), melanocytes, neural cells (e.g. astrocytes), prostate cells (e.g. epithelial, smooth muscle), renal cells (e.g. epithelial, mesangial, proximal tubule), skeletal cells (e.g. chondrocyte, osteoclast, osteoblast), muscle cells (e.g. myoblast, skeletal, smooth, bronchial), liver cells, retinoblasts, and stromal cells. WO97/37000 and WO97/37001 describe production of animal cells and cell lines that are capable of growth in suspension and in serum free media and are useful in the production and replication of viruses.

Culture conditions for the above cell types are known and described in a variety of publications. Alternatively culture medium, supplements, and conditions may be purchased commercially, such as for example, described in the catalog and additional literature of Cambrex Bioproducts (East Rutherford, N.J.).

In certain embodiments, the cells used in the methods described herein are cultured in serum free and/or protein free media. A medium is referred to as a serum-free medium in the context of the present disclosure in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Known serum-free media include Iscove's medium, Ultra-CHO medium (BioWhittaker) or EX-CELL (JRH Bioscience). Ordinary serum-containing media include Eagle's Basal Medium (BME) or Minimum Essential Medium (MEM) (Eagle, Science, 130, 432 (1959)) or Dulbecco's Modified Eagle Medium (DMEM or EDM), which are ordinarily used with up to 10% fetal calf serum or similar additives. Optionally, Minimum Essential Medium (MEM) (Eagle, Science, 130, 432 (1959)) or Dulbecco's Modified Eagle Medium (DMEM or EDM) may be used without any serum containing supplement. Protein-free media like PF-CHO (JHR Bioscience), chemically-defined media like ProCHO 4CDM (BioWhittaker) or SMIF 7 (Gibco/BRL Life Technologies) and mitogenic peptides like Primactone, Pepticase or HyPep™ (all from Quest International) or lactalbumin hydrolysate (Gibco and other manufacturers) are also adequately known in the prior art. The media additives based on plant hydrolysates have the special advantage that contamination with viruses, mycoplasma or unknown infectious agents can be ruled out.

Cell culture conditions (temperature, cell density, pH value, etc.) are variable over a very wide range owing to the suitability of the cell line employed according to the present disclosure and can be adapted to the requirements of particular viral strains.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. In some embodiments, the virus is collected via plaque purification. The cultured cells are inoculated with a virus (measured by PFU or TCID50) to cell ratio of 1:500 to 1:1, preferably 1:100 to 1:5. The virus is added to a suspension of the cells or is applied to a monolayer of the cells, and the virus is absorbed on the cells for at least 10 minutes, at least 20 minutes, at least 30 minutes, at least 40 minutes, at least 50 minutes, at least 60 minutes but usually less than 300 minutes at 25° C. to 40° C., preferably 28° C. to 38° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("MOI") of about 0.0001 to 10, preferably 0.002 to 5, more preferably to 0.001 to 2. Still more preferably, the cells are infected at an MOI of about 0.01. The supernatant of the infected cells may be harvested from 30 to 60 hours post infection, or 3 to 10 days post infection. In certain preferred embodiments, the supernatant of the infected cells is harvested 3 to 7 days post infection. More preferably, the supernatant of the infected cells is harvested 3 to 5 days post infection. In some embodiments, proteases (e.g., trypsin) may be added during cell culture to allow viral release, and the proteases may be added at any suitable stage during the culture. Alternatively, in certain embodiments, the supernatant of infected cell cultures may be harvested and the virus may be isolated or otherwise purified from the supernatant.

The viral inoculum and the viral culture are preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [WO2006/027698].

Where virus has been grown on a cell line then it is standard practice to minimize the amount of residual cell line DNA in the final vaccine, in order to minimize any oncogenic activity of the host cell DNA. Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination disclosed in references (Lundblad (2001) Biotechnology and Applied Biochemistry 34:195-197, *Guidance for Industry: Bioanalytical Method Validation*. U.S. Department of Health and Human Services Food and Drug Administration Center for Drug Evaluation and Research (CDER) Center for Veterinary Medicine (CVM). May 2001) involves a two-step treatment, first using a DNase (e.g. Benzonase), which may be used during viral growth, and then a cationic detergent (e.g. CTAB), which may be used during virion disruption. Removal by β-propiolactone treatment can also be used. In one embodiment, the contaminating DNA is removed by benzonase treatment of the culture supernatant.

Production of Antigens

Antigens of the present disclosure for use in vaccines and/or immunogenic compositions including, without limitation, purified viruses, inactivated viruses, attenuated viruses, recombinant viruses, or purified and/or recombinant viral proteins for subunit vaccines to treat and/or prevent Zika virus infection and/or induce an immune response, such as a protective immune response, against Zika virus, may be produced and/or purified or otherwise isolated by any suitable method known in the art. Antigens of the present disclosure may include, without limitation, whole virus, attenuated virus, inactivated virus, proteins, polypeptides (including active proteins and individual polypeptide epitopes within proteins), glycopolypeptides, lipopolypeptides, peptides, polysaccharides, polysaccharide conjugates, peptide and non-peptide mimics of polysaccharides and other molecules, small molecules, lipids, glycolipids, and carbohydrates produced, derived, purified, and/or otherwise isolated from a Zika virus. For example, suitable antigens may include, without limitation, structural polypeptides such as C, prM, and/or E, and non-structural polypeptides such as NS1, NS2A, NS2B, NS3, NS4A, NS4B, and/or NS5 from Zika virus. In one embodiment, the antigen of the present disclosure is a purified inactivated whole Zika virus.

Antigen of the present disclosure may be synthesized chemically or enzymatically, produced recombinantly, isolated from a natural source, or a combination of the foregoing. In certain embodiments, antigens of the present disclosure are produced, purified, isolated, and/or derived from at least one Zika virus of the present disclosure. Antigens of the present disclosure may be purified, partially purified, or a crude extract. In some embodiments, antigens of the present disclosure are viruses, such as inactivated viruses, produced as described in the above section entitled "Production of Vaccines and Immunogenic Compositions."

In certain embodiments, one or more antigens of the present disclosure may be produced by culturing a non-human cell. Cell lines suitable for production of the one or more antigens of the present disclosure may include insect cells (e.g., any of the mosquito cells described herein). Cell lines suitable for production of the one or more antigens of the present disclosure may also be cells of mammalian origin, and include, but are not limited to: VERO cells (from monkey kidneys), horse, cow (e.g. MDBK cells), sheep, dog (e.g. MDCK cells from dog kidneys, ATCC CCL34 MDCK (NBL2) or MDCK 33016, deposit number DSM ACC 2219 as described in WO97/37001), cat, and rodent (e.g. hamster cells such as BHK21-F, HKCC cells, or Chinese hamster ovary cells (CHO cells)), and may be obtained from a wide variety of developmental stages, including for example, adult, neonatal, fetal, and embryo. In certain embodiments, the cells are immortalized (e.g. PERC.6 cells, as described in WO01/38362 and WO02/40665, and as deposited under ECACC deposit number 96022940). In preferred embodiments, mammalian cells are utilized, and may be selected from and/or derived from one or more of the following non-limiting cell types: fibroblast cells (e.g. dermal, lung), endothelial cells (e.g. aortic, coronary, pulmonary, vascular, dermal microvascular, umbilical), hepatocytes, keratinocytes, immune cells (e.g. T cell, B cell, macrophage, NK, dendritic), mammary cells (e.g. epithelial), smooth muscle cells (e.g. vascular, aortic, coronary, arterial, uterine, bronchial, cervical, retinal pericytes), melanocytes, neural cells (e.g. astrocytes), prostate cells (e.g. epithelial, smooth muscle), renal cells (e.g. epithelial, mesangial, proximal tubule), skeletal cells (e.g. chondrocyte, osteoclast, osteoblast), muscle cells (e.g. myoblast, skeletal, smooth, bronchial), liver cells, retinoblasts, and stromal cells. WO97/37000 and WO97/37001 describe production of animal cells and cell lines that capable of growth in suspension and in serum free media and are useful in the production of viral antigens. In certain embodiments, the non-human cell is cultured in serum-free media.

Polypeptide antigens may be isolated from natural sources using standard methods of protein purification known in the art, including, but not limited to, liquid chromatography (e.g., high performance liquid chromatography, fast protein liquid chromatography, etc.), size exclusion chromatography, gel electrophoresis (including one-dimensional gel electrophoresis, two-dimensional gel electrophoresis), affinity chromatography, or other purification technique. In many embodiments, the antigen is a purified antigen, e.g., from about 50% to about 75% pure, from about 75% to about 85% pure, from about 85% to about 90% pure, from about 90% to about 95% pure, from about 95% to about 98% pure, from about 98% to about 99% pure, or greater than 99% pure.

One may employ solid phase peptide synthesis techniques, where such techniques are known to those of skill in the art. See Jones, The Chemical Synthesis of Peptides (Clarendon Press, Oxford) (1994). Generally, in such methods a peptide is produced through the sequential addition of activated monomeric units to a solid phase bound growing peptide chain.

Well-established recombinant DNA techniques can be employed for production of polypeptides, where, e.g., an expression construct comprising a nucleotide sequence encoding a polypeptide is introduced into an appropriate host cell (e.g., a eukaryotic host cell grown as a unicellular entity in in vitro cell culture, e.g., a yeast cell, an insect cell, a mammalian cell, etc.) or a prokaryotic cell (e.g., grown in in vitro cell culture), generating a genetically modified host cell; under appropriate culture conditions, the protein is produced by the genetically modified host cell.

Besides killed and attenuated virus immunogenic compositions, one can use a subunit immunogenic composition or other type of immunogenic composition which presents to the animal the antigenic components of Zika virus. The antigenic component may be a protein, glycoprotein, lipid-conjugated protein or glycoprotein, a modified lipid moiety, or other viral component which, when injected into a human, stimulates an immune response in the human such that the human develops protective immunity against Zika virus. For a subunit immunogenic composition, the virus can be cultured on mammalian cells, as described above. The cell culture can be homogenized and an immunogenic composition can be isolated by passage of the cell culture homogenate over the appropriate column or through the appropriate pore size filter or via centrifugation of the cell culture homogenate.

If the antigenic component is a protein, then one can isolate the nucleic acid which encodes that protein and generate an immunogenic composition that contains that isolated nucleic acid. The nucleic acid encoding the antigenic component can be placed on a plasmid downstream of a signal sequence of a eukaryotic promoter. That plasmid can contain one or more selectable markers and be transfected into an attenuated prokaryotic organism, such as *Salmonella* spp., *Shigella* spp., or other suitable bacteria. The bacteria can then be administered to the human so that the human can generate a protective immune response to the antigenic component. Alternatively, the nucleic acid encoding the antigenic component can be placed downstream of a prokaryotic promoter, have one or more selectable markers, and be transfected into an attenuated prokaryotic organism such as *Salmonella* spp., *Shigella* spp., or other suitable bacteria. The bacteria can then be administered to the eukaryotic subject for which immune response to the antigen of interest is desired. See, for example, U.S. Pat. No. 6,500,419.

For a subunit immunogenic composition, the nucleic acid encoding a proteinaceous antigenic component of a Zika virus can be cloned into a plasmid such as those described in International Patent Application Publication Number WO 00/32047 (Galen) and International Patent Application Publication Number WO 02/083890 (Galen). Then the plasmid can be transfected into bacteria and the bacteria can produce the desired antigenic protein. One can isolate and purify the desired antigenic protein by a variety of methods described in both patent applications.

Virus Inactivation

Certain aspects of the present disclosure relate to Zika virus vaccines and immunogenic compositions containing one or more antigens from a Zika virus. Vaccines and/or immunogenic compositions of the present disclosure may include a purified virus, a whole virus, a recombinant virus, a live attenuated whole virus or, preferably, an inactivated whole virus, or subunits, polypeptides, and/or antigens from an inactivated virus. As such, certain embodiments of the present disclosure relate to Zika virus vaccines and/or immunogenic compositions containing one or more antigens from at least one inactivated Zika virus. Certain embodiments of the present disclosure relate to Zika virus vaccines and/or immunogenic compositions containing a purified inactivated Zika virus. The term "inactivated Zika virus" as used herein is intended to comprise a Zika virus which has been treated with an inactivating method such as treatment with an effective amount of formalin. In particular, the inactivated Zika virus is obtainable/obtained from a method wherein the Zika virus is treated with formaldehyde in an amount of about 0.02% w/v for 14 days at a temperature of 22° C. The inactivated Zika virus is no longer able to infect host cells which can be infected with a Zika virus which has not been inactivated. In one embodiment, the inactivated Zika virus is no longer able to infect VERO cells and exert a cytopathic effect on the VERO cells. The term "purified Zika virus" means that the Zika virus has been subjected to a purification process as described below. The purified Zika virus has a lower content of host cell proteins such as Vero cell proteins and host cell DNA such as Vero cell DNA than a non-purified Zika virus. The purity of the purified Zika virus can be determined by size exclusion chromatography. The main peak of the purified Zika virus in the size exclusion chromatography may be more than 85% of the total area under the curve in the size exclusion chromatography, or more than 90% of the total area under the curve in the size exclusion chromatography, or more than 95% of the total area under the curve in the size exclusion chromatography. Such results are considered as "purified" Zika virus. The term "purified inactivated whole Zika virus" thus refers to a Zika virus obtainable/obtained from a method wherein the Zika virus is treated with formalin in an amount that ranges from about 0.02% w/v for days at a temperature of 22° C. and provides a main peak of at least 85% of the total area under the curve in the size exclusion chromatography. In certain embodiments the purified inactivated whole Zika virus is a clonal isolate obtained/obtainable by plaque purification.

Methods of inactivating or killing viruses to destroy their ability to infect mammalian cells, but do not destroy the secondary, tertiary or quaternary structure and immunogenic epitopes of the virus are known in the art. Such methods include both chemical and physical means. Suitable means for inactivating a virus include, without limitation, treatment with an effective amount of one or more agents selected from detergents, formalin (also referred to herein as "formaldehyde"), hydrogen peroxide, beta-propiolactone (BPL), binary ethylamine (BEI), acetyl ethyleneimine, heat, electromagnetic radiation, x-ray radiation, gamma radiation, ultraviolet radiation (UV radiation), UV-A radiation, UV-B radiation, UV-C radiation, methylene blue, psoralen, carboxyfullerene (C60), hydrogen peroxide and any combination of any thereof.

In certain embodiments of the present disclosure the at least one virus is chemically inactivated. Agents for chemical inactivation and methods of chemical inactivation are well-known in the art and described herein. In some embodiments, the at least one virus is chemically inactivated with one or more of BPL, hydrogen peroxide, formalin, or BEI. In certain embodiments where the at least one virus is chemically inactivated with BPL, the virus may contain one or more modifications. In some embodiments, the one or more modifications may include a modified nucleic acid. In some embodiments, the modified nucleic acid is an alkylated nucleic acid. In other embodiments, the one or more modifications may include a modified polypeptide. In some embodiments, the modified polypeptide contains a modified amino acid residue including one or more of a modified cysteine, methionine, histidine, aspartic acid, glutamic acid, tyrosine, lysine, serine, and threonine.

In certain embodiments where the at least one virus is chemically inactivated with formalin, the inactivated virus may contain one or more modifications. In some embodiments, the one or more modifications may include a modified polypeptide. In some embodiments, the one or more modifications may include a cross-linked polypeptide. In some embodiments where the at least one virus is chemically inactivated with formalin, the vaccine or immunogenic composition further includes formalin. In certain embodiments where the at least one virus is chemically inactivated with BEI, the virus may contain one or more modifications. In some embodiments, the one or more modifications may include a modified nucleic acid. In some embodiments, the modified nucleic acid is an alkylated nucleic acid.

In some embodiments where the at least one virus is chemically inactivated with formalin, any residual unreacted formalin may be neutralized with sodium metabisulfite, may be dialyzed out, and/or may be buffer exchanged to remove the residual unreacted formalin. In some embodiments, the sodium metabisulfite is added in excess. In some embodiments, the solutions may be mixed using a mixer, such as an in-line static mixer, and subsequently filtered or further purified (e.g., using a cross flow filtrations system).

Certain embodiments of the present disclosure relate to a method for inactivating a Zika virus preparation. In some embodiments, the method involves (a) isolating the Zika virus preparation from one or more non-human cells that are used to produce the virus preparation and (b) treating the virus preparation with an effective amount of formalin. In certain embodiments, treating with an effective amount of formalin includes, without limitation, treating with formalin in an amount that ranges from about 0.001% v/v to about 3.0% v/v. For example, treating with an effective amount of formalin may include treating with formalin in an amount that ranges from about 0.001% to about 3.0% v/v, about 0.005% to about 2.0% v/v, or about 0.01% to about 1.0% v/v, or in an amount of about 0.001%, about 0.0025%, about 0.005%, about 0.0075%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.25%, about 1.5%, about 1.75%, about 2.0%, about 2.25%, about 2.5%, about 2.75%, or about 3.0% v/v.

In certain embodiments of the method, the Zika virus preparation is treated with formalin at a temperature that ranges from about 2° C. to about 42° C. For example, the Zika virus preparation may be treated with formalin at a temperature that ranges from about 2° C. to about 42° C., about 2° C. to about 8° C., about 15° C. to about 37° C., about 17° C. to about 27° C., about 20° C. to about 25° C., or at a temperature of about 2° C., about 4° C., about 8° C., about 10° C., about 15° C., about 17° C., about 18° C., about 19° C., about 20° C., about 21° C., about 22° C., about 23° C., about 24° C., about 25° C., about 26° C., about 27° C., about 28° C., about 29° C., about 30° C., about 37° C., or about 42° C. In some embodiments, the Zika virus preparation is treated with formalin at room temperature.

In some embodiments, the Zika virus preparation is treated with formalin for at least about 1 day. For example, the Zika virus preparation may be treated with formalin for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days, or more. In some embodiments, the Zika virus preparation is treated with formalin for at least about 9 days. In some embodiments, the Zika virus preparation is treated with formalin for at least about 11 days. In some embodiments, the Zika virus preparation is treated with formalin for at least about 14 days. In some embodiments, the Zika virus preparation is treated with formalin for at least about 20 days. In some embodiments, the Zika virus preparation is treated with formalin for at least about 30 days.

An inactivated whole Zika virus preparation is considered to be obtainable/obtained from a method wherein the Zika virus is treated with formaldehyde in an amount of about 0.02% w/v for 14 days at a temperature of 22° C.

In some embodiments, the method further involves neutralizing unreacted formalin with an effective amount of sodium metabisulfite. In some embodiments, the effective amount of sodium metabisulfite ranges from about 0.01 mM to about 100 mM. For example, the sodium metabisulfite may be added at an effective concentration of from about 0.01 mM to about 100 mM, from about 0.1 mM to about 50 mM, from about 0.5 mM to about 20 mM, or from about 1 mM to about 10 mM, or at a concentration of about 0.01 mM, about 0.05 mM, about 0.1 mM, about 0.25 mM, about 0.5 mM, about 0.75 mM, about 1 mM, about 2 mM, about 3 mM, about 4 mM, about 5 mM, about 6 mM, about 7 mM, about 8 mM, about 9 mM, about 10 mM, about 20 mM, about 30 mM about 40 mM, about 50 mM, about 75 mM or about 100 mM. In some embodiments, the formalin is neutralized with about 2 mM sodium metabisulfite.

In some embodiments, the Zika virus preparation is treated with hydrogen peroxide. In some embodiments, the Zika virus preparation is treated with hydrogen peroxide at concentrations ranging from 0.1 to 3%, preferably 0.1 to 1% at any temperature from 20° C. to 30° C. for 5 to 120 minutes, some embodiments, the Zika virus preparation is treated with hydrogen peroxide at a final concentration of 0.01% for 60 minutes or less.

In some embodiments, the method involves (a) isolating the Zika virus preparation from one or more non-human cells that are used to produce the virus preparation; (b) treating the virus preparation with an effective amount of formalin; (c) neutralizing the virus preparation with an effective amount of sodium metabisulfite; and (d) purifying the neutralized virus preparation. Any method of purifying a virus preparation known in the art may be employed, including, without limitation, using cross flow filtration (CFF), multimodal chromatography, size exclusion chromatography, cation exchange chromatography, and/or anion exchange chromatography. In some embodiments, the neutralized virus preparation is purified by cross flow filtration (CFF). In some embodiments, the virus preparation is purified to a high degree in an amount that is about 70%, about 75%, about 80%, about 85%, about 90%, about 91%, about 92%, about 93%, about 94%, about 95% about 96%, about 97%, about 98%, about 99%, or more.

The vaccines and/or immunogenic compositions of the present disclosure containing one or more antigens from at least one inactivated Zika virus may be useful for treating or preventing Zika virus infection in a subject in need thereof and/or inducing an immune response, such as a protective immune response, against Zika virus in a subject in need thereof.

Adjuvants

Other aspects of the present disclosure relate to Zika virus vaccines and/or immunogenic compositions containing one or more antigens from at least one Zika virus described herein in combination with one or more adjuvants. In some embodiments, the vaccines and/or immunogenic compositions contain a purified inactivated whole Zika virus such as a Zika virus with a mutation which is a tryptophan to glycine substitution at position 98 of SEQ ID NO:1 or at a position corresponding to position 98 of SEQ ID NO:1 as described herein in combination with one or more adjuvants. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRV-ABC59 in combination with one or more adjuvants. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRV-ABC59 comprising the genomic sequence according to SEQ ID NO:2 in combination with one or more adjuvants. In one embodiment, the vaccines and immunogenic compositions contain a plaque purified clonal Zika virus isolate in combination with one or more adjuvants. Such adjuvanted vaccines and/or immunogenic compositions of the present disclosure may be useful for treating or preventing Zika virus infection in a subject in need thereof and/or inducing an immune response, such as a protective immune response, against Zika virus in a subject in need thereof.

Various methods of achieving an adjuvant effect for vaccines are known and may be used in conjunction with the Zika virus vaccines and/or immunogenic compositions disclosed herein. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generation Immunological Adjuvants", 1995, Gregoriadis G et al. (eds.), Plenum Press, New York, ISBN 0-306-45283-9.

In some embodiments, a Zika virus vaccine or immunogenic composition includes the antigens and an adjuvant. Antigens may be in a mixture with at least one adjuvant, at a weight-based ratio of from about 10:1 to about $10^{10}$:1 antigen:adjuvant, e.g., from about 10:1 to about 100:1, from about 100:1 to about $10^3$:1, from about $10^3$:1 to about $10^4$:1, from about $10^4$:1 to about $10^5$:1, from about $10^5$:1 to about $10^6$:1, from about $10^6$:1 to about $10^7$:1, from about $10^7$:1 to about $10^8$:1, from about $10^8$:1 to about $10^9$:1, or from about $10^9$:1 to about $10^{10}$:1 antigen:adjuvant. One of skill in the art can readily determine the appropriate ratio through information regarding the adjuvant and routine experimentation to determine optimal ratios.

Exemplary adjuvants may include, but are not limited to, aluminum salts, calcium phosphate, toll-like receptor (TLR) agonists, monophosphoryl lipid A (MLA), MLA derivatives, synthetic lipid A, lipid A mimetics or analogs, cytokines, saponins, muramyl dipeptide (MDP) derivatives, CpG oligos, lipopolysaccharide (LPS) of gram-negative bacteria, polyphosphazenes, emulsions (oil emulsions), chitosan, vitamin D, stearyl or octadecyl tyrosine, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA). In some embodiments, the adjuvant is an aluminum salt.

In some embodiments, the adjuvant includes at least one of alum, aluminum phosphate, aluminum hydroxide, potassium aluminum sulfate, and Alhydrogel 85. In some embodiments, aluminum salt adjuvants of the present disclosure have been found to increase adsorption of the antigens of the Zika virus vaccines and/or immunogenic compositions of the present disclosure. Accordingly, in some embodiments, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% of the antigen is adsorbed to the aluminum salt adjuvant.

In some embodiments, the vaccine or immunogenic composition includes an aluminum salt adjuvant (e.g., alum) from about 1 µg to about 500 µg, about 5 µg to about 500 µg, about 10 µg to about 500 lag, about 15 µg to about 500 µg, about 25 µg to about 500 µg, about 50 µg to about 500 µg, about 75 µg to about 500 µg, about 100 µg to about 500 µg, about 125 µg to about 500 µg, about 150 µg to about 500 µg, about 175 µg to about 500 µg, about 200 µg to about 500 µg, about 225 µg to about 500 µg, about 250 µg to about 500 µg, about 275 µg to about 500 µg, about 300 µg to about 500 µg, about 325 µg to about 500 µg, about 350 µg to about 500 µg, about 375 µg to about 500 µg, about 400 µg to about 500 µg, about 425 µg to about 500 µg, about 450 µg to about 500 µg, about 475 µg to about 500 µg, about 1 µg to about 475 µg, about 5 µg to about 475 µg, about 10 µg to about 475 µg, about 15 µg to about 475 µg, about 25 µg to about 475 lag, about 50 µg to about 475 µg, about 75 µg to about 475 µg, about 100 µg to about 475 µg, about 125 µg to about 475 µg, about 150 µg to about 475 µg, about 175 µg to about 475 µg, about 200 µg to about 475 µg, about 225 µg to about 475 µg, about 250 µg to about 475 µg, about 275 µg to about 475 µg, about 300 µg to about 475 µg, about 325 µg to about 475 µg, about 350 µg to about 475 µg, about 375 µg to about 475 µg, about 400 µg to about 475 µg, about 425 µg to about 475 µg, about 450 µg to about 475 µg, about 1 µg to about 450 µg, about 5 µg to about 450 µg, about 10 µg to about 450 µg, about 15 µg to about 450 µg, about 25 µg to about 450 µg, about 50 µg to about 450 µg, about 75 µg to about 450 µg, about 100 µg to about 450 lag, about 125 µg to about 450 µg, about 150 µg to about 450 µg, about 175 µg to about 450 µg, about 200 µg to about 450 µg, about 225 µg to about 450 µg, about 250 µg to about 450 µg, about 275 µg to about 450 µg, about 300 µg to about 450 µg, about 325 µg to about 450 µg, about 350 µg to about 450 µg, about 375 µg to about 450 µg, about 400 µg to about 450 µg, about 425 µg to about 450 µg, about 1 µg to about 425 µg, about 5 µg to about 425 µg, about 10 µg to about 425 µg, about 15 µg to about 425 µg, about 25 µg to about 425 lag, about 50 µg to about 425 µg, about 75 µg to about 425 µg, about 100 µg to about 425 µg, about 125 µg to about 425 µg, about 150 µg to about 425 µg, about 175 µg to about 425 µg, about 200 µg to about 425 µg, about 225 µg to about 425 µg, about 250 µg to about 425 µg, about 275 µg to about 425 µg, about 300 µg to about 425 µg, about 325 µg to about 425 µg, about 350 µg to about 425 µg, about 375 µg to about 425 µg, about 400 µg to about 425 µg, about 1 µg to about 400 µg, about 5 µg to about 400 µg, about 10 µg to about 400 µg, about 15 µg to about 400 µg, about 25 µg to about 400 µg, about 50 µg to about 400 µg, about 75 lag to about 400 µg, about 100 µg to about 400 µg, about 125 µg to about 400 µg, about 150 µg to about 400 µg, about 175 µg to about 400 µg, about 200 µg to about 400 µg, about 225 µg to about 400 µg, about 250 µg to about 400 µg, about 275 µg to about 400 µg, about 300 µg to about 400 µg, about 325 µg to about 400 µg, about 350 µg to about 400 µg, about 375 µg to about 400 µg, about 1 µg to about 375 µg, about 5 µg to about 375 µg, about 10 µg to about 375 µg, about 15 µg to about 375 µg, about 25 µg to about 375 µg, about 50 lag to about 375 µg, about 75 µg to about 375 µg, about 100 µg to about 375 µg, about 125 µg to about 375 µg, about 150 µg to about 375 µg, about 175 µg to about 375 µg, about 200 µg to about 375 µg, about 225 µg to about 375 µg, about 250 µg to about 375 µg, about 275 µg to about 375 µg, about 300 µg to about 375 µg, about 325 µg to about 375 µg, about 350 µg to about 375 µg, about 1 µg to about 350 µg, about 5 µg to about 350 µg, about 10 µg to about 350 µg, about 15 µg to about 350 µg, about 25 µg to about 350 µg, about 50 µg to about 350 µg, about 75 µg to about 350 µg, about 100 µg to about 350 µg, about 125 µg to about 350 µg, about 150 µg to about 350 µg, about 175 µg to about 350 µg, about 200 µg to about 350 µg, about 225 µg to about 350 µg, about 250 µg to about 350 µg, about 275 µg to about 350 µg, about 300 µg to about 350 µg, about 325 lag to about 350 µg, about 1 µg to about 325 µg, about 5 µg to about 325 µg, about 10 µg to about 325 µg, about 15 µg to about 325 µg, about 25 µg to about 325 µg, about 50 µg to about 325 µg, about 75 µg to about 325 µg, about 100 µg to about 325 µg, about 125 µg to about 325 µg, about 150 µg to about 325 µg, about 175 µg to about 325 µg, about 200 µg to about 325 µg, about 225 µg to about 325 µg, about 250 µg to about 325 µg, about 275 µg to about 325 µg, about 300 µg to about 325 µg, about 1 µg to about 300 µg, about 5 µg to about 300 µg, about 10 µg to about 300 µg, about 15 µg to about 300 µg, about 25 µg to about 300 µg, about 50 µg to about 300 µg, about 75 µg to about 300 µg, about 100 µg to about 300 µg, about 125 µg to about 300 µg, about 150 µg to about 300 µg, about 175 µg to about 300 µg, about 200 µg to about 300 µg, about 225 µg to about 300 µg, about 250 µg to about 300 µg, about 275 µg to about 300 µg, about 1 µg to about 275 µg, about 5 µg to about 275 µg, about 10 µg to about 275 µg, about 15 µg to about 275 µg, about 25 µg to about 275 µg, about 50 µg to about 275 µg, about 75 µg to about 275 µg, about 100 µg to about 275 µg, about 125 µg to about 275 µg, about 150 µg to about 275 µg, about 175 µg to about 275 µg, about 200 µg to about 275 µg, about 225 µg to about 275 µg, about 250 µg to about 275 µg, about 1 µg to about 250 µg, about 5 µg to about 250 µg, about 10 µg to about 250 µg, about 15 µg to about 250 µg, about 25 lag to about 250 µg, about 50 µg to about 250 µg, about 75 µg to about 250 µg, about 100 µg to about 250 µg, about 125 µg to about 250 µg, about 150 µg to about 250 µg, about 175 µg to about 250 µg, about 200 µg to about 250 µg, about 225 µg to about 250 µg, about 1 µg to about 225 µg, about 5 µg to about 225 µg, about 10 µg to about 225 µg, about 15 µg to about 225 µg, about 25 µg to about 225 µg, about 50 µg to about 225 lag, about 75 µg to about 225 µg, about 100 µg to about 225 µg, about 125 µg to about 225 µg, about 150 µg to about 225 µg, about 175 µg to about 225 µg, about 200 µg to about 225 µg, about 1 µg to about 200 µg, about 5 µg to about 200 µg, about 10 µg to about 200 µg, about 15 µg to about 200 µg, about 25 µg to about 200 µg, about 50 µg to about 200 µg, about 75 µg to about 200 µg, about 100 µg to about 200 µg, about 125 lag to about 200 µg, about 150 µg to about 200 µg, about 175 µg to about 200 µg, about 1 µg to about 175 µg, about 5 µg to about 175 µg, about 10 µg to about 175 µg, about 15 µg to about 175 µg, about 25 µg to about 175 µg, about 50 µg to about 175 µg, about 75 µg to about 175 µg, about 100 µg to about 175 µg, about 125 lag to about 175 µg, about 150 µg to about 175 µg, about 1 µg to about 150 µg, about 5 µg to about 150 µg, about 10 µg to about 150 µg, about 15 µg to about 150 µg, about 25 µg to about 150 µg, about 50 µg to about 150 µg, about 75 µg to about 150 µg, about 100 µg to about 150 µg, about 125 µg to about 150 µg, about 1 µg to about 125 µg, about 5 µg to about 125 µg, about 10 µg to about 125 µg, about 15 µg to about 125 µg, about 25 µg to about 125 µg, about 50 µg to about 125 µg, about 75 µg to about 125 µg, about 100 µg to about 125 lag, about 1 µg to about 100 µg, about 5 µg to about 100 µg, about 10 µg to about 100 µg, about 15 µg to about 100 µg, about 25 µg to about 100 µg, about 50 µg to about 100 µg, about 75 µg to about 100 µg, about 1 µg to about 75 µg, about 5 µg to about 75 µg, about 10 µg to about 75 µg, about 15 µg to about 75 µg, about 25 µg to about 75 µg, about 50 µg to about 75 µg, about 1 µg to about 50 µg, about 5 µg to about 50 µg, about 10 µg to about 50 µg, about 15 µg to about 50 µg, about 25

µg to about 50 µg, about 1 µg to about 25 lag, about 5 µg to about 25 µg, about 10 µg to about 25 µg, about 15 µg to about 25 µg, about 1 µg to about 15 lag, about 5 µg to about 15 µg, about 10 µg to about 15 µg, about 1 µg to about 10 µg, about 5 µg to about 10 lag, or about 1 µg to about 5 µg per dose. In some embodiments, the vaccine or immunogenic composition includes an aluminum salt adjuvant (e.g., alum) at about 1 µg, about 5 µg, about 10 µg, about 15 µg, about 25 lag, about 50 µg, about 75 µg, about 100 µg, about 125 µg, about 150 µg, about 175 µg, about 200 µg, about 225 µg, about 250 µg, about 275 µg, about 300 µg, about 325 µg, about 350 µg, about 375 µg, about 400 lag, about 425 µg, about 450 µg, about 475 µg, or about 500 µg per dose.

Certain embodiments of the present disclosure include a method for preparing an adjuvanted Zika virus vaccine or immunogenic composition, which involves (a) mixing the vaccine or immunogenic composition with an aluminum salt adjuvant, with the vaccine or immunogenic composition including one or more antigens from at least one Zika virus described herein and (b) incubating the mixture under suitable conditions for a period of time that ranges from about 1 hour to about 24 hours (e.g., about 16 hours to about 24 hours), with at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% of the antigen adsorbed to the aluminum salt adjuvant. In certain embodiments of the method, the at least one Zika virus is a Zika virus comprising a non-human cell adaptation mutation (e.g., a non-human cell adaptation mutation in protein NS1 such as a Trp98Gly mutation). In some embodiments, the at least one Zika virus is a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59. In some embodiments, the Zika virus is a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59 comprising the genomic sequence according to SEQ ID NO:2.

In some embodiments of the method, the mixture is incubated at a temperature that ranges from about 2° C. to about 8° C. In some embodiments of the method, the mixture is incubated under constant mixing using any suitable mixer known in the art. In some embodiments of the method, the mixture is incubated at pH that ranges in value from about 6.5 to about 8.5, from about 6.5 to about 8, from about 6.8 to about 7.8, from about 6.9 to about 7.6, from about 7 to about 7.5, from about 6.8 to about 8.5, from about 6.9 to about 8.5, or from about 7 to about 8.5. In certain preferred embodiments, the mixture is incubated at a neutral pH. In some embodiments of the method, the aluminum salt adjuvant is selected from alum, aluminum phosphate, aluminum hydroxide, potassium aluminum sulfate, and Alhydrogel 85.

Monophosphoryl Lipid A (MLA), a non-toxic derivative of lipid A from *Salmonella*, is a potent TLR-4 agonist that has been developed as a vaccine adjuvant (Evans et al. (2003) Expert Rev. Vaccines 2(2): 219-229). In pre-clinical murine studies intranasal MLA has been shown to enhance secretory, as well as systemic, humoral responses (Baldridge et al. (2000) Vaccine 18(22): 2416-2425; Yang et al. (2002) Infect. Immun. 70(7): 3557-3565). It has also been proven to be safe and effective as a vaccine adjuvant in clinical studies of greater than 120,000 patients (Baldrick et al. (2002) Regul. Toxicol. Pharmacol. 35(3): 398-413; Baldrick et al. (2004) J. Appl. Toxicol. 24(4): 261-268). MLA stimulates the induction of innate immunity through the TLR-4 receptor and is thus capable of eliciting nonspecific immune responses against a wide range of infectious pathogens, including both gram negative and gram positive bacteria, viruses, and parasites (Baldrick et al. (2004) J. Appl. Toxicol. 24(4): 261-268; Persing et al. (2002) Trends Microbiol. 10(10 Suppl): S32-37). Inclusion of MLA in intranasal formulations should provide rapid induction of innate responses, eliciting nonspecific immune responses from viral challenge while enhancing the specific responses generated by the antigenic components of the vaccine.

Accordingly, in one embodiment, the present disclosure provides a composition comprising monophosphoryl lipid A (MLA), 3 De-O-acylated monophosphoryl lipid A (3D-MLA), or a derivative thereof as an enhancer of adaptive and innate immunity. Chemically 3D-MLA is a mixture of 3 De-O-acylated monophosphoryl lipid A with 4, 5 or 6 acylated chains. A preferred form of 3 De-O-acylated monophosphoryl lipid A is disclosed in European Patent 0 689 454 B1 (SmithKline Beecham Biologicals SA). In another embodiment, the present disclosure provides a composition comprising synthetic lipid A, lipid A mimetics or analogs, such as BioMira's PET Lipid A, or synthetic derivatives designed to function like TLR-4 agonists.

Additional exemplary adjuvants include, without limitation, polypeptide adjuvants that may be readily added to the antigens described herein by co-expression with the polypeptide components or fusion with the polypeptide components to produce chimeric polypeptides. Bacterial flagellin, the major protein constituent of flagella, is an adjuvant which has received increasing attention as an adjuvant protein because of its recognition by the innate immune system by the toll-like receptor TLRS. Flagellin signaling through TLRS has effects on both innate and adaptive immune functions by inducing DC maturation and migration as well as activation of macrophages, neutrophils, and intestinal epithelial cells resulting in production of pro-inflammatory mediators.

TLRS recognizes a conserved structure within flagellin monomers that is unique to this protein and is required for flagellar function, precluding its mutation in response to immunological pressure. The receptor is sensitive to a 100 fM concentration but does not recognize intact filaments. Flagellar disassembly into monomers is required for binding and stimulation.

As an adjuvant, flagellin has potent activity for induction of protective responses for heterologous antigens administered either parenterally or intranasally and adjuvant effects for DNA vaccines have also been reported. A Th2 bias is observed when flagellin is employed which would be appropriate for a respiratory virus such as influenza but no evidence for IgE induction in mice or monkeys has been observed. In addition, no local or systemic inflammatory responses have been reported following intranasal or systemic administration in monkeys. The Th2 character of responses elicited following use of flagellin is somewhat surprising since flagellin signals through TLRS in a MyD88-dependent manner and all other MyD88-dependent signals through TLRs have been shown to result in a Th1 bias. Importantly, pre-existing antibodies to flagellin have no appreciable effect on adjuvant efficacy making it attractive as a multi-use adjuvant.

A common theme in many recent intranasal vaccine trials is the use of adjuvants and/or delivery systems to improve vaccine efficacy. In one such study an influenza H3 vaccine containing a genetically detoxified E. coli heat-labile enterotoxin adjuvant (LT R192G) resulted in heterosubtypic protection against H5 challenge but only following intranasal delivery. Protection was based on the induction of cross neutralizing antibodies and demonstrated important implications for the intranasal route in development of new vaccines.

Cytokines, colony-stimulating factors (e.g., GM-CSF, CSF, and the like); tumor necrosis factor; interleukin-2, -7, -12, interferons and other like growth factors, may also be used as adjuvants as they may be readily included in the Zika virus vaccines or immunogenic compositions by admixing or fusion with the polypeptide component.

In some embodiments, the Zika virus vaccine and/or immunogenic compositions disclosed herein may include other adjuvants that act through a Toll-like receptor such as a nucleic acid TLR9 ligand comprising a 5'-TCG-3' sequence; an imidazoquinoline TLR7 ligand; a substituted guanine TLR7/8 ligand; other TLR7 ligands such as Loxoribine, 7-deazadeoxyguanosine, 7-thia-8-oxodeoxyguanosine, Imiquimod (R-837), and Resiquimod (R-848).

Certain adjuvants facilitate uptake of the vaccine molecules by APCs, such as dendritic cells, and activate these. Non-limiting examples are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminum adjuvants; DNA adjuvants; MLA; and an encapsulating adjuvant.

Additional examples of adjuvants include agents such as aluminum salts such as hydroxide or phosphate (alum), commonly used as 0.05 to 0.1 percent solution in buffered saline (see, e.g., Nicklas (1992) Res. Immunol. 143:489-493), admixture with synthetic polymers of sugars (e.g. Carbopol®) used as 0.25 percent solution, aggregation of the protein in the vaccine by heat treatment with temperatures ranging between 70° to 101° C. for 30 second to 2 minute periods respectively and also aggregation by means of cross-linking agents are possible. Aggregation by reactivation with pepsin treated antibodies (Fab fragments) to albumin, mixture with bacterial cells such as C. parvum or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Admixture with oils such as squalene and IFA may also be used.

DDA (dimethyldioctadecylammonium bromide) is an interesting candidate for an adjuvant, but also Freund's complete and incomplete adjuvants as well as quillaja saponins such as QuilA and QS21 are interesting. Further possibilities include poly[di(earboxylatophenoxy)phosphazene (PCPP) derivatives of lipopolysaccharides such as monophosphoryl lipid A (MLA), muramyl dipeptide (MDP) and threonyl muramyl dipeptide (tMDP). The lipopolysaccharide based adjuvants may also be used for producing a predominantly Th1-type response including, for example, a combination of monophosphoryl lipid A, such as 3-de-O-acylated monophosphoryl lipid A, together with an aluminum salt.

Liposome formulations are also known to confer adjuvant effects, and therefore liposome adjuvants may be used in conjunction with the Zika virus vaccines and/or immunogenic compositions.

Immunostimulating complex matrix type (ISCOM® matrix) adjuvants may also be used with the Zika virus vaccine antigens and immunogenic compositions, especially since it has been shown that this type of adjuvants are capable of up-regulating MHC Class II expression by APCs. An ISCOM matrix consists of (optionally fractionated) saponins (triterpenoids) from Quillaja saponaria, cholesterol, and phospholipid. When admixed with the immunogenic protein such as the Zika virus vaccine or immunogenic composition antigens, the resulting particulate formulation is what is known as an ISCOM particle where the saponin may constitute 60-70% w/w, the cholesterol and phospholipid 10-15% w/w, and the protein 10-15% w/w. Details relating to composition and use of immunostimulating complexes can for example be found in the above-mentioned text-books dealing with adjuvants, but also Morein B et al. (1995) Clin. Immunother. 3: 461-475 as well as Barr I G and Mitchell G F (1996) Immunol. and Cell Biol. 74: 8-25 provide useful instructions for the preparation of complete immunostimulating complexes.

The saponins, whether or not in the form of iscoms, that may be used in the adjuvant combinations with the Zika virus vaccines and immunogenic compositions disclosed herein include those derived from the bark of Quillaja Saponaria Molina, termed Quil A, and fractions thereof, described in U.S. Pat. No. 5,057,540 and "Saponins as vaccine adjuvants", Kensil, C. R. (1996) Crit Rev Ther Drug Carrier Syst 12 (1-2):1-55; and EP 0 362 279 B1. Exemplary fractions of Quil A are QS21, QS7, and QS17.

β-Escin is another hemolytic saponins for use in the adjuvant compositions of the Zika virus vaccines and/or immunogenic compositions. Escin is described in the Merck index (12th ed: entry 3737) as a mixture of saponins occurring in the seed of the horse chestnut tree, Lat: *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin have been purified and shown to be biologically active (Yoshikawa M, et al. (Chem Pharm Bull (Tokyo) 1996 August; 44(8):1454-1464)). β-escin is also known as aescin.

Another hemolytic saponin for use in the Zika virus vaccines and/or immunogenic compositions is Digitonin. Digitonin is described in the Merck index (12th Edition, entry 3204) as a saponin, being derived from the seeds of Digitalis purpurea and purified according to the procedure described Gisvold et al. (1934) J. Am. Pharm. Assoc. 23: 664; and Ruhenstroth-Bauer (1955) Physiol. Chem., 301, 621. Its use is described as being a clinical reagent for cholesterol determination.

Another interesting possibility of achieving adjuvant effect is to employ the technique described in Gosselin et al., 1992. In brief, the presentation of a relevant antigen such as an antigen in a Zika virus vaccine and/or immunogenic composition of the present disclosure can be enhanced by conjugating the antigen to antibodies (or antigen binding antibody fragments) against the FC receptors on monocytes/macrophages. Especially conjugates between antigen and anti-FCRI have been demonstrated to enhance immunogenicity for the purposes of vaccination. The antibody may be conjugated to the Zika virus vaccine or immunogenic composition antigens after generation or as a part of the generation including by expressing as a fusion to any one of the polypeptide components of the Zika virus vaccine and/or immunogenic composition antigens. Other possibilities involve the use of the targeting and immune modulating substances (e.g., cytokines). In addition, synthetic inducers of cytokines such as poly I:C may also be used.

Suitable mycobacterial derivatives may be selected from the group consisting of muramyl dipeptide, complete Freund's adjuvant, RIBI, (Ribi ImmunoChem Research Inc., Hamilton, Mont.) and a diester of trehalose such as TDM and TDE.

Examples of suitable immune targeting adjuvants include CD40 ligand and CD40 antibodies or specifically binding fragments thereof (cf. the discussion above), mannose, a Fab fragment, and CTLA-4.

Examples of suitable polymer adjuvants include a carbohydrate such as dextran, PEG, starch, mannan, and mannose; a plastic polymer; and latex such as latex beads.

Yet another interesting way of modulating an immune response is to include the immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structure and function of a lymph node. Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN, and that immune protection conferred by vaccination using a VLN surpassed conventional immunization using Ribi as an adjuvant. The technology is described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. 12-15, 1998, Seascape Resort, Aptos, Calif."

Oligonucleotides may be used as adjuvants in conjunction with the Zika virus vaccine and/or immunogenic composition antigens and may contain two or more dinucleotide CpG motifs separated by at least three or more or even at least six or more nucleotides. CpG-containing oligonucleotides (in which the CpG dinucleotide is unmethylated) induce a predominantly Th1 response. Such oligonucleotides are well known and are described, for example, in WO 96/02555, WO 99/33488 and U.S. Pat. Nos. 6,008,200 and 5,856,462.

Such oligonucleotide adjuvants may be deoxynucleotides. In certain embodiments, the nucleotide backbone in the oligonucleotide is phosphorodithioate, or a phosphorothioate bond, although phosphodiester and other nucleotide backbones such as PNA including oligonucleotides with mixed backbone linkages may also be used. Methods for producing phosphorothioate oligonucleotides or phosphorodithioate are described in U.S. Pat. Nos. 5,666,153, 5,278,302 and WO 95/26204.

Exemplary oligonucleotides have the following sequences. The sequences may contain phosphorothioate modified nucleotide backbones:

(SEQ ID NO: 3) OLIGO 1:
TCC ATG ACG TTC CTG ACG TT (CpG 1826);

(SEQ ID NO: 4) OLIGO 2:
TCT CCC AGC GTG CGC CAT (CpG 1758);

-continued
(SEQ ID NO: 5) OLIGO 3:
ACC GAT GAC GTC GCC GGT GAC GGC ACC ACG;

(SEQ ID NO: 6) OLIGO 4:
TCG TCG TTT TGT CGT TTT GTC GTT (CpG 2006);
and (SEQ ID NO: 7) OLIGO 5:
TCC ATG ACG TTC CTG ATG CT (CpG 1668)

Alternative CpG oligonucleotides include the above sequences with inconsequential deletions or additions thereto. The CpG oligonucleotides as adjuvants may be synthesized by any method known in the art (e.g., EP 468520). For example, such oligonucleotides may be synthesized utilizing an automated synthesizer. Such oligonucleotide adjuvants may be between 10-50 bases in length. Another adjuvant system involves the combination of a CpG-containing oligonucleotide and a saponin derivative particularly the combination of CpG and QS21 is disclosed in WO 00/09159.

Many single or multiphase emulsion systems have been described. One of skill in the art may readily adapt such emulsion systems for use with a Zika virus vaccine and/or immunogenic composition antigens so that the emulsion does not disrupt the antigen's structure. Oil in water emulsion adjuvants per se have been suggested to be useful as adjuvant compositions (EP 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B).

The oil emulsion adjuvants for use with the Zika virus vaccines and/or immunogenic compositions described herein may be natural or synthetic, and may be mineral or organic. Examples of mineral and organic oils will be readily apparent to one skilled in the art.

In order for any oil in water composition to be suitable for human administration, the oil phase of the emulsion system may include a metabolizable oil. The meaning of the term metabolizable oil is well known in the art. Metabolizable can be defined as "being capable of being transformed by metabolism" (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils may also be used and can include commercially available oils such as NEOBEE® and others. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and may be used with the Zika virus vaccine and/or immunogenic compositions. Squalene is a metabolizable oil virtue of the fact that it is an intermediate in the biosynthesis of cholesterol (Merck index, 10th Edition, entry no. 8619).

Exemplary oil emulsions are oil in water emulsions, and in particular squalene in water emulsions.

In addition, the oil emulsion adjuvants for use with the Zika virus vaccine and/or immunogenic compositions may include an antioxidant, such as the oil α-tocopherol (vitamin E, EP 0 382 271 B1).

WO 95/17210 and WO 99/11241 disclose emulsion adjuvants based on squalene, α-tocopherol, and TWEEN 80 ™, optionally formulated with the immunostimulants QS21 and/or 3D-MLA. WO 99/12565 discloses an improvement to these squalene emulsions with the addition of a sterol into the oil phase. Additionally, a triglyceride, such as tricaprylin (C27H50O6), may be added to the oil phase in order to stabilize the emulsion (WO 98/56414).

The size of the oil droplets found within the stable oil in water emulsion may be less than 1 micron, may be in the range of substantially 30-600 nm, substantially around 30-500 nm in diameter, or substantially 150-500 nm in diameter, and in particular about 150 nm in diameter as measured by photon correlation spectroscopy. In this regard, 80% of the oil droplets by number may be within these ranges, more than 90% or more than 95% of the oil droplets by number are within the defined size ranges. The amounts of the components present in oil emulsions are conventionally in the range of from 2 to 10% oil, such as squalene; and when present, from 2 to 10% alpha tocopherol; and from 0.3 to 3% surfactant, such as polyoxyethylene sorbitan monooleate. The ratio of oil: alpha tocopherol may be equal or less than 1 as this provides a more stable emulsion. SPAN 85 ™ may also be present at a level of about 1%. In some cases it may be advantageous that the Zika virus vaccines and/or immunogenic compositions disclosed herein will further contain a stabilizer.

The method of producing oil in water emulsions is well known to one skilled in the art. Commonly, the method includes the step of mixing the oil phase with a surfactant such as a PBS/TWEEN80® solution, followed by homogenization using a homogenizer, it would be clear to one skilled in the art that a method comprising passing the mixture twice through a syringe needle would be suitable for homogenizing small volumes of liquid. Equally, the emulsification process in microfluidizer (M110S microfluidics machine, maximum of 50 passes, for a period of 2 minutes at maximum pressure input of 6 bar (output pressure of about 850 bar)) could be adapted by one skilled in the art to produce smaller or larger volumes of emulsion. This adaptation could be achieved by routine experimentation comprising the measurement of the resultant emulsion until a preparation was achieved with oil droplets of the required diameter.

Alternatively the Zika virus vaccines and/or immunogenic compositions may be combined with vaccine vehicles composed of chitosan (as described above) or other polycationic polymers, polylactide and polylactide-coglycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM.

Additional illustrative adjuvants for use in the Zika virus vaccines and/or immunogenic compositions as described herein include SAF (Chiron, Calif., United States), MF-59 (Chiron, see, e.g., Granoff et al. (1997) Infect Immun. 65 (5):1710-1715), the SBAS series of adjuvants (e.g., SB-AS2 (an oil-in-water emulsion containing MLA and QS21); SBAS-4 (adjuvant system containing alum and MLA), available from SmithKline Beecham, Rixensart, Belgium), Detox (Enhanzyn®) (GlaxoSmithKline), RC-512, RC-522, RC-527, RC-529, RC-544, and RC-560 (GlaxoSmithKline) and other aminoalkyl glucosaminide 4-phosphates (AGPs), such as those described in pending U.S. patent application Ser. Nos. 08/853,826 and 09/074,720.

Other examples of adjuvants include, but are not limited to, Hunter's TiterMax® adjuvants (CytRx Corp., Norcross, Ga.); Gerbu adjuvants (Gerbu Biotechnik GmbH, Gaiberg, Germany); nitrocellulose (Nilsson and Larsson (1992) Res. Immunol. 143:553-557); alum (e.g., aluminum hydroxide, aluminum phosphate) emulsion based formulations including mineral oil, non-mineral oil, water-in-oil or oil-in-water emulsions, such as the Seppic ISA series of Montamide adjuvants (e.g., ISA-51, ISA-57, ISA-720, ISA-151, etc.; Seppic, Paris, France); and PROVAX® (IDEC Pharmaceuticals); OM-174 (a glucosamine disaccharide related to lipid A); Leishmania elongation factor; non-ionic block copolymers that form micelles such as CRL 1005; and Syntex Adjuvant Formulation. See, e.g., O'Hagan et al. (2001) Biomol Eng. 18(3):69-85; and "Vaccine Adjuvants: Preparation Methods and Research Protocols" D. O'Hagan, ed. (2000) Humana Press.

Other exemplary adjuvants include adjuvant molecules of the general formula:

$$HO(CH_2CH_2O)_n\text{-A-R,} \qquad (I)$$

where, n is 1-50, A is a bond or —C(O)—, R is C1-50 alkyl or Phenyl C1-50 alkyl.

One embodiment consists of a vaccine formulation comprising a polyoxyethylene ether of general formula (I), where n is between 1 and 50, 4-24, or 9; the R component is C1-50, C4-C20 alkyl, or C12 alkyl, and A is a bond. The concentration of the polyoxyethylene ethers should be in the range 0.1-20%, from 0.1-10%, or in the range 0.1-1%. Exemplary polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12th edition: entry 7717). These adjuvant molecules are described in WO 99/52549.

The polyoxyethylene ether according to the general formula (I) above may, if desired, be combined with another adjuvant. For example, an adjuvant combination may include the CpG as described above.

Further examples of suitable pharmaceutically acceptable excipients for use with the Zika virus vaccines and/or immunogenic compositions disclosed herein include water, phosphate buffered saline, isotonic buffer solutions.

Virus Purification

Further aspects of the present disclosure relate to methods of purifying Zika virus. In some embodiments, the method includes inoculating a plurality of cells with an inoculum containing a population of Zika viruses, and obtaining from one or more of the inoculated cells a Zika virus clonal isolate by plaque purification. In some embodiments, the cells are non-human cells (e.g., insect cells, mammalian cells, etc.). In some embodiments, the cells are insect cells (such as any of the mosquito cells/cell lines described herein). In some embodiments, the cells are mammalian cells (such as any of the mammalian cells/cell lines described herein). In some embodiments, the mammalian cells are monkey cells.

In some embodiments, the population of Zika virus is heterogeneous (e.g., comprising two or more genotypes). In some embodiments, the population of Zika viruses comprises a Zika virus clinical isolate (e.g., from strain PRV-ABC59) and/or one or more Zika viruses that have been previously passaged in cell culture. In some embodiments, plaque purification (e.g., as described herein) allows for the substantial and/or complete separation of a (genetically homogenous) clonal isolate from a heterogeneous viral population. In some embodiments, the monkey cells are from a VERO cell line (e.g., VERO 10-87 cells). In some embodiments, the inoculum comprises human serum. In some embodiments, the inoculum comprises one or more adventitious agents (e.g., one or more contamination viruses). In some embodiments, plaque purification (e.g., as described herein) allows for the substantial and/or complete purification of a (genetically homogenous) clonal isolate away from one or more adventitious agents.

In some embodiments, the methods described for isolating and/or purifying a Zika virus clonal includes one or more (e.g., one or more, two or more, three or more, four or more, five or more, etc.) additional plaque purifications of the Zika virus clonal isolate. In some embodiments, the methods described for isolating and/or purifying a Zika virus clonal isolate includes passaging the Zika virus clonal isolate one or more (e.g., one or more, two or more, three or more, four or more, five or more, etc.) times in cell culture (e.g., in insect cells such as a mosquito cell line and/or in mammalian cells such as a VERO cell line).

Further aspects of the present disclosure relate to methods of purifying Zika virus for the preparation of a vaccine or immunogenic composition. In some embodiments, the methods include one or more (e.g., one or more, two or more, three or more, four or more, five or more, or six) steps of (in any order, including the following order): performing depth filtration of a sample or preparation containing a Zika virus; buffer exchanging and/or diluting a sample containing a Zika virus (e.g., by cross flow filtration (CFF)) to produce a retentate; binding a sample comprising a Zika virus to an ion exchange membrane (e.g., an anion exchange membrane, a cation exchange membrane) to produce a bound fraction, where the bound fraction comprises the Zika virus, and eluting the bound fraction from the ion exchange membrane; treating a sample containing a Zika virus with an effective amount of any of the chemical inactivators described herein; neutralizing a sample containing a chemically inactivated Zika virus with sodium metabisulfite; and/or purifying a neutralized sample comprising a chemically inactivated Zika virus (e.g., by cross flow filtration (CFF)). In some embodiments, the method includes the steps of (a) passing a sample containing a Zika virus through a first depth filter to produce a first eluate, where the first eluate contains the Zika virus; (b) buffer exchanging and/or diluting the first eluate by cross flow filtration (CFF) to produce a first retentate, where the first retentate contains the Zika virus; (c) binding the first retentate to an ion exchange membrane to produce a first bound fraction, where the first bound fraction contains the Zika virus, and eluting the first bound fraction from the ion exchange membrane to produce a second eluate, where the second eluate contains the Zika virus; (d) passing the second eluate through a second depth filter to produce a second retentate, wherein the second retentate contains the Zika virus; (e) treating the second retentate with an effective amount of a chemical inactivator; (f) neutralizing the treated second retentate with sodium metabisulfite; and (g) purifying the neutralized second retentate by cross flow filtration (CFF).

Depth filters may be applied in a cartridge or capsule format, such as with the SUPRACAP™ series of depth filter capsules (Pall Corporation) using a Bio 20 SEITZ® depth filter sheet. Other suitable depth filtration techniques and apparatuses are known in the art and include Sartorius PP3 filters. In some embodiments, the depth filter has a pore size of between about 0.2 nm and about 3 nm. In some embodiments, the pore size of the depth filter is less than about any of the following pore sizes (in nm): 3, 2.8, 2.6, 2.4, 2.2, 2.0, 1.8, 1.6, 1.4, 1.2, 1.0, 0.8, 0.6, and 0.4. In some embodiments, the pore size of the depth filter is greater than about any of the following pore sizes (in nm): 0.2, 0.4, 0.6, 0.8, 1.0, 1.2, 1.4, 1.6, 1.8, 2.0, 2.2, 2.4, 2.6, or 2.8. That is, the pore size of the depth filter can be any of a range of pore sizes (in nm) having an upper limit of 3, 2.8, 2.6, 2.4, 2.2, 2.0, 1.8, 1.6, 1.4, 1.2, 1.0, 0.8, 0.6, and 0.4 and an independently selected lower limit of 0.2, 0.4, 0.6, 0.8, 1.0, 1.2, 1.4, 1.6, 1.8, 2.0, 2.2, 2.4, 2.6, or 2.8; wherein the lower limit is less than the upper limit.

As described herein, cation exchange and anion exchange chromatography may be used in the methods of the present disclosure to purify a Zika virus harvested from a cell supernatant of the present disclosure. For example, clarified viral harvest may be basified, loaded onto an anion exchange membrane, eluted by salt or pH, filtered, and inactivated. This is only an exemplary scheme, and one of skill in the art may readily contemplate variants thereof with substituted, deleted, inserted, or reordered steps.

Anion and cation exchange chromatography both rely on the attraction of charged macromolecules of interest (e.g., a virus) in a mobile phase to a substrate having an opposite charge. In cation exchange chromatography, the negatively charged substrate or membrane attracts positively charged macromolecules. In anion exchange chromatography, the positively charged substrate or membrane attracts negatively charged macromolecules. Once macromolecules are bound or loaded onto the substrate, they may be eluted in linear or step-wise fashion from the substrate in a manner dependent on their characteristics, thereby enacting a separation of differently charged molecules. This principle may be used to purify viruses from other macromolecules. Elution may be effected by varying pH or salt content of the mobile phase buffer. Elution may be gradient or step-wise. As described herein, elution may be effected using a change in pH of the mobile phase or by using a change in ionic strength of the mobile phase (e.g., through addition of a salt). A variety of salts are used for elution, including without limitation sodium chloride, potassium chloride, sodium sulphate, potassium sulphate, ammonium sulphate, sodium acetate, potassium phosphate, calcium chloride, and magnesium chloride. In certain embodiments, the salt is NaCl. A variety of suitable buffers are known in the art and described herein. Viral purification methods using ion exchange chromatography are also generally known; see, e.g., purification of influenza virus available online at Pall Corporation USA.

A variety of devices known in the art are suitable for cation exchange chromatography (optionally including filtration), such as the Mustang® S system (Pall Corporation), which uses a cation exchange membrane with a 0.65 nm pore size. A variety of functional groups are used for cation exchange membranes, including without limitation pendant sulfonic functional groups in a cross-linked, polymeric coating. A variety of buffers may be used to bind an eluate containing a Zika virus of the present disclosure to a cation exchange membrane. Exemplary buffers include, without limitation, citrate and phosphate buffers (additional buffers are described infra). In some embodiments, a buffer used in cation exchange chromatography (e.g., in loading and/or elution) contains polysorbate (e.g., TWEEN®-80 at 0.05%, 0.1%, 0.25%, or 0.5%).

A variety of devices known in the art are suitable for anion exchange chromatography (optionally including filtration), such as the Mustang® Q system (Pall Corporation), which uses an anion exchange membrane with a 0.8 nm pore size. Another suitable anion exchange membrane is SartobindQ IEXNano. A variety of functional groups are used for anion exchange membranes, including without limitation pendant quaternary amine functional groups in a cross-linked, polymeric coating. A variety of buffers may be used to bind an eluate containing a Zika virus of the present disclosure to an anion exchange membrane. Exemplary buffers include, without limitation, phosphate buffer (additional buffers are described infra). In some embodiments, a buffer used in anion exchange chromatography (e.g., in loading and/or elution) contains polysorbate (e.g., TWEEN®-80 at 0.05%, 0.1%, 0.25%, or 0.5%). In some embodiments, the virus is eluted by step elution, e.g. using 250 mM NaCl, 500 mM NaCl and 750 mM NaCl.

Formulations of Vaccines and/or Immunogenic Compositions

Further aspects of the present disclosure relate to formulations of vaccines and/or immunogenic compositions of the present disclosure containing one or more antigens from a Zika virus described herein. In some embodiments, the Zika virus is a purified inactivated whole Zika virus. In some embodiments, the purified inactivated whole Zika virus comprises a mutation at position 98 of SEQ ID NO: 1, or at a position corresponding to position 98 of SEQ ID NO:1. In some embodiments, the purified inactivated whole Zika virus comprises a Trp98Gly mutation at position 98 of SEQ ID NO: 1, or at a position corresponding to position 98 of SEQ ID NO:1. In some embodiments, the purified inactivated whole Zika virus comprises a Trp98Gly mutation at position 98 of SEQ ID NO: 1, or at a position corresponding to position 98 of SEQ ID NO:1, wherein the Zika virus is derived from strain PRVABC59. In some embodiments, the purified inactivated whole Zika virus comprises a Trp98Gly mutation at position 98 of SEQ ID NO: 1, or at a position corresponding to position 98 of SEQ ID NO:1, wherein the Zika virus is derived from strain PRVABC59 comprising the genomic sequence according to SEQ ID NO:2.

Such vaccines and/or immunogenic compositions of the present disclosure containing one or more antigens from a Zika virus described herein may be useful for treating or preventing Zika virus infection in a subject in need thereof and/or inducing an immune response, such as a protective immune response, against Zika virus in a subject in need thereof.

Typically, vaccines and/or immunogenic compositions of the present disclosure are prepared as injectables either as liquid solutions or suspensions; solid forms suitable for solution in, or suspension in, liquid prior to injection may also be prepared. Such preparations may also be emulsified or produced as a dry powder. The active immunogenic ingredient is often mixed with excipients which are pharmaceutically acceptable and compatible with the active ingredient. Suitable excipients are, for example, water, saline, dextrose, sucrose, glycerol, ethanol, or the like, and combinations thereof. In addition, if desired, the vaccine or immunogenic composition may contain auxiliary substances such as wetting or emulsifying agents, pH buffering agents, or adjuvants which enhance the effectiveness of the vaccine or immunogenic composition.

Vaccines or immunogenic compositions may be conventionally administered parenterally, by injection, for example, either subcutaneously, transcutaneously, intradermally, subdermally or intramuscularly. Additional formulations which are suitable for other modes of administration include suppositories and, in some cases, oral, peroral, intranasal, buccal, sublingual, intraperitoneal, intravaginal, anal and intracranial formulations. For suppositories, traditional binders and carriers may include, for example, polyalkalene glycols or triglycerides; such suppositories may be formed from mixtures containing the active ingredient in the range of 0.5% to 10%, or even 1-2%. In certain embodiments, a low melting wax, such as a mixture of fatty acid glycerides or cocoa butter is first melted and the Zika virus vaccine and/or immunogenic composition described herein is dispersed homogeneously, for example, by stirring. The molten homogeneous mixture is then poured into conveniently sized molds and allowed to cool and to solidify.

Formulations suitable for intranasal delivery include liquids (e.g., aqueous solution for administration as an aerosol or nasal drops) and dry powders (e.g. for rapid deposition within the nasal passage). Formulations include such normally employed excipients as, for example, pharmaceutical grades of mannitol, lactose, sucrose, trehalose, xylitol, and chitosan. Mucosadhesive agents such as chitosan can be used in either liquid or powder formulations to delay mucociliary clearance of intranasally-administered formulations. Sugars such as mannitol, sorbitol, trehalose, and/or sucrose can be used as stability agents in liquid formulations and as stability, bulking, or powder flow and size agents in dry powder formulations. In addition, adjuvants such as monophosphoryl lipid A (MLA), or derivatives thereof, or CpG oligonucleotides can be used in both liquid and dry powder formulations as an immunostimulatory adjuvant.

Formulations suitable for oral delivery include liquids, solids, semi-solids, gels, tablets, capsules, lozenges, and the like. Formulations suitable for oral delivery include tablets, lozenges, capsules, gels, liquids, food products, beverages, nutraceuticals, and the like. Formulations include such normally employed excipients as, for example, pharmaceutical grades of mannitol, sorbitol, trehalose, sucrose, lactose, starch, magnesium stearate, sodium saccharine, cellulose, magnesium carbonate, and the like. Other Zika virus vaccines and immunogenic compositions may take the form of solutions, suspensions, pills, sustained release formulations or powders and contain 10-95% of active ingredient, or 25-70%. For oral formulations, cholera toxin is an interesting formulation partner (and also a possible conjugation partner).

The Zika virus vaccines and/or immunogenic compositions when formulated for vaginal administration may be in the form of pessaries, tampons, creams, gels, pastes, foams or sprays. Any of the foregoing formulations may contain agents in addition to Zika virus vaccine and/or immunogenic compositions, such as carriers, known in the art to be appropriate.

In some embodiments, the Zika virus vaccines and/or immunogenic compositions of the present disclosure may be formulated for systemic or localized delivery. Such formulations are well known in the art. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Systemic and localized routes of administration include, e.g., intradermal, topical application, intravenous, intramuscular, etc.

The vaccines and/or immunogenic compositions of the present disclosure may be administered in a manner compatible with the dosage formulation, and in such amount as will be therapeutically effective and immunogenic. The vaccine may comprise a purified inactivated whole Zika virus, in the form of a clonal isolate obtained/obtainable from plaque purification, such as a Zika virus with a mutation which is a tryptophan to glycine substitution at position 98 of SEQ ID NO:1 or at a position corresponding to position 98 of SEQ ID NO:1 as described herein. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRV-ABC59. In some embodiments, the vaccine or immunogenic composition comprises a purified inactivated whole Zika virus comprising a Trp98Gly mutation at position 98 of SEQ ID NO: 1, or at a position corresponding to position 98 of SEQ ID NO:1, wherein the Zika virus is derived from strain PRVABC59 comprising the genomic sequence according to SEQ ID NO:2. The quantity to be administered depends on the subject to be treated, including, e.g., the capacity of the individual's immune system to mount an immune response, and the degree of protection desired. Suitable dosage ranges may include, for example, from about 0.1 µg to about 100 µg, about 1 µg to about 100 µg, about 2 µg to about 100 µg, about 5 µg to about 100 µg, about 10 µg to about 100 µg, about 15 µg to about 100 µg, about 20 µg to about 100 µg, about 25 µg to about 100 µg, about 30 µg to about 100 µg, about 35 µg to about 100 µg, about 40 µg to about 100 lag, about 45 µg to about 100 µg, about 50 µg to about 100 µg, about 55 µg to about 100 µg, about 60 µg to about 100 µg, about 65 µg to about 100 µg, 70 µg to about 100 µg, about 75 µg to about 100 µg, about 80 µg to about 100 µg, about 85 µg to about 100 µg, about 90 µg to about 100 µg, about 95 µg to about 100 µg, about 0.1 µg to about 95 µg, about 1 µg to about 95 µg, about 2 µg to about 95 µg, about 5 µg to about 95 µg, about 10 µg to about 95 µg, about 15 µg to about 95 µg, about 20 µg to about 95 µg, about 25 µg to about 95 lag, about 30 µg to about 95 µg, about 35 µg to about 95 µg, about 40 µg to about 95 µg, about 45 µg to about 95 µg, about 50 µg to about 95 µg, about 55 µg to about 95 µg, about 60 µg to about 95 µg, about 65 µg to about 95 µg, 70 µg to about 95 µg, about 75 µg to about 95 µg, about 80 µg to about 95 µg, about 85 µg to about 95 µg, about 90 µg to about 95 µg, about 0.1 µg to about 90 µg, about 1 µg to about 90 µg, about 2 µg to about 90 µg, about 5 µg to about 90 µg, about 10 µg to about 90 µg, about 15 µg to about 90 µg, about 20 lag to about 90 µg, about 25 µg to about 90 µg, about 30 µg to about 90 µg, about 35 µg to about 90 µg, about 40 µg to about 90 µg, about 45 µg to about 90 µg, about 50 µg to about 90 µg, about 55 µg to about 90 lag, about 60 µg to about 90 µg, about 65 µg to about 90 µg, 70 µg to about 90 µg, about 75 µg to about 90 µg, about 80 µg to about 90 µg, about 85 µg to about 90 µg, about 0.1 µg to about 85 µg, about 1 µg to about 85 lag, about 2 µg to about 85 µg, about 5 µg to about 85 µg, about 10 µg to about 85 µg, about 15 µg to about 85 lag, about 20 µg to about 85 µg, about 25 µg to about 85 µg, about 30 µg to about 85 µg, about 35 µg to about 85 µg, about 40 µg to about 85 µg, about 45 µg to about 85 µg, about 50 µg to about 85 µg, about 55 µg to about 85 µg, about 60 µg to about 85 µg, about 65 µg to about 85 µg, 70 µg to about 85 µg, about 75 µg to about 85 µg, about 80 µg to about 85 µg, about 0.1 µg to about 80 µg, about 1 µg to about 80 µg, about 2 µg to about 80 µg, about 5 µg to about 80 µg, about 10 µg to about 80 µg, about 15 µg to about 80 µg, about 20 lag to about 80 µg, about 25 µg to about 80 µg, about 30 µg to about 80 µg, about 35 µg to about 80 µg, about 40 µg to about 80 µg, about 45 µg to about 80 µg, about 50 µg to about 80 µg, about 55 µg to about 80 lag, about 60 µg to about 80 µg, about 65 µg to about 80 µg, 70 µg to about 80 µg, about 75 µg to about 80 µg, about 0.1 µg to about 75 µg, about 1 µg to about 75 µg, about 2 µg to about 75 µg, about 5 µg to about 75 µg, about 10 µg to about 75 µg, about 15 µg to about 75 µg, about 20 µg to about 75 µg, about 25 µg to about 75 lag, about 30 µg to about 75 µg, about 35 µg to about 75 µg, about 40 µg to about 75 µg, about 45 µg to about 75 µg, about 50 µg to about 75 µg, about 55 µg to about 75 µg, about 60 µg to about 75 µg, about 65 µg to about 75 µg, 70 µg to about 75 µg, about 0.1 µg to about 70 µg, about 1 µg to about 70 µg, about 2 µg to about 70 µg, about 5 µg to about 70 µg, about 10 µg to about 70 µg, about 15 µg to about 70 µg, about 20 µg to about 70 µg, about 25 µg to about 70 µg, about 30 µg to about 70 µg, about 35 µg to about 70 µg, about 40 lag to about 70 µg, about 45 µg to about 70 µg, about 50 µg to about 70 µg, about 55 µg to about 70 µg, about 60 µg to about 70 µg, about 65 µg to about 70 µg, about 0.1 µg to about 65 µg, about 1 µg to about 65 µg, about 2 µg to about 65 µg, about 5 µg to about 65 µg, about 10 µg to about 65 µg, about 15 µg to about 65 µg, about 20 µg to about 65 µg, about 25 µg to about 65 µg, about 30 µg to about 65 µg, about 35 µg to about 65 lag, about 40 µg to about 65 µg, about 45 µg to about 65 µg, about 50 µg to about 65 µg, about 55 µg to about 65 µg, about 60 µg to about 65 µg, about 0.1 µg to about 60 µg, about 1 µg to about 60 µg, about 2 µg to about 60 µg, about 5 µg to about 60 µg, about 10 µg to about 60 µg, about 15 µg to about 60 µg, about 20 µg to about 60 µg, about 25 µg to about 60 µg, about 30 µg to about 60 µg, about 35 µg to about 60 µg, about 40 lag to about 60 µg, about 45 µg to about 60 µg, about 50 µg to about 60 µg, about 55 µg to about 60 µg, about 0.1 µg to about 55 µg, about 1 µg to about 55 µg, about 2 µg to about 55 µg, about 5 µg to about 55 µg, about 10 µg to about 55 µg, about 15 µg to about 55 µg, about 20 µg to about 55 µg, about 25 µg to about 55 lag, about 30 µg to about 55 µg, about 35 µg to about 55 µg, about 40 µg to about 55 µg, about 45 µg to about 55 lag, about 50 µg to about 55 µg, about 0.1 µg to about 50 µg, about 1 µg to about 50 µg, about 2 µg to about 50 µg, about 5 µg to about 50 µg, about 10 µg to about 50 µg, about 15 µg to about 50 µg, about 20 µg to about 50 µg, about 25 µg to about 50 µg, about 30 µg to about 50 µg, about 35 µg to about 50 µg, about 40 µg to about 50 µg, about 45 µg to about 50 µg, about 0.1 µg to about 45 µg, about 1 µg to about 45 µg, about 2 lag to about 45 µg, about 5 µg to about 45 µg, about 10 µg to about 45 µg, about 15 µg to about 45 µg, about 20 µg to about 45 µg, about 25 µg to about 45 µg, about 30 µg to about 45 µg, about 35 µg to about 45 lag, about 40 µg to about 45 µg, about 0.1 µg to about 40 µg, about 1 µg to about 40 µg, about 2 µg to about 40 lag, about 5 µg to about 40 µg, about 10 µg to about 40 µg, about 15 µg to about 40 µg, about 20 µg to about 40 µg, about 25 µg to about 40 µg, about 30 µg to about 40 µg, about 35 µg to about 40 µg, about 0.1 µg to about 35 µg, about 1 µg to about 35 µg, about 2 µg to about 35 µg, about 5 µg to about 35 µg, about 10 µg to about 35 µg, about 15 µg to about 35 µg, about 20 µg to about 35 µg, about 25 µg to about 35 µg, about 30 µg to about 35 µg, about 0.1 µg to about 30 µg, about 1 µg to about 30 µg, about 2 µg to about 30 lag, about 5 µg to about 30 µg, about 10 µg to about 30 µg, about 15 µg to about 30 µg, about 20 µg to about 30 lag, about 25 µg to about 30 µg, about 0.1 µg to about 25 µg, about 1 µg to about 25 µg, about 2 µg to about 25 µg, about 5 µg to about 25 µg, about 10 µg to about 25 µg, about 15 µg to about 25 µg, about 20 µg to about 25 µg, about 0.1 µg to about 20 µg, about 1 µg to about 20 µg, about 2 µg to about 20 µg, about 5 µg to about 20 µg, about 10 µg to about 20 µg, about 15 µg to about 20 µg, about 0.1 µg to about 15 µg, about 1 µg to about 15 µg, about 2 µg to about 15 µg, about 5 µg to about 15 µg, about 10 µg to about 15 µg, about 0.1 lag to about 10 µg, about 1 µg to about 10 µg, about 2 µg to about 10 µg, about 5 µg to about 10 µg, about 0.1 µg to about 5 µg, about 1 µg to about 5 µg, about 2 µg to about 5 µg, about 0.1 µg to about 2 µg, about 1 lag to about 2 µg, or about 0.1 µg to about 1 µg per dose. In certain embodiments, the dosage can be about 0.1 lag, about 0.2 µg, about 0.3 µg, about 0.4 µg, about 0.5 µg, about 0.6 µg, about 0.7 µg, about 0.8 µg, about 0.9 lag, about 1 µg, about 1.1 µg, about 1.2 µg, about 1.3 µg, about 1.4 µg, about 1.5 µg, about 1.6 µg, about 1.7 lag, about 1.8 µg, about 1.9 µg, about 2 µg, about 2.1 µg, about 2.2 µg, about 2.3 µg, about 2.4 µg, about 2.5 lag, about 2.6 µg, about 2.7 µg, about 2.8 µg, about 2.9 µg, about 3 µg, about 4 µg, about 5 µg, about 6 µg, about 7 µg, about 8 µg, about 9 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 lag, about 24 µg, about 25 µg, about 26 µg, about 27 µg, about 28 µg, about 29 µg, about 30 µg, about 31 µg, about 32 µg, about 33 µg, about 34 µg, about 35 µg, about 36 µg, about 37 µg, about 38 µg, about 39 µg, about 40 µg, about 41 µg, about 42 µg, about 43 µg, about 44 µg, about 45 µg, about 46 µg, about 47 µg, about 48 µg, about 49 µg, about 50 µg, about 51 µg, about 52 µg, about 53 µg, about 54 µg, about 55 µg, about 56 µg, about 57 µg, about 58 µg, about 59 µg, about 60 µg, about 61 µg, about 62 µg, about 63 µg, about 64 µg, about 65 µg, about 66 µg, about 67 µg, about 68 µg, about 69 µg, about 70 µg, about 71 µg, about 72 µg, about 73 µg, about 74 µg, about 75 µg, about 76 µg, about 77 µg, about 78 µg, about 79 µg, about 80 µg, about 81 µg, about 82 µg, about 83 µg, about 84 µg, about 85 µg, about 86 µg, about 87 µg, about 88 µg, about 89 µg, about 90 µg, about 91 µg, about 92 µg, about 93 µg, about 94 µg, about 95 µg, about 96 µg, about 97 µg, about 98 µg, about 99 µg, or about 100 µg per dose. The amount of the purified inactivated Zika virus can be determined by a Bradford assay (Bradford et al. (1976) Anal. Biochem. 72: 248-254) using defined amounts of recombinant Zika envelope protein to establish the standard curve. Thus the dosage of the antigen may thus also be referred to as micrograms (µg) of Zika Envelope protein E (µg Env). µg Antigen as mentioned above in this paragraph and µg Env as mentioned in the paragraph below thus mean the same within the meaning of this disclosure.

In some embodiments, the dosage may be measured in micrograms (µg) of Zika Envelope protein E (Env). Accordingly, in some embodiments, the dosage ranges may include, for example, from about 0.1 µg Env to about 100 µg Env, about 1 µg Env to about 100 µg Env, about 2 µg Env to about 100 µg Env, about 5 µg Env to about 100 µg Env, about 10 µg Env to about 100 µg Env, about 15 µg Env to about 100 µg Env, about 20 µg Env to about 100 µg Env, about 25 µg Env to about 100 µg Env, about 30 µg Env to about 100 µg Env, about 35 µg Env to about 100 µg Env, about 40 µg Env to about 100 µg Env, about 45 µg Env to about 100 µg Env, about 50 µg Env to about 100 µg Env, about 55 µg Env to about 100 µg Env, about 60 µg Env to about 100 µg Env, about 65 µg Env to about 100 µg Env, 70 µg Env to about 100 µg Env, about 75 µg Env to about 100 µg Env, about 80 µg Env to about 100 µg Env, about 85 µg Env to about 100 µg Env, about 90 µg Env to about 100 µg Env, about 95 µg Env to about 100 µg Env, about 0.1 µg Env to about 95 µg Env, about 1 µg Env to about 95 µg Env, about 2 µg Env to about 95 µg Env, about 5 µg Env to about 95 µg Env, about 10 µg Env to about 95 µg Env, about 15 µg Env to about 95 µg Env, about 20 µg Env to about 95 µg Env, about 25 µg Env to about 95 µg Env, about 30 µg Env to about 95 µg Env, about 35 µg Env to about 95 lag Env, about 40 µg Env to about 95 µg Env, about 45 µg Env to about 95 µg Env, about 50 µg Env to about 95 µg Env, about 55 µg Env to about 95 µg Env, about 60 µg Env to about 95 µg Env, about 65 µg Env to about 95 µg Env, 70 µg Env to about 95 µg Env, about 75 µg Env to about 95 µg Env, about 80 µg Env to about 95 µg Env, about 85 µg Env to about 95 µg Env, about 90 µg Env to about 95 µg Env, about 0.1 µg Env to about 90 µg Env, about 1 µg Env to about 90 µg Env, about 2 µg Env to about 90 µg Env, about 5 µg Env to about 90 µg Env, about 10 µg Env to about 90 µg Env, about 15 µg Env to about 90 µg Env, about 20 µg Env to about 90 µg Env, about 25 µg Env to about 90 µg Env, about 30 µg Env to about 90 µg Env, about 35 lag Env to about 90 µg Env, about 40 µg Env to about 90 µg Env, about 45 µg Env to about 90 µg Env, about 50 µg Env to about 90 µg Env, about 55 µg Env to about 90 µg Env, about 60 µg Env to about 90 µg Env, about 65 µg Env to about 90 µg Env, 70 µg Env to about 90 µg Env, about 75 µg Env to about 90 µg Env, about 80 µg Env to about 90 µg Env, about 85 µg Env to about 90 µg Env, about 0.1 µg Env to about 85 µg Env, about 1 µg Env to about 85 µg Env, about 2 µg Env to about 85 µg Env, about 5 µg Env to about 85 lag Env, about 10 µg Env to about 85 µg Env, about 15 µg Env to about 85 µg Env, about 20 µg Env to about 85 lag Env, about 25 µg Env to about 85 µg Env, about 30 µg Env to about 85 µg Env, about 35 µg Env to about 85 µg Env, about 40 µg Env to about 85 µg Env, about 45 µg Env to about 85 µg Env, about 50 µg Env to about 85 µg Env, about 55 µg Env to about 85 µg Env, about 60 µg Env to about 85 µg Env, about 65 µg Env to about 85 µg Env, 70 µg Env to about 85 µg Env, about 75 µg Env to about 85 µg Env, about 80 µg Env to about 85 µg Env, about 0.1 µg Env to about 80 µg Env, about 1 µg Env to about 80 µg Env, about 2 µg Env to about 80 µg Env, about 5 µg Env to about 80 µg Env, about 10 µg Env to about 80 µg Env, about 15 µg Env to about 80 µg Env, about 20 µg Env to about 80 µg Env, about 25 µg Env to about 80 µg Env, about 30 lag Env to about 80 µg Env, about 35 µg Env to about 80 µg Env, about 40 µg Env to about 80 µg Env, about 45 µg Env to about 80 µg Env, about 50 µg Env to about 80 µg Env, about 55 µg Env to about 80 µg Env, about 60 µg Env to about 80 µg Env, about 65 µg Env to about 80 µg Env, 70 µg Env to about 80 µg Env, about 75 µg Env to about 80 µg Env, about 0.1 µg Env to about 75 µg Env, about 1 µg Env to about 75 µg Env, about 2 µg Env to about 75 µg Env, about 5 µg Env to about 75 µg Env, about 10 µg Env to about 75 lag Env, about 15 µg Env to about 75 µg Env, about 20 µg Env to about 75 µg Env, about 25 µg Env to about 75 lag Env, about 30 µg Env to about 75 µg Env, about 35 µg Env to about 75 µg Env, about 40 µg Env to about 75 µg Env, about 45 µg Env to about 75 µg Env, about 50 µg Env to about 75 µg Env, about 55 µg Env to about 75 µg Env, about 60 µg Env to about 75 µg Env, about 65 µg Env to about 75 µg Env, 70 µg Env to about 75 µg Env, about 0.1 µg Env to about 70 µg Env, about 1 µg Env to about 70 µg Env, about 2 µg Env to about 70 µg Env, about 5 µg Env to about 70 µg Env, about 10 µg Env to about 70 µg Env, about 15 µg Env to about 70 µg Env, about 20 µg Env to about 70 µg Env, about 25 µg Env to about 70 µg Env, about 30 lag Env to about 70 µg Env, about 35 µg Env to about 70 µg Env, about 40 µg Env to about 70 µg Env, about 45 µg Env to about 70 µg Env, about 50 µg Env to about 70 µg Env, about 55 µg Env to about 70 µg Env, about 60 µg Env to about 70 µg Env, about 65 µg Env to about 70 µg Env, about 0.1 µg Env to about 65 µg Env, about 1 µg Env to about 65 µg Env, about 2 µg Env to about 65 µg Env, about 5 µg Env to about 65 µg Env, about 10 µg Env to about 65 µg Env, about 15 µg Env to about 65 µg Env, about 20 µg Env to about 65 lag Env, about 25 µg Env to about 65 µg Env, about 30 µg Env to about 65 µg Env, about 35 µg Env to about 65 μg Env, about 40 μg Env to about 65 μg Env, about 45 μg Env to about 65 μg Env, about 50 μg Env to about 65 μg Env, about 55 μg Env to about 65 μg Env, about 60 μg Env to about 65 μg Env, about 0.1 μg Env to about 60 μg Env, about 1 μg Env to about 60 μg Env, about 2 μg Env to about 60 μg Env, about 5 μg Env to about 60 μg Env, about 10 μg Env to about 60 μg Env, about 15 μg Env to about 60 μg Env, about 20 μg Env to about 60 μg Env, about 25 μg Env to about 60 μg Env, about 30 μg Env to about 60 μg Env, about 35 lag Env to about 60 μg Env, about 40 μg Env to about 60 μg Env, about 45 μg Env to about 60 μg Env, about 50 μg Env to about 60 μg Env, about 55 μg Env to about 60 μg Env, about 0.1 μg Env to about 55 μg Env, about 1 μg Env to about 55 μg Env, about 2 μg Env to about 55 μg Env, about 5 μg Env to about 55 μg Env, about 10 μg Env to about 55 μg Env, about 15 μg Env to about 55 μg Env, about 20 μg Env to about 55 μg Env, about 25 μg Env to about 55 μg Env, about 30 μg Env to about 55 μg Env, about 35 μg Env to about 55 lag Env, about 40 μg Env to about 55 μg Env, about 45 μg Env to about 55 μg Env, about 50 μg Env to about 55 μg Env, about 0.1 μg Env to about 50 μg Env, about 1 μg Env to about 50 μg Env, about 2 μg Env to about 50 μg Env, about 5 μg Env to about 50 μg Env, about 10 μg Env to about 50 μg Env, about 15 μg Env to about 50 μg Env, about 20 μg Env to about 50 μg Env, about 25 μg Env to about 50 μg Env, about 30 μg Env to about 50 μg Env, about 35 μg Env to about 50 μg Env, about 40 μg Env to about 50 μg Env, about 45 lag Env to about 50 μg Env, about 0.1 μg Env to about 45 μg Env, about 1 μg Env to about 45 μg Env, about 2 μg Env to about 45 μg Env, about 5 μg Env to about 45 μg Env, about 10 μg Env to about 45 μg Env, about 15 μg Env to about 45 μg Env, about 20 μg Env to about 45 μg Env, about 25 μg Env to about 45 μg Env, about 30 μg Env to about 45 μg Env, about 35 μg Env to about 45 μg Env, about 40 μg Env to about 45 μg Env, about 0.1 μg Env to about 40 μg Env, about 1 μg Env to about 40 μg Env, about 2 μg Env to about 40 lag Env, about 5 μg Env to about 40 μg Env, about 10 μg Env to about 40 μg Env, about 15 μg Env to about 40 μg Env, about 20 μg Env to about 40 μg Env, about 25 μg Env to about 40 μg Env, about 30 μg Env to about 40 μg Env, about 35 μg Env to about 40 μg Env, about 0.1 μg Env to about 35 μg Env, about 1 μg Env to about 35 μg Env, about 2 μg Env to about 35 μg Env, about 5 μg Env to about 35 μg Env, about 10 lag Env to about 35 μg Env, about 15 μg Env to about 35 μg Env, about 20 μg Env to about 35 μg Env, about 25 μg Env to about 35 μg Env, about 30 μg Env to about 35 μg Env, about 0.1 μg Env to about 30 μg Env, about 1 μg Env to about 30 μg Env, about 2 μg Env to about 30 μg Env, about 5 μg Env to about 30 lag Env, about 10 μg Env to about 30 μg Env, about 15 μg Env to about 30 μg Env, about 20 μg Env to about 30 lag Env, about 25 μg Env to about 30 μg Env, about 0.1 μg Env to about 25 μg Env, about 1 μg Env to about 25 μg Env, about 2 μg Env to about 25 μg Env, about 5 μg Env to about 25 μg Env, about 10 μg Env to about 25 μg Env, about 15 μg Env to about 25 μg Env, about 20 μg Env to about 25 μg Env, about 0.1 μg Env to about 20 μg Env, about 1 μg Env to about 20 μg Env, about 2 μg Env to about 20 μg Env, about 5 μg Env to about 20 μg Env, about 10 μg Env to about 20 μg Env, about 15 μg Env to about 20 μg Env, about 0.1 μg Env to about 15 μg Env, about 1 μg Env to about 15 μg Env, about 2 μg Env to about 15 μg Env, about 5 μg Env to about 15 μg Env, about 10 μg Env to about 15 μg Env, about 0.1 μg Env to about 10 μg Env, about 1 μg Env to about 10 μg Env, about 2 μg Env to about 10 μg Env, about 5 μg Env to about 10 μg Env, about 0.1 lag Env to about 5 μg Env, about 1 μg Env to about 5 μg Env, about 2 μg Env to about 5 μg Env, about 0.1 μg Env to about 2 μg Env, about 1 μg Env to about 2 μg Env, or about 0.1 μg Env to about 1 μg Env per dose. In certain embodiments, the dosage can be about 0.1 μg Env, about 0.2 μg Env, about 0.3 μg Env, about 0.4 μg Env, about 0.5 μg Env, about 0.6 μg Env, about 0.7 μg Env, about 0.8 μg Env, about 0.9 μg Env, about 1 μg Env, about 1.1 μg Env, about 1.2 μg Env, about 1.3 μg Env, about 1.4 μg Env, about 1.5 μg Env, about 1.6 μg Env, about 1.7 μg Env, about 1.8 μg Env, about 1.9 μg Env, about 2 μg Env, about 2.1 μg Env, about 2.2 lag Env, about 2.3 μg Env, about 2.4 μg Env, about 2.5 μg Env, about 2.6 μg Env, about 2.7 μg Env, about 2.8 μg Env, about 2.9 μg Env, about 3 μg Env, about 4 μg Env, about 5 μg Env, about 6 μg Env, about 7 μg Env, about 8 μg Env, about 9 μg Env, about 10 μg Env, about 11 μg Env, about 12 μg Env, about 13 μg Env, about 14 μg Env, about 15 μg Env, about 16 μg Env, about 17 μg Env, about 18 μg Env, about 19 μg Env, about 20 lag Env, about 21 μg Env, about 22 μg Env, about 23 μg Env, about 24 μg Env, about 25 μg Env, about 26 μg Env, about 27 μg Env, about 28 μg Env, about 29 μg Env, about 30 μg Env, about 31 μg Env, about 32 lag Env, about 33 μg Env, about 34 μg Env, about 35 μg Env, about 36 μg Env, about 37 μg Env, about 38 μg Env, about 39 μg Env, about 40 μg Env, about 41 μg Env, about 42 μg Env, about 43 μg Env, about 44 lag Env, about 45 μg Env, about 46 μg Env, about 47 μg Env, about 48 μg Env, about 49 μg Env, about 50 μg Env, about 51 μg Env, about 52 μg Env, about 53 μg Env, about 54 μg Env, about 55 μg Env, about 56 μg Env, about 57 μg Env, about 58 μg Env, about 59 μg Env, about 60 μg Env, about 61 μg Env, about 62 μg Env, about 63 μg Env, about 64 μg Env, about 65 μg Env, about 66 μg Env, about 67 μg Env, about 68 μg Env, about 69 μg Env, about 70 μg Env, about 71 μg Env, about 72 μg Env, about 73 μg Env, about 74 μg Env, about 75 μg Env, about 76 μg Env, about 77 μg Env, about 78 μg Env, about 79 μg Env, about 80 μg Env, about 81 μg Env, about 82 μg Env, about 83 μg Env, about 84 μg Env, about 85 μg Env, about 86 μg Env, about 87 μg Env, about 88 μg Env, about 89 μg Env, about 90 μg Env, about 91 μg Env, about 92 lag Env, about 93 μg Env, about 94 μg Env, about 95 μg Env, about 96 μg Env, about 97 μg Env, about 98 μg Env, about 99 μg Env, or about 100 μg Env per dose.

Suitable regimens for initial administration and booster shots are also variable but are typified by an initial administration followed by subsequent inoculations or other administrations. The manner of application may be varied widely. Any of the conventional methods for administration of a vaccine or immunogenic composition are applicable. These include oral application on a solid physiologically acceptable base or in a physiologically acceptable dispersion, parenterally, by injection or the like. The dosage of the vaccine or immunogenic composition will depend on the route of administration and may vary according to the age of the person to be vaccinated and the formulation of the antigen. The vaccine or immunogenic composition can have a unit dosage volume of more than 0.5 mL, of 0.5 mL or of less than 0.5 mL, as described herein. For instance, it can be administered at a volume of 0.25 mL.

Delivery agents that improve mucoadhesion can also be used to improve delivery and immunogenicity especially for intranasal, oral or lung based delivery formulations. One such compound, chitosan, the N-deacetylated form of chitin, is used in many pharmaceutical formulations. It is an attractive mucoadhesive agent for intranasal vaccine delivery due to its ability to delay mucociliary clearance and allow more time for mucosal antigen uptake and processing. In addition, it can transiently open tight junctions which may enhance transepithelial transport of antigen to the NALT. In a recent human trial, a trivalent inactivated influenza vaccine administered intranasally with chitosan but without any additional adjuvant yielded seroconversion and HI titers that were only marginally lower than those obtained following intramuscular inoculation.

Chitosan can also be formulated with adjuvants that function well intranasally such as the genetically detoxified E. coli heat-labile enterotoxin mutant LTK63. This adds an immunostimulatory effect on top of the delivery and adhesion benefits imparted by chitosan resulting in enhanced mucosal and systemic responses.

Finally, it should be noted that chitosan formulations can also be prepared in a dry powder format that has been shown to improve vaccine stability and result in a further delay in mucociliary clearance over liquid formulations. This was seen in a recent human clinical trial involving an intranasal dry powder diphtheria toxoid vaccine formulated with chitosan in which the intranasal route was as effective as the traditional intramuscular route with the added benefit of secretory IgA responses. The vaccine was also very well tolerated. Intranasal dry powdered vaccines for anthrax containing chitosan and MLA, or derivatives thereof, induce stronger responses in rabbits than intramuscular inoculation and are also protective against aerosol spore challenge.

Intranasal vaccines represent an exemplary formulation as they can affect the upper and lower respiratory tracts in contrast to parenterally administered vaccines which are better at affecting the lower respiratory tract. This can be beneficial for inducing tolerance to allergen-based vaccines and inducing immunity for pathogen-based vaccines.

In addition to providing protection in both the upper and lower respiratory tracts, intranasal vaccines avoid the complications of needle inoculations and provide a means of inducing both mucosal and systemic humoral and cellular responses via interaction of particulate and/or soluble antigens with nasopharyngeal-associated lymphoid tissues (NALT).

Vaccines and/or immunogenic compositions of the present disclosure are pharmaceutically acceptable. They may include components in addition to the antigen and adjuvant, e.g. they will typically include one or more pharmaceutical carrier(s) and/or excipient(s). A thorough discussion of such components is available in Gennaro (2000) Remington: The Science and Practice of Pharmacy. 20th edition, ISBN: 0683306472.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccines and/or immunogenic compositions of the present disclosure may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range The pH of a vaccine or immunogenic composition will generally be between 5.0 and 8.5 or 5.0 and 8.1, and more typically between 6.0 and 8.5 e.g. between 6.0 and 8.0, between 6.5 and 8.0, between 6.5 and 7.5, between 7.0 and 8.5, between 7.0 and 8.0, or between 7.0 and 7.8. A manufacturing process of the present disclosure may therefore include a step of adjusting the pH of the bulk vaccine prior to packaging.

The vaccine or immunogenic composition is preferably sterile. It is preferably non pyrogenic, e.g. containing <1 EU (endotoxin unit, a standard measure) per dose, and preferably <0.1 EU per dose. It is preferably gluten free.

In certain embodiments, the vaccines and/or immunogenic compositions of the present disclosure may include a detergent in an effective concentration. In some embodiments, an effective amount of detergent may include without limitation, about 0.00005% v/v to about 5% v/v or about 0.0001% v/v to about 1% v/v. In certain embodiments, an effective amount of detergent is about 0.001% v/v, about 0.002% v/v, about 0.003% v/v, about 0.004% v/v, about 0.005% v/v, about 0.006% v/v, about 0.007% v/v, about 0.008% v/v, about 0.009% v/v, or about 0.01% v/v. Without wishing to be bound by theory, detergents help maintain the vaccines and/or immunogenic compositions of the present disclosure in solution and help to prevent the vaccines and/or immunogenic compositions from aggregating.

Suitable detergents include, for example, polyoxyethylene sorbitan ester surfactant (known as 'Tweens'), octoxynol (such as octoxynol-9 (Triton X 100) or t-octylphenoxypolyethoxyethanol), cetyl trimethyl ammonium bromide ('CTAB'), and sodium deoxycholate, particularly for a split or surface antigen vaccine. The detergent may be present only at trace amounts. Other residual components in trace amounts could be antibiotics (e.g. neomycin, kanamycin, polymyxin B). In some embodiments, the detergent contains polysorbate. In some embodiments, the effective concentration of detergent includes ranges from about 0.00005% v/v to about 5% v/v.

The vaccines and/or immunogenic compositions are preferably stored at between 2° C. and 8° C. They should ideally be kept out of direct light. The antigen and emulsion will typically be in admixture, although they may initially be presented in the form of a kit of separate components for extemporaneous admixing. Vaccines and/or immunogenic compositions will generally be in aqueous form when administered to a subject.

Methods of the Present Disclosure

Further aspects of the present disclosure relate to methods for using vaccines and/or or immunogenic compositions described herein containing one or more antigens from at least one Zika virus (e.g., a clonal Zika virus isolate, a Zika virus comprising a non-human cell adaptation mutation such as a non-human cell adaptation mutation in protein NS1 such as a purified inactivated whole Zika virus, in the form of a clonal isolate obtained/obtainable from plaque purification, such as a Zika virus with a mutation which is a tryptophan to glycine substitution at position 98 of SEQ ID NO:1 or at a position corresponding to position 98 of SEQ ID NO:1 as described herein) to treat or prevent Zika virus in a subject in need thereof and/or to induce an immune response to Zika virus in a subject in need thereof. Further aspects of the present disclosure relate to methods for using vaccines and/or or immunogenic compositions described herein containing a purified inactivated whole Zika virus with a mutation which is a tryptophan to glycine substitution at position 98 of SEQ ID NO:1 or at a position corresponding to position 98 of SEQ ID NO:1 to treat or prevent Zika virus in a subject in need thereof and/or to induce an immune response to Zika virus in a subject in need thereof. Further aspects of the present disclosure relate to methods for using vaccines and/or or immunogenic compositions described herein containing a purified inactivated whole Zika virus with a mutation which is a tryptophan to glycine substitution at position 98 of SEQ ID NO:1 or at a position corresponding to position 98 of SEQ ID NO:1, wherein the Zika virus is derived from strain PRVABC59, to treat or prevent Zika virus in a subject in need thereof and/or to induce an immune response to Zika virus in a subject in need thereof. Further aspects of the present disclosure relate to methods for using vaccines and/or or immunogenic compositions described herein containing a purified inactivated whole Zika virus with a mutation which is a tryptophan to glycine substitution at position 98 of SEQ ID NO:1 or at a position corresponding to position 98 of SEQ ID NO:1, wherein the Zika virus is derived from strain PRVABC59 comprising the genomic sequence according to SEQ ID NO:2 to treat or prevent Zika virus in a subject in need thereof and/or to induce an immune response to Zika virus in a subject in need thereof.

In some embodiments, the present disclosure relates to methods for treating or preventing Zika virus infection in a subject in need thereof by administering to the subject a therapeutically effective amount of a vaccine and/or immunogenic composition of the present disclosure containing one or more antigens from at least one Zika virus (e.g., a clonal Zika virus isolate, a Zika virus comprising a non-human cell adaptation mutation such as a non-human cell adaptation mutation in protein NS1, such as a purified inactivated whole Zika virus, in the form of a clonal isolate obtained/obtainable from plaque purification, such as a Zika virus with a mutation which is a tryptophan to glycine substitution at position 98 of SEQ ID NO:1 or at a position corresponding to position 98 of SEQ ID NO:1 as described herein).

In some embodiments, the present disclosure relates to methods for treating or preventing Zika virus infection in a subject in need thereof by administering to the subject a therapeutically effective amount of a vaccine and/or immunogenic composition of the present disclosure containing a purified inactivated whole Zika virus with a mutation which is a tryptophan to glycine substitution at position 98 of SEQ ID NO:1 or at a position corresponding to position 98 of SEQ ID NO:1. In some embodiments, the present disclosure relates to methods for treating or preventing Zika virus infection in a subject in need thereof by administering to the subject a therapeutically effective amount of a vaccine and/or immunogenic composition of the present disclosure containing a purified inactivated whole Zika virus with a mutation which is a tryptophan to glycine substitution at position 98 of SEQ ID NO:1 or at a position corresponding to position 98 of SEQ ID NO:1, wherein the Zika virus is derived from strain PRVABC59. In some embodiments, the present disclosure relates to methods for treating or preventing Zika virus infection in a subject in need thereof by administering to the subject a therapeutically effective amount of a vaccine and/or immunogenic composition of the present disclosure containing a purified inactivated whole Zika virus with a mutation which is a tryptophan to glycine substitution at position 98 of SEQ ID NO:1 or at a position corresponding to position 98 of SEQ ID NO:1, wherein the Zika virus is derived from strain PRVABC59 comprising the genomic sequence according to SEQ ID NO:2.

In some embodiments, the present disclosure relates to methods for inducing an immune response to Zika virus in a subject in need thereof by administering to the subject a therapeutically effective amount of a vaccine and/or or immunogenic composition of the present disclosure containing one or more antigens from at least one Zika (e.g., a clonal Zika virus isolate, a Zika virus comprising a non-human cell adaptation mutation such as a non-human cell adaptation mutation in protein NS1, such as a purified inactivated whole Zika virus, in the form of a clonal isolate obtained/obtainable from plaque purification, such as a Zika virus with a mutation which is a tryptophan to glycine substitution at position 98 of SEQ ID NO:1 or at a position corresponding to position 98 of SEQ ID NO:1 as described herein). In some embodiments, the present disclosure relates to methods for inducing an immune response to Zika virus in a subject in need thereof by administering to the subject a therapeutically effective amount of a vaccine and/or or immunogenic composition of the present disclosure containing a purified inactivated whole Zika virus with a mutation which is a tryptophan to glycine substitution at position 98 of SEQ ID NO:1 or at a position corresponding to position 98 of SEQ ID NO:1, wherein the Zika virus is derived from strain PRVABC59. In some embodiments, the present disclosure relates to methods for inducing an immune response to Zika virus in a subject in need thereof by administering to the subject a therapeutically effective amount of a vaccine and/or or immunogenic composition of the present disclosure containing a purified inactivated whole Zika virus with a mutation which is a tryptophan to glycine substitution at position 98 of SEQ ID NO:1 or at a position corresponding to position 98 of SEQ ID NO:1, wherein the Zika virus is derived from strain PRVABC59 comprising the genomic sequence according to SEQ ID NO:2.

In some embodiments, the administering step induces a protective immune response against Zika virus in the subject. In some embodiments, the subject is a human. In some embodiments, the subject is pregnant or intends to become pregnant.

The Zika virus vaccines and/or immunogenic compositions disclosed herein may be used to protect or treat a subject (e.g., a mammal such as a human) susceptible to, or suffering from a viral infection, by means of administering the vaccine by intranasal, peroral, oral, buccal, sublingual, intramuscular, intraperitoneal, intradermal, transdermal, subdermal, intravaginal, anal, intracranial, intravenous, transcutaneous, or subcutaneous administration. Methods of systemic administration of the vaccines and/or immunogenic compositions of the present disclosure may include conventional syringes and needles, or devices designed for ballistic delivery of solid vaccines (WO 99/27961), or needleless pressure liquid jet device (U.S. Pat. Nos. 4,596,556; 5,993,412), or transdermal patches (WO 97/48440; WO 98/28037). The Zika virus vaccines and/or immunogenic compositions of the present disclosure may also be applied to the skin (transdermal or transcutaneous delivery WO 98/20734; WO 98/28037). The Zika virus vaccines and/or immunogenic compositions of the present disclosure therefore may include a delivery device for systemic administration, pre-filled with the Zika virus vaccine or immunogenic compositions. Accordingly there is provided methods for treating or preventing Zika virus infection and/or for inducing an immune response in a subject (e.g., a mammal such as a human), including the step of administering a vaccine or immunogenic composition of the present disclosure and optionally including an adjuvant and/or a carrier, to the subject, where the vaccine or immunogenic composition is administered via the parenteral or systemic route.

The vaccines and/or immunogenic compositions of the present disclosure may be used to protect or treat a subject (e.g., a mammal such as a human) susceptible to, or suffering from a viral infection, by means of administering the vaccine or immunogenic composition via a mucosal route, such as the oral/alimentary or nasal route. Alternative mucosal routes are intravaginal and intra-rectal. The mucosal route of administration may be via the nasal route, termed intranasal vaccination. Methods of intranasal vaccination are well known in the art, including the administration of a droplet, spray, or dry powdered form of the vaccine into the nasopharynx of the individual to be immunized. Nebulized or aerosolized vaccine formulations are potential forms of the Zika virus vaccines and/or immunogenic compositions disclosed herein. Enteric formulations such as gastro resistant capsules and granules for oral administration, suppositories for rectal or vaginal administration are also formulations of the vaccines and/or immunogenic compositions of the present disclosure.

The Zika virus vaccines and/or immunogenic compositions of the present disclosure may also be administered via the oral route. In such cases the pharmaceutically acceptable excipient may also include alkaline buffers, or enteric capsules or microgranules. The Zika virus vaccines and/or immunogenic compositions of the present disclosure may also be administered by the vaginal route. In such cases, the pharmaceutically acceptable excipients may also include emulsifiers, polymers such as CARBOPOL®, and other known stabilizers of vaginal creams and suppositories. The Zika virus vaccines and/or immunogenic compositions may also be administered by the rectal route. In such cases the excipients may also include waxes and polymers known in the art for forming rectal suppositories.

In some embodiments, the administering step includes one or more administrations. Administration can be by a single dose schedule or a multiple dose (prime-boost) schedule. In a multiple dose schedule the various doses may be given by the same or different routes e.g. a parenteral prime and mucosal boost, a mucosal prime and parenteral boost, etc. Typically they will be given by the same route. Multiple doses will typically be administered at least 1 week apart (e.g. about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 16 weeks, etc.). Giving two doses separated by from 25-30 days (e.g. 28 days) is particularly useful.

The methods of the present disclosure include administration of a therapeutically effective amount or an immunogenic amount of the Zika virus vaccines and/or immunogenic compositions of the present disclosure. A therapeutically effective amount or an immunogenic amount may be an amount of the vaccines and/or immunogenic compositions of the present disclosure that will induce a protective immunological response in the uninfected, infected or unexposed subject to which it is administered. Such a response will generally result in the development in the subject of a secretory, cellular and/or antibody-mediated immune response to the vaccine. Usually, such a response includes, but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

In some embodiments, the protective immunological response induced in the subject after administration of a vaccine and/or immunogenic composition containing a non-human cell adapted Zika virus of the present disclosure is greater than the immunological response induced in a corresponding subject administered a vaccine and/or immunogenic composition containing a Zika virus that is not adapted for non-human cell growth and/or comprises a different non-human cell adaptation mutation. In some embodiments, the protective immunological response induced in the subject after administration of the vaccine and/or immunogenic composition containing a non-human cell adapted Zika virus of the present disclosure is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% greater than the immunological response induced in a corresponding subject administered a vaccine and/or immunogenic composition containing a Zika virus that is not adapted for non-human cell growth and/or comprises a different non-human cell adaptation mutation. Methods of measuring protective immunological responses are generally known to one of ordinary skill in the art.

In some embodiments, administration of a vaccine and/or immunogenic composition containing a non-human cell adapted Zika virus of the present disclosure induces generation of neutralizing antibodies to Zika virus in the subject. In some embodiments, administration of a vaccine and/or immunogenic composition containing a non-human cell adapted Zika virus of the present disclosure induces generation of neutralizing antibodies to Zika virus in the subject in an amount that is greater than the amount of neutralizing antibodies induced in a corresponding subject administered a vaccine and/or immunogenic composition containing a Zika virus that is not adapted for non-human cell growth and/or comprises a different non-human cell adaptation mutation. In some embodiments, administration of a vaccine and/or immunogenic composition containing a non-human cell adapted Zika virus of the present disclosure induces generation of neutralizing antibodies to Zika virus in the subject in an amount that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% greater than the than the amount of neutralizing antibodies induced in a corresponding subject administered a vaccine and/or immunogenic composition containing a Zika virus that is not adapted for non-human cell growth and/or comprises a different non-human cell adaptation mutation. In some embodiments, administration of a vaccine and/or immunogenic composition containing a non-human cell adapted Zika virus of the present disclosure induces generation of neutralizing antibodies to Zika virus in the subject in an amount that is at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 100-fold, or at least about 1000-fold greater than the than the amount of neutralizing antibodies induced in a corresponding subject administered a vaccine and/or immunogenic composition containing a Zika virus that is not adapted for non-human cell growth and/or comprises a different non-human cell adaptation mutation. Methods of measuring neutralizing antibodies in a subject are generally known to one of ordinary skill in the art.

Preferably, the therapeutically effective amount or immunogenic amount is sufficient to bring about treatment or prevention of disease symptoms. The exact amount necessary will vary depending on the subject being treated; the age and general condition of the subject to be treated; the capacity of the subject's immune system to synthesize antibodies; the degree of protection desired; the severity of the condition being treated; the particular Zika virus antigen selected and its mode of administration, among other factors. An appropriate therapeutically effective amount or immunogenic amount can be readily determined by one of skill in the art. A therapeutically effective amount or immunogenic amount will fall in a relatively broad range that can be determined through routine trials.

The present disclosure will be more fully understood by reference to the following Examples. They should not, however, be construed as limiting any aspect or scope of the present disclosure in any way.

EXAMPLES

Example 1: Clonal Zika Virus Strain Generation

This example describes the production of Zika virus (ZIKAV) strains with a known research history.

Materials and Methods Vero Cell Maintenance

One vial of WHO Vero 10-87 cells was rapidly thawed in a water bath and directly inoculated into 19 mL pre-warmed DMEM (Dulbecco's modified minimal essential medium) containing penicillin-streptomycin, L-glutamine 40 mM, and 10% FBS in a T-75 cm2 flask at 36° C.+/2° C., at 5% CO2. Cells were allowed to grow to confluency and sub-cultured using TrplE. This flask was expanded to two T-185 cm2 flasks, grown to confluency and subcultured to 31×T-185 cm2 flasks and grown until the cells reached 100% confluency. Cells were harvested by trypsinization, centrifuged at 800×g for 10 minutes, and resuspended in DMEM containing 10% FBS and 10% DMSO at a concentration of 1.9×107 cells/mL. One vial of the Vero cells was rapidly thawed and resuscitated as described above into a T-75 cm2 flask. These were subcultured twice to produce a cell bank in 13×T-185 cm2 flasks. After trypsinization, the cells were centrifuged at 800×g and resuspended in freezing media (DMEM containing 10% FBS, and 10% DMSO) at a concentration of 4.68×105 cells/mL. This cell bank was aliquoted into cryovials.

The Vero cells were grown and maintained in DMEM containing penicillin-streptomycin, L-glutamine and 10% FBS (cDMEM-10%-FBS). TrplExpress was used to maintain and trypsinize cells. Two days before viral adsorption, 6-well plates were seeded with 4-5×105 cells/well in 3 mL of cDMEM-10%-FBS or 7×105 cells in T-25 cm2 flasks in 5 mL cDMEM-10%-FBS, or 1×104 cells/well in 96-well plates in 0.1 mL cDMEM-10%-FBS. Incubators were monitored daily to maintain indicated temperatures. The Vero cell lines were stored in liquid nitrogen.

Plaque Assay

Viral titers were determined by plaque titration in freshly confluent monolayers of Vero cells grown in 6-well plates. Frozen aliquots were thawed and ten-fold dilution series of the aliquots were made in cDMEM-0%-FBS in 96-well plates. The diluted viruses were maintained on ice prior to inoculation of the Vero cell monolayers. At the time of assay, the growth medium was aspirated from the 6-well plate, and 100 µL of each virus dilution was added to the wells. Virus was adsorbed for 60 min at 36° C.±2° C., at 5% CO2, with frequent (every 10 min) rocking of the plates to prevent drying of the cell sheets. Following viral adsorption, 4 mL of a first agarose overlay (1× cDMEM-2%-FBS+0.8% agarose) maintained at 40-41° C. was added to each well. The agarose was allowed to solidify for 30 min at room temperature, and the plates were then incubated upside down for 4-6 days at 36° C.+/2° C., at 5% CO2. Two mL of a second agarose overlay containing 160 ng/mL of neutral red vital dye was added on day 4. Plaques were visualized on days 5 and 6.

Virus Quantification by TCID50 Assay

Viral titers were also determined by titration in freshly confluent monolayers of Vero cells grown in 96-well plates. Frozen aliquots were thawed and ten-fold dilution series of the aliquots were made in cDMEM-2%-FBS diluent in 96-well plates. The diluted viruses were maintained on ice prior to inoculation of the Vero cell monolayers. At the time of assay, the growth medium was aspirated from the 96-well plate, and 100 µL of each virus dilution was added to the wells. The plates were incubated for 5 days at 36° C.+/2° C., at 5% CO2. The 50% Tissue Culture Infective Dose (TCID50) titer was calculated using the Reed/Muench calculator.

Test Articles

Zika virus strain PRVABC59 (one 0.5 mL vial on dry ice) was received from the Centers for Disease Control and Prevention (CDC) Zika virus identification was confirmed through RT-PCR. The strain tested negative for Alphavirus and mycoplasma contamination by PCR. This information is summarized in Table 1.

TABLE 1

PRVABC59 strain information

| Strain | Isolation Information | Patient information | Prep info | Analyses | PFU |
|---|---|---|---|---|---|
| PRVABC59 (Asian) | Human serum; travel to Puerto Rico in 2015 | None provided | Passage: Vero(2)C6/36(1) Prep: 29, Jan. 2016 Host: C6/36 | Sequencing by ion torrent: gene accession #KU501215 PFU by plaque assay Identity by RT-PCR (—) For alphaviruses by PCR (—) for mycoplasma by ATCC and ABM PCR | 6.7 log pfu/mL |

Sequencing

A QIAampViral RNA Mini Spin kit was used to extract RNA from stabilized virus harvests of each isolate according to manufacturer protocols. Extracted RNA from each isolate was used to create and amplify 6 cDNA fragments encompassing the entire Zika viral genome. Amplified cDNA fragments were analyzed for size and purity on a 1% Agarose/TBE gel and subsequently gel purified using a Qiagen Quick Gel Extraction Kit. An ABI 3130XL Genetic Analyzer sequencer was used to conduct automatic sequencing reactions. Lasergene SeqMan software was used to analyze sequencing data.

Results

A ZIKAV strain with a known research history that was relevant to the current ZIKAV outbreak in the America's was sought. For this reason, ZIKAV strain PRVABC59 was chosen. To generate a well-characterized virus adapted for growth in Vero cells, the ZIKAV PRVABC59 was first amplified in Vero cells (P1).

Flasks of Vero cells (T-175 cm2), 100% confluent, were infected at an MOI of 0.01 in 4 mL of cDMEM-0%-FBS. Virus was adsorbed to the monolayer for 60 minutes at 36° C.±2° C., at 5% CO2, then 20 mL of cDMEM-0%-FBS was applied for viral amplification at 36° C.±2° C., at 5% CO2. The cell layer was monitored daily for cytopathic effect (CPE) following inoculation (FIG. 1). The supernatant was harvested after 96 hours by collecting the media and clarifying by centrifugation (600×g, 4° C., 10 min). The harvest was stabilized by adding trehalose to a final concentration of 18% w/v. The bulk was aliquoted into 0.5 mL cryovials and stored at −80° C.

Figure 2:
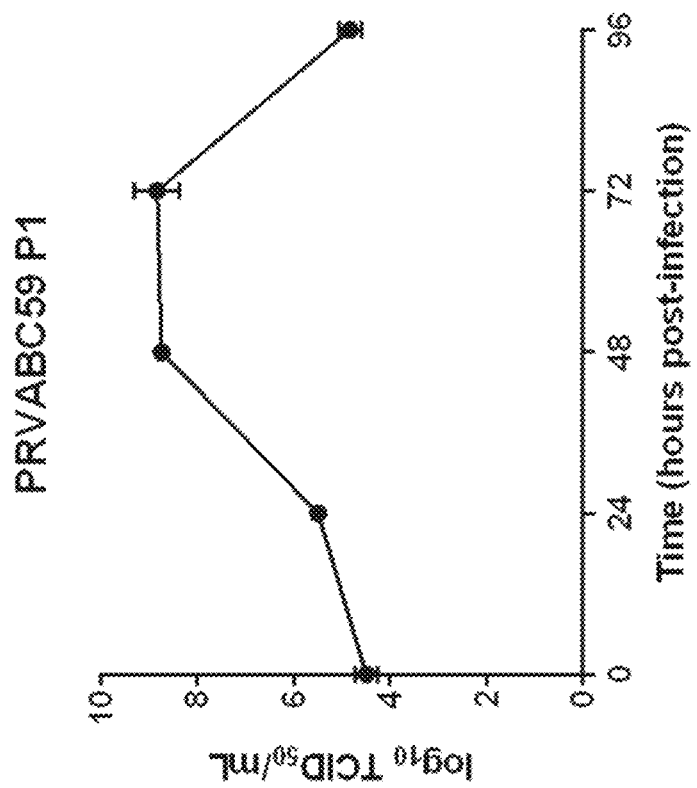
FIG. 2 shows growth kinetics of ZIKAV PRVABC59 P1 on Vero cell monolayers, as determined by $TCID_{50}$.

The stabilized P1 harvest was analyzed for the presence of infectious virus on Vero cell monolayers by a TCID50 assay. Growth kinetics were monitored by taking daily aliquots beginning on hour 0. Peak titer was reached by hour 72 (FIG. 2).

P1 material was plaque-purified by titrating the harvest from day 3 on 6-well monolayers of Vero cells. Plaques were visualized on day 6, and 10 plaques to be isolated were identified by drawing a circle around a distinct and separate plaque on the bottom of the plastic plate. Plaques were picked by extracting the plug of agarose using a sterile wide bore pipette while scraping the bottom of the well and rinsing with cDMEM-10%-FBS. The agarose plug was added to 0.5 mL of cDMEM-10%-FBS, vortexed, labeled as PRVABC59 P2a-j and placed in an incubator overnight at 36° C.±2° C., at 5% CO2.

Three plaques (PRVABC59 P2a-c) were carried forward for additional purification. Each isolate was plated neat in duplicate onto a fresh 6-well monolayer of Vero cells. This P2/P3 transition was plaque purified, and labeled PRVABC59 P3a-j.

Six plaques (PRVABC59 P3a-f) were carried forward for a final round of purification. Each isolate was plated neat in duplicate onto a fresh 6-well monolayer of Vero cells. This P3/P4 transition was plaque purified, and labeled PRVABC59 P4a-j.

Figure 3:
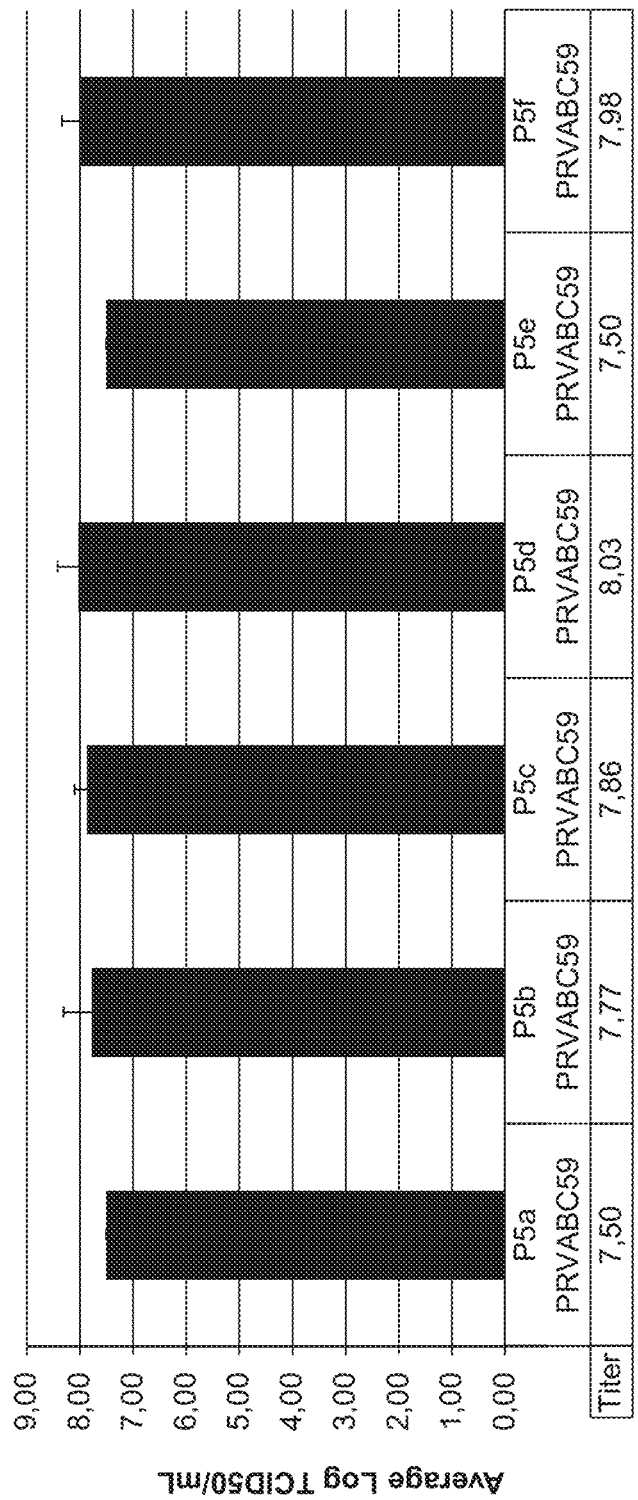
FIG. 3 shows potency assay testing ($TCID_{50}$) of Zika virus PRVABC59 P5 clones a-f.

Six plaques (PRVABC59 P4a-f) from the P4 plaque purification were blind passaged on monolayers of Vero cells in T-25 cm2 flasks. Each plaque pick was diluted in 2 mL cDMEM-0%-FBS 1 mL was adsorbed for 1 hour at 36° C.±2° C., at 5% CO2; the other 1 mL was stabilized with trehalose (18% v/v final) and stored at <−60° C. Following virus adsorption, cDMEM-0%-FBS was added to each flask and allowed to grow at 36° C.±2° C., at 5% CO2 for 4 days. Virus supernatants were harvested, clarified by centrifugation (600×g, 4C, 10 min), stabilized in 18% trehalose and aliquoted and stored at <−60° C. This P5 seed was tested by TCID50 for Zika virus potency (FIG. 3).

Figure 4:
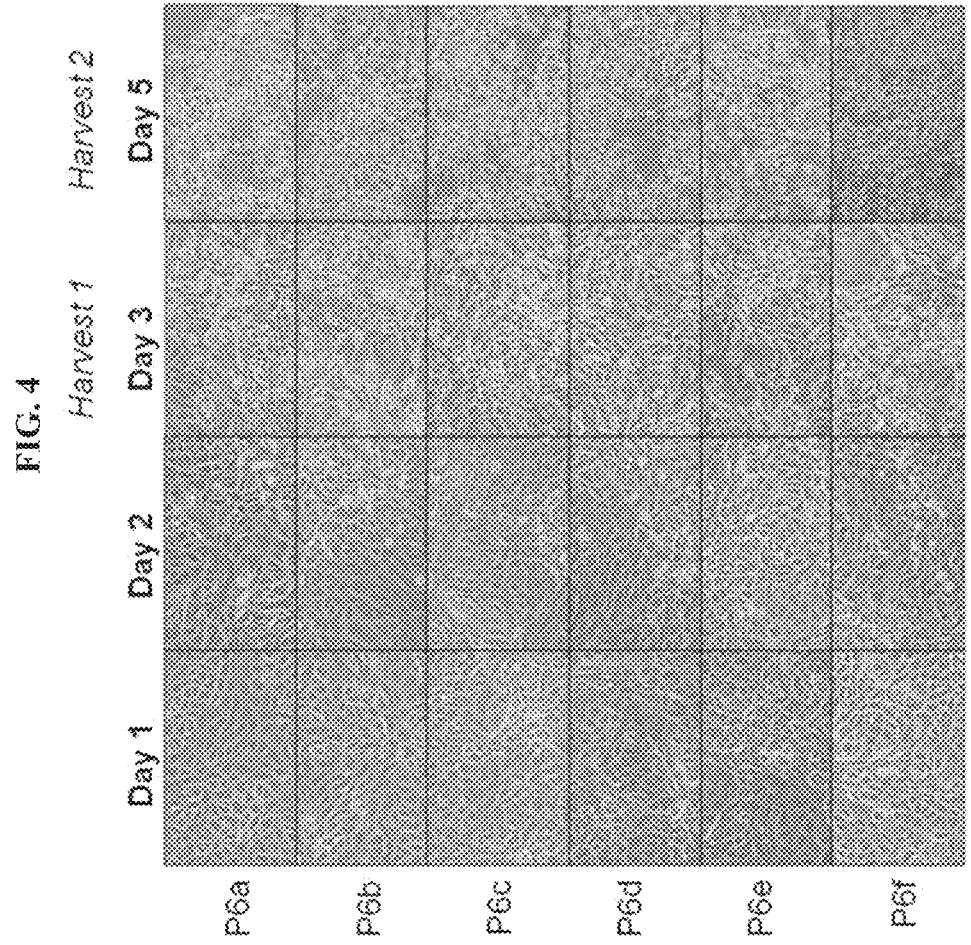
FIG. 4 shows bright-field microscopy images depicting the cytopathic effect (CPE) of growth of Zika virus PRVABC59 P6 clones a-f on Vero cell monolayers.

Confluent monolayers of T-175 cm2 flasks of Vero cells were infected with each of the six clones of PRVABC59 (P5a-f) at an MOI of 0.01 in 4 mL cDMEM-0%-FBS. The virus was allowed to adsorb for 60 minutes at 36° C.+/2° C., at 5% CO2, after which 20 mL of cDMEM-0%-FBS was added to each flask and allowed to grow at 36° C.+/2° C., at 5% CO2. Vero cell monolayer health and CPE was monitored daily. Virus was harvested on days 3 and 5 as indicated (FIG. 4). The P6 strain harvests from days 3 and 5 were pooled, stabilized with 18% trehalose, aliquoted and stored <−60° C.

Figure 5:
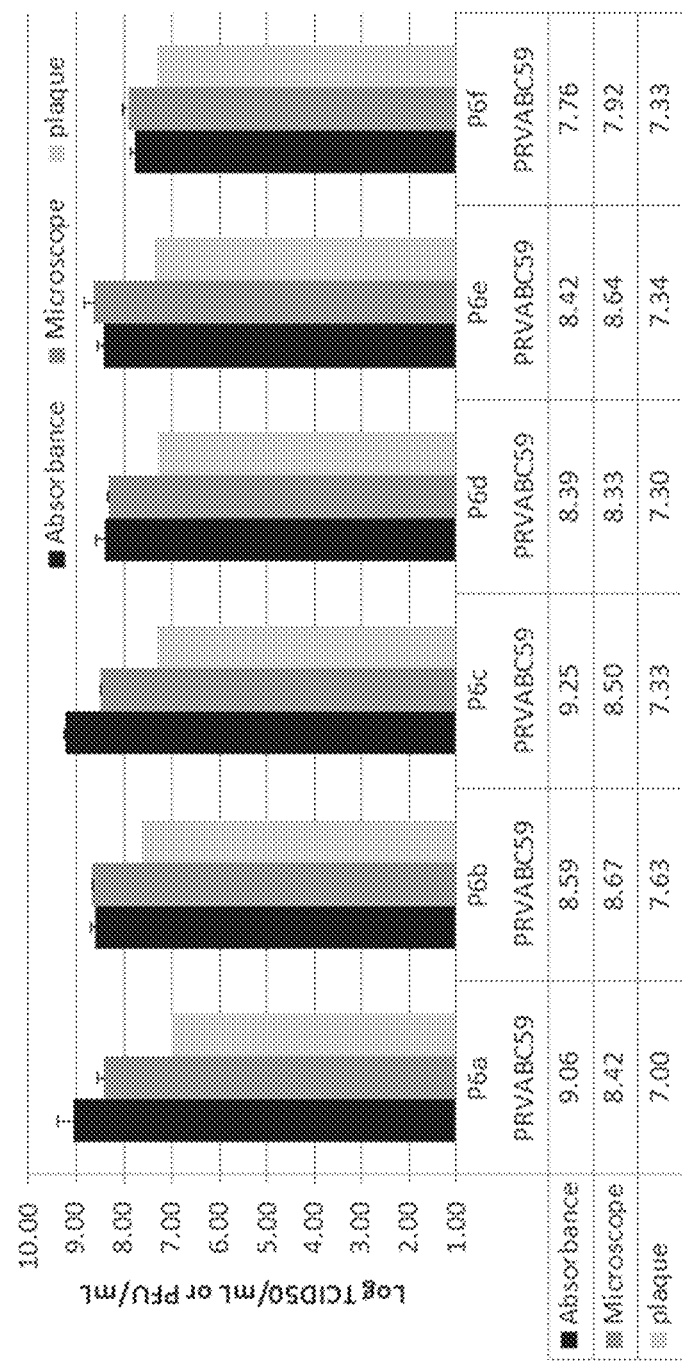
FIG. 5 shows potency assay testing ($TCID_{50}$) of Zika virus PRVABC59 P6 clones a-f

Each of the six clones of PRVABC59 (P6a-f) were tested for Zika virus in vitro potency (FIG. 5). The potency was determined by two different methods, TCID50 and plaque titration. The TCID50 was calculated by visual inspection of CPE (microscope) and by measuring the difference in absorbance (A560-A420) of the wells displaying CPE (yellow in color) compared with red (no CPE). The plates were read on a plate reader, and applied to the same calculator as the microscopically read-plates (absorbance). The values in TCID50 between the two scoring techniques are quite similar, while the values obtained by plaque titration are lower.

A summary of the generation of the P6 virus and characterization is shown in Table 2 below.

TABLE 2

Summary of virus passage and characterization for the generation of clonal ZIKAV strains

| Passage | Seed production/purification | Characterization |
|---|---|---|
| P1 | Virus amplification in Vero | TCID50 titer |
| P2 | Amplify P1 by plaque titration; Plaque purification of P1 | plaque purification |
| P3 | Pick and passage plaques from P2 plaque assay; plaque purification of P2 | plaque purification |
| P4 | Pick and passage plaques from P3 plaque assay; plaque purification of P3 | plaque purification |
| P5 | Amplify P4 plaques (a-f) in Vero cells | TCID50 titer |
| P6 | Amplify P5 (a-f) virus in Vero cells | TCID50 titer, plaque phenotype, genotype, full genome sequencing, growth kinetics |

An isolated Zika virus clone that closely resembled the envelope glycoprotein sequence of the original isolate was sought, since the envelope protein of flaviviruses is the dominant immunogenic portion of the virus. PRVABC59 clones P6a, P6c, P6d and P6f contained a G→T mutation at nucleotide 990 in the envelope region (G990T), resulting in an amino acid mutation of Val→Leu at envelope residue 330, whereas the envelope gene of PRVABC59 clones P6b and P6e were identical relative to the reference strain (GenBank ref KU501215.1) (Table 3 and FIG. 6).

TABLE 3

Sequencing of PRVABC59 P6 clones

| Strain | Nucleotide | Amino Acid | Mutation | Comments |
|---|---|---|---|---|
| Envelope sequencing (reference gene from PRVABC59; accession #KU501215) | | | | |
| PRVABC59 P6a | Env-990: G→T | Env-330: Val330→Leu | Val/Leu | Mutation in 3 of 4 reads. |
| PRVABC59 P6b | Env-1404: T→G silent | Wild type | Wild type | Wild type relative to reference. |
| PRVABC59 P6c | Env-990: G→T | Env-330: Val330→Leu | Val/Leu | Mutation in 3 of 4 reads. |
| PRVABC59 P6d | Env-990: G→T | Env-330: Val330→Leu | Val/Leu | Mutation in 2 of 2 reads. |
| PRVABC59 P6e | Wild type | Wild type | Wild type | Wild type relative to reference. |
| PRVABC59 P6f | Env-990: G→T | Env-330: Val330→Leu | Val/Leu | Mutation in 2 of 2 reads. 190 bp not sequenced (aa 421-484). |
| Full genome sequencing (reference gene from PRVABC59; accession #KU501215) | | | | |
| PRVABC59 P6b | Env-1404 T→G | Wild-type | Silent | Mutation in 2 of 2 reads |
|  | NS1-292 T→G | NS1-98 Trp98→Gly | Trp/Gly | Mutation in 2 of 2 reads |
| PRVABC59 P6e | NS1-292 T→G | NS1-98 Trp98→Gly | Trp/Gly | Mutation in 2 of 2 reads |

The two clones lacking mutations in the Zika envelope sequence were then subjected to full genome sequencing. Sequencing results are summarized in Table 3 above. Sequence analysis revealed a T→G substitution at nucleotide 292 in the NS1 region for both clones, resulting in a Trp→Gly mutation at NS1 residue 98. This mutation was also later confirmed through deep sequencing. The NS1 W98G mutation is located in the intertwined loop of the wing domain of ZIKAV NS1, which has been implicated in membrane association, interaction with envelope protein and potentially hexameric NS1 formation. While other tryptophan residues (W115, W118), are highly conserved across flaviviruses, W98 is not (FIG. 7). Interestingly, however, 100% conservation of the W98 residue is observed across 11 different ZIKAV strains, including those from the African and Asian lineages. The identified mutations in each strain are summarized in Table 4.

TABLE 4

Summary of mutations identified in PRVABC59 P6 clones

| Clone | Nucleotide | Amino Acid |
|---|---|---|
| Mutations identified in envelope | | |
| P6a | G990T | V330L |
| P6b | T1404G | (silent) |
| P6c | G990T | V330L |
| P6d | G990T | V330L |
| P6e | none | none |
| P6f | G990T | V330L |
| Additional mutations identified in genome | | |
| P6b | NS1-T292G | NS1-W98G |
| P6e | NS1-T292G | NS1-W98G |

Ref sequence: KU501215.1 (PRVABC59)

Figure 8:
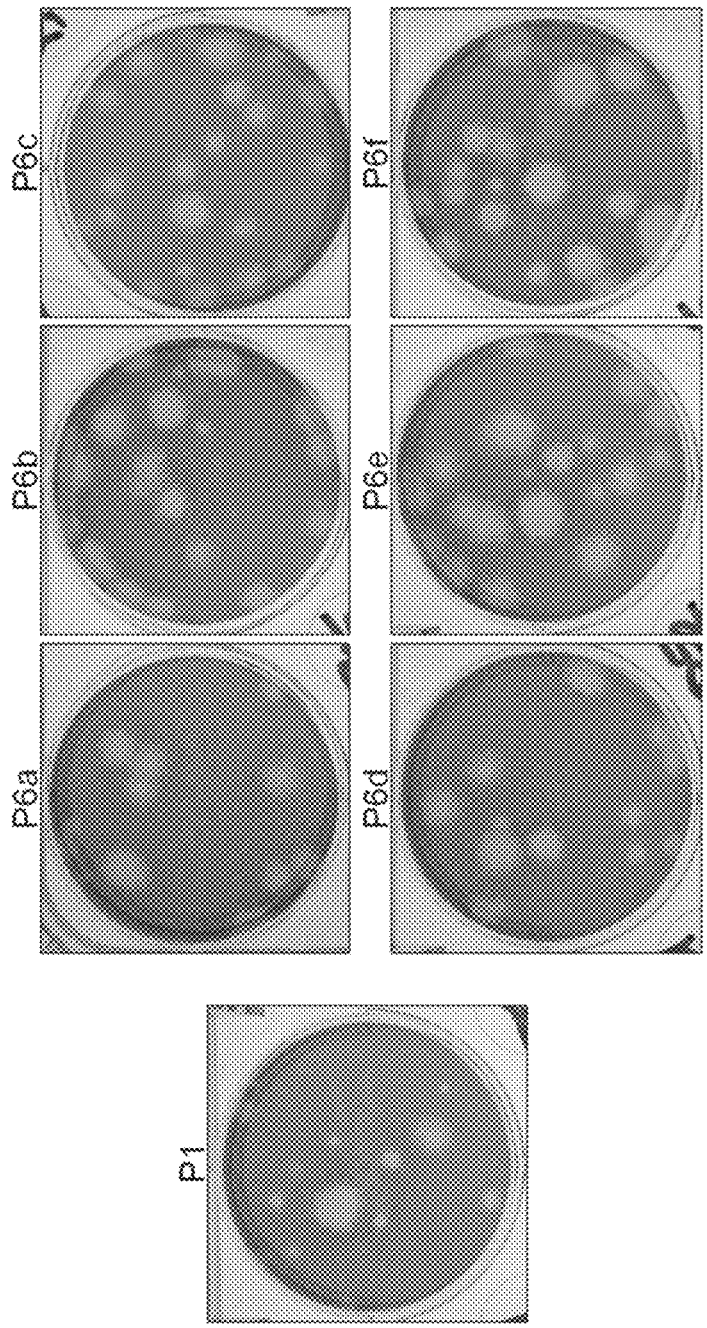
FIG. 8 shows the plaque phenotype of ZIKAV PRVABC59 P6 virus clones a-f compared to ZIKAV PRVABC59 P1 virus.
Figure 9:
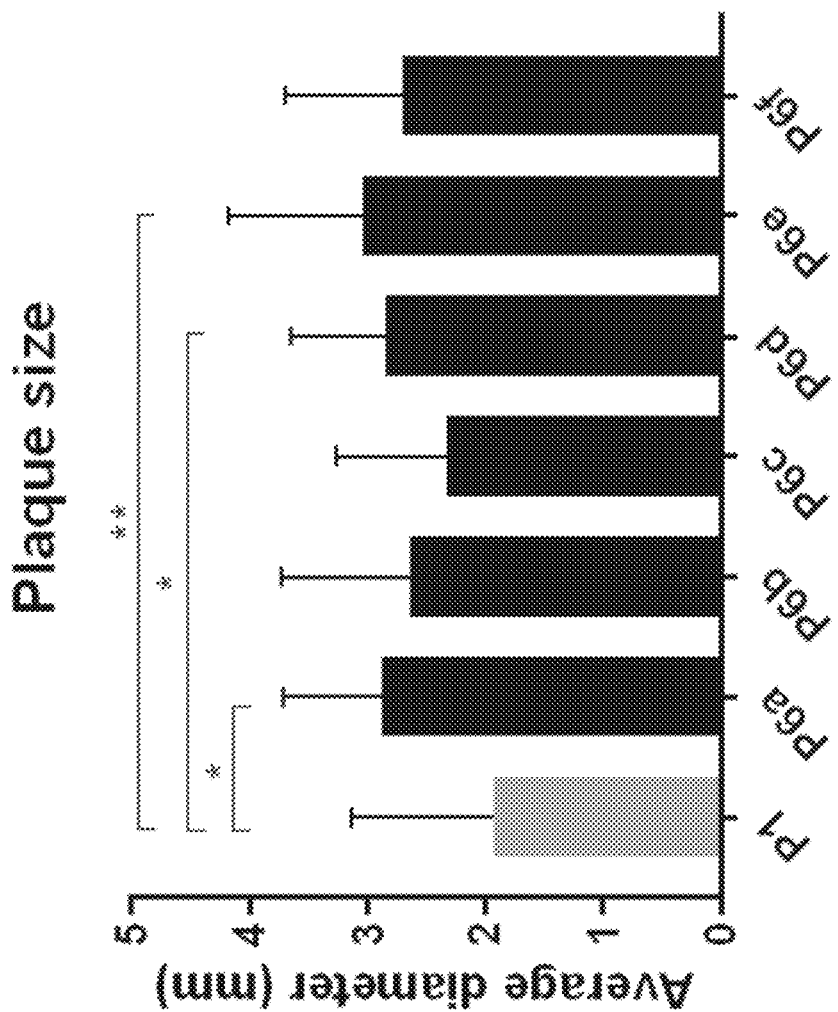
FIG. 9 shows the mean plaque size of ZIKAV PRVABC59 P6 virus clones compared to ZIKAV PRVABC59 P1 virus.

Phenotypic analysis of the ZIKAV PRVABC59 P6 stocks was conducted to characterize the ZIKAV clones. As illustrated in FIG. 8 and quantified in FIG. 9, each clonal isolate consisted of a relatively homogeneous population of large-sized plaques as compared to the P1 virus which had a mixed population of large and small plaques. These data suggest the successful isolation of single ZIKAV clones.

Figure 10:
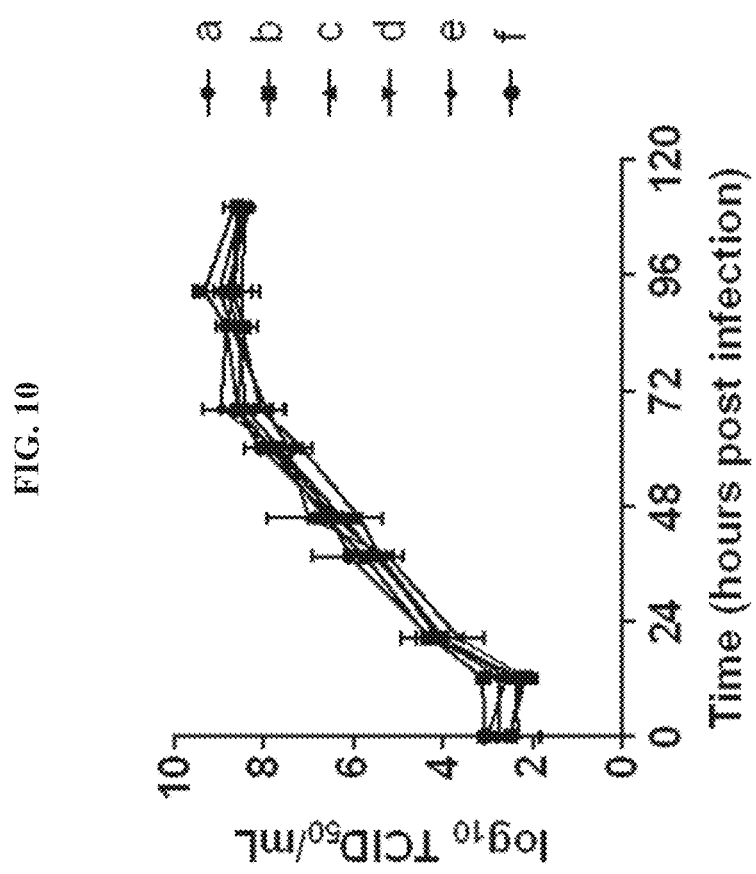
FIG. 10 shows the growth kinetics of ZIKAV PRVABC59 P6 clones a-f in Vero cells under serum-free growth conditions.

Next, growth kinetics analyses in Vero cells of the ZIKAV PRVABC59 P6 clones were analyzed. Vero cells were infected with 0.01 TCID50/cell of each ZIKAV P6 clones in serum free growth medium. Viral supernatant samples were taken daily and simultaneously assayed for infectious titer by TCID50 assay. For all P6 clones, peak titer occurred between day 3 and 4 (~9.0 log 10 TCID50/mL). There was no significant difference in growth kinetics of the various P6 clones (FIG. 10).

Taken together, the results indicate that a Zika virus seed was successfully generated. This seed selection required understanding of growth history, kinetics, yield, genotype, and phenotype of the virus. Importantly, clonal isolation of the Zika virus strains allowed for the successful purification of the virus away from contaminating agents (e.g., adventitious agents that may be in the parental human isolate). Interestingly, three sequential plaque purifications succeeded in quickly selecting Vero-cell adapted virus (strains P6a-f), where these strains were able to replicate well in serum-free Vero cell cultures, with strain P6a, c, d, and f harboring a mutation in the viral envelope protein, while strains p6b and p6e obtained a mutation in the viral NS1 protein (with no modification to the viral envelope). Additionally, the Vero-adapted strains enabled efficient and reproducible growth and manufacture of subsequent viral passages propagated from these strains. Without wishing to be bound by theory, the Env-V330L mutation observed in strains P6a, c, d, and f may potentially be a result of in vitro adaptation, as a mutation at Env 330 was also observed upon passaging in Vero cells (Weger-Lucarelli et al. 2017. Journal of Virology). Because the envelope protein is the dominant immunogenic epitope of Zika virus, strains containing a Vero adaptive mutation in Env may negatively impact vaccine immunogenicity. Without wishing to be bound by theory, the adaptation mutation in protein NS1 appears not only to enhance viral replication, but may also reduce or otherwise inhibit the occurrence of undesirable mutations, such as in the envelope protein E (Env) of the Zika virus. In addition, NS1 may be known to bind to the Envelope protein during the life cycle of the virus. This mutation (NS1 W98G) may be implicated in changing the ability of the NS1 to associate, and possibly co-purify, with the virus during downstream processing. NS1 is also known to be immunogenic, and could be implicated in the immune response to the vaccine.

Example 2: Preclinical Immunogenicity and Efficacy of a Purified Inactivated Zika Virus Vaccine (PIZV) Derived from the P6b and P6e Strains The following example describes the preclinical immunogenicity and efficacy in CD1 and AG129 mice of an inactivated Zika virus vaccine (PIZV) derived from the P6b and P6e strains. As described in Example 1, six clones were generated from the epidemically relevant PRVABC59 strain, and two (P6b and P6e) were chosen for further preclinical immunogenicity and efficacy studies.

Materials and Methods

Purification, Inactivation and Formulation of a Zika Virus Vaccine

A lot of inactivated ZIKAV vaccine, suitable for use in preclinical immunogenicity and efficacy studies, was generated and characterized. Virus was amplified from the P6b and P6e strains by infecting flasks of confluent Vero cells at a MOI of 0.01. Virus was adsorbed for 1 hour at 36° C.±2° C./5% $CO_2$. Following adsorption, 20 mL of cDMEM-0%-FBS was added to each flask, and incubated at 36° C.±2° C./5% $CO_2$ for five days. Cell supernatants were harvested on day 3 and 5 post-infection, and cell debris was clarified by centrifugation.

For each isolate, clarified supernatants were pooled, stabilized in DMEM containing 18% trehalose and stored at <−60° C. Pooled, clarified virus supernatants were thawed in a 37° C. water bath and treated with benzonase overnight at 4° C. Following benzonase treatment, each sample was applied to a Sartorius PP3 depth filter. Following depth filtration, each sample was applied to a Centricon Plus-70 tangential flow filtration (TFF) device. Retentate was buffer exchanged, diluted, and applied to a Sartorius SartobindQ IEXNano. Each sample was applied to a second Sartorius SartobindQ IEXNano and eluted using a 3 step-elution process with 250 mM, 500 mM, and 750 mM NaCl. Following MonoQ chromatography and dilution, each 250 mM eluate was applied to a Centricon Plus-70 cross flow filtration (CFF) device for buffer exchange, diluted to 35 mL with PBS, and stored at 2-8° C.

For formalin inactivation, freshly prepared 1% formaldehyde was added dropwise to each purified sample with gentle swirling to obtain a final formaldehyde concentration of 0.02%. Samples were incubated at room temperature (~22° C.) for 14 days with daily inversion. Formaldehyde was neutralized with sodium metabisulfite for 15' at room temperature before being applied to a Centricon Plus-70 tangential flow filtration (TFF) device. Buffer exchange was performed four times by the addition of 50 mL Drug Substance Buffer (10 mM $NaH_2PO_4$, 50 mM NaCl, 6% sucrose, pH 7.4). Each sample was then diluted to 15 mL with Drug Substance Buffer, sterilized using a 0.2m syringe filter, aliquoted into sterile stoppered glass vials (0.5 mL per vial) and frozen at <−60° C.

Figure 11:
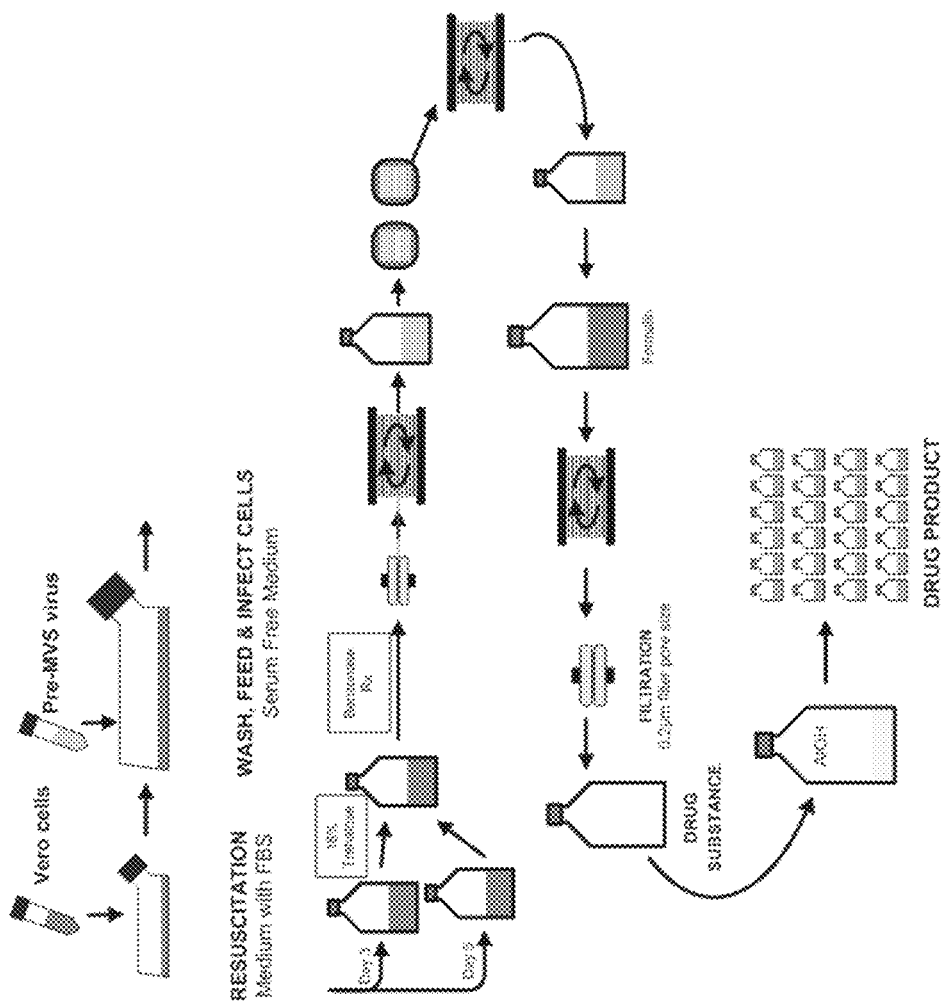
FIG. 11 shows a schematic of the steps taken to prepare PRVABC59 P6b and P6e formulated drug product for the immunization experiments.

Virus inactivation was confirmed by TCID50 assay and double infectivity assay. Briefly drug substance sample was applied to C6/36 cells and allowed to amplify for 6 days. Supernatant from C6/36 cells was applied to Vero cells and CPE was monitored for 8 days. For drug product formulation, vials of PIZV drug substance were thawed, pooled according to sample type, and diluted to 1 ng/mL or 10 ng/mL in PBS with or without Alhydrogel (Brenntag; 0.5 mg/mL final, 0.050 mg/dose) and incubated overnight at 2-8° C. with gentle agitation. The resulting drug product lots were then aliquoted into sterile stoppered glass vials and stored at 2-8° C. until use. FIG. 11 provides a summary of the steps used to prepare drug product.

Mouse Immunization and Challenge

For the immunogenicity study, six-week old male and female Swiss-ICR (CD-1) mice were divided into 6 groups (n=10/group). On Day 0, mice in groups 1-5 were inoculated with 0.1 mL of vaccine by the intramuscular (i.m.) route (2×0.05 mL injections). Mice in group 6 were inoculated with PBS as a placebo control. Mice were boosted on day 28 and 56 using the same dosage and vaccine type as day 0. Blood samples were collected on day −1 (pre-immune), day 27 (prime), day 42 (boost 1) and day 70 (boost 2).

For the immunogenicity and efficacy study, four-week old male and female AG129 mice were divided into 7 groups (n=5/group). On Day 0, mice in groups 1-6 were inoculated with 0.1 mL of vaccine by the intramuscular (i.m.) route (2×0.05 mL injections). Mice in group 7 were inoculated with PBS as a placebo control. Mice were boosted on day 28 using the same dosage and vaccine type as on day 0. Blood samples were collected from the tail vein on day −1 (pre-immune), day 27 (prime) and day 55 (boost). At the time of euthanization, mice were bled via cardiac puncture under deep anesthesia with isofluorane (terminal). On day 56, mice were intraperitoneally challenged with 104 plaque forming units (PFU) of ZIKAV PRVABC59.

Serum Transfer

Serum was collected from PIZV-vaccinated and challenged AG129 mice, and were frozen after pooling (groups 1, 2, 4, and 5 of Table 6). The serum pool was thawed, and the test articles were generated by three-fold dilutions of the serum pool in PBS. A placebo was generated using 3-fold dilutions of AG129 normal mouse serum in PBS.

The test articles were administered as 0.1 mL intraperitoneal injections into AG129 mice (an equivalent volume of the placebo article was administered to control mice). Animals were then challenged intraperitoneally with 104 plaque forming units of Zika virus strain PRVABC59 in 100 µL.

Allowable blood volume by weight was collected as whole blood by tail bleeding from ten mice on day −11 (pre-immunization). Whole blood was collected from each mouse on day 1 (primary, circulating Nab) and day 4 (viremia) by tail bleeding. Terminal bleeding after lethal challenge was performed by heart puncture under deep anesthesia for larger volume before euthanization by cervical dislocation. Blood samples were collected in microtainer SST serum separation gel tubes and allowed to clot for at least 30 min before separation of serum by centrifugation (10,000×g for 2 min) and frozen at −80° C.

Plaque Reduction Neutralization Test

Neutralizing antibody titers were determined by a plaque reduction neutralization test (PRNT) as described previously (See e.g., Osorio et al. Lancet Infect Dis. 2014 September; 14(9):830-8).

Reporter Virus Particle (RVP) Neutralization Assay

Neutralizing antibody titers were analyzed by titration of serum samples with a constant amount of Zika RVPs in Vero cells grown in 96-well plates. RVPs contained the prME proteins of Zika (strain SPH2012) and a Dengue-based Renilla luciferase reporter. Briefly, sera were heat inactivated at 56° C. for 30 min, diluted, and then incubated at 37° C. with RVPs. The serum/RVP mixture was then mixed with Vero cells and incubated for 72 hours at 37° C.±2° C./5% CO2 before detection with luciferase substrate. Data was analyzed using JMP11 non-linear 4 parameter analysis, normalized to a positive tracking control and effective dose 50% (EC50) was reported.

Unless indicated to the contrary, all additional experimental methods were carried out as described in Example 1 above.

Results

To assess the immunogenicity of the PIZV candidates in 6 week old male and female CD-1 mice, groups of CD-1 mice (N=10/group) were immunized by the i.m. route with either a 0.1 µg (+ alum), 1.0 µg (+ alum) dose of a vaccine derived from either ZIKAV PRVABC69 P6b or P6e virus strains. To assess the need for adjuvant, a group of animals was vaccinated with 0.1 µg of vaccine derived from P6e and lacking alum adjuvant. Vaccinations occurred on days 0, 28, and 56, with group 6 receiving PBS as a placebo control (FIG. 12A and Table 5).

TABLE 5

PIZV formulations and challenges in CD-1 mice

| Group | Strain | Dose (µg) | Alum (µg) | N |
|---|---|---|---|---|
| 1 | P6b | 0.1 | 0.50 | 10 |
| 2 | P6b | 1.0 | 0.50 | 10 |
| 3 | P6e | 0.1 | 0.50 | 10 |
| 4 | P6e | 1.0 | 0.50 | 10 |
| 5 | P6e | 0.1 | — | 10 |
| 6 | Placebo (PBS) | — | — | 10 |

Following vaccination, serum samples collected after primary (day 27), secondary (day 40) and tertiary (day 70) immunizations were tested for ZIKAV-specific neutralizing antibodies by RVP neutralization assay (FIG. 12B). Twenty-seven days after receiving the first dose, a slight neutralizing antibody response was observed in mice vaccinated with PIZV derived from either clone containing alum, as compared to the PBS placebo control group. Importantly, this response increased significantly upon a second immunization (day 40), but was not additionally enhanced upon immunization with a third dose (day 70). No neutralizing antibody response was observed in mice vaccinated with non-adjuvanted vaccine (FIG. 12B).

To assess the immunogenicity and protective efficacy of the PIZV candidates, groups of 4 week old AG129 mice (n=5/group) were immunized by the i.m. route with either a 0.1 ng dose (+ alum), 1.0 ng dose (+ alum) or 0.1 ng dose (– alum) of a vaccine derived from either the ZIKAV PRVABC59 P6b or P6e stocks on days 1 and 28 (FIG. 13A and Table 6).

TABLE 6

PIZV formulations and challenges in AG129 mice

| Group | Sex | Strain | Dose (µg) | Alum (µg) | N |
|---|---|---|---|---|---|
| 1 | F | P6b | 0.1 | 0.50 | 5 |
| 2 | F | P6b | 1.0 | 0.50 | 5 |
| 3 | F | P6b | 0.1 | — | 5 |
| 4 | M | P6e | 0.1 | 0.50 | 5 |

TABLE 6-continued

PIZV formulations and challenges in AG129 mice

| Group | Sex | Strain | Dose (µg) | Alum (µg) | N |
|---|---|---|---|---|---|
| 5 | M | P6e | 1.0 | 0.50 | 5 |
| 6 | M | P6e | 0.1 | — | 5 |
| 7 | M | Placebo (PBS) | — | — | 5 |

Following vaccination, vaccinated and control mice were intraperitoneally challenged at day 56 with 104 PFU of ZIKAV PRVABC59 (low passage). Serum samples collected after primary (D27) and secondary (D55) immunizations were tested for ZIKAV-specific neutralizing antibody response (FIG. 13B and Table 7). Only groups receiving the high dose of alum-adjuvanted vaccine (groups 2 and 5) elicited a neutralizing antibody response after a single immunization, which increased dramatically after boosting. In contrast, groups receiving either the low or high dose of alum-adjuvanted vaccine produced a high neutralizing antibody response after a second dose. Upon receiving two doses of vaccine, there was no statistical difference between groups of mice receiving alum-adjuvanted vaccine, regardless of the dosage or the derivation from the P6 clone.

TABLE 7

ZIKAV-specific neutralizing antibody response

| | | Serum neutralizing antibody titers | | | |
|---|---|---|---|---|---|
| | | D27 (prime) | | D55 (boost) | |
| Group | Formulation | GMT | % sc | GMT | % sc |
| 1 | P6b 0.1 µg + alum | <20 | 40 | 1280 | 100 |
| 2 | P6b 1.0 µg + alum | 135 | 80 | 2229 | 100 |
| 3 | P6b 0.1 µg – alum | <20 | 0 | <20 | 0 |
| 4 | P6e 0.1 µg + alum | <20 | 20 | 640 | 100 |
| 5 | P6e 1.0 µg + alum | 30 | 100 | 905 | 100 |
| 6 | P6e 0.1 µg – alum | <20 | 0 | <20 | 20 |
| 7 | PBS | <20 | 0 | <20 | 0 |

Figure 14:
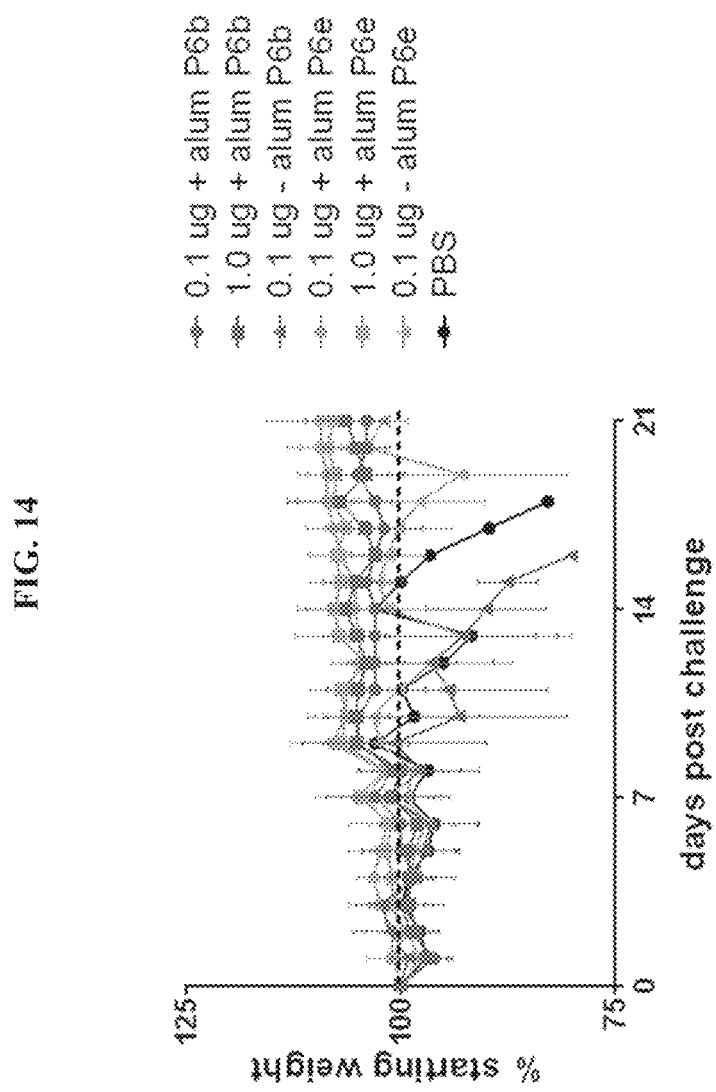
FIG. 14 shows the mean weight of AG129 test groups post-challenge, represented as a percentage of starting weight. Error bars represent standard deviation.
Figure 15:
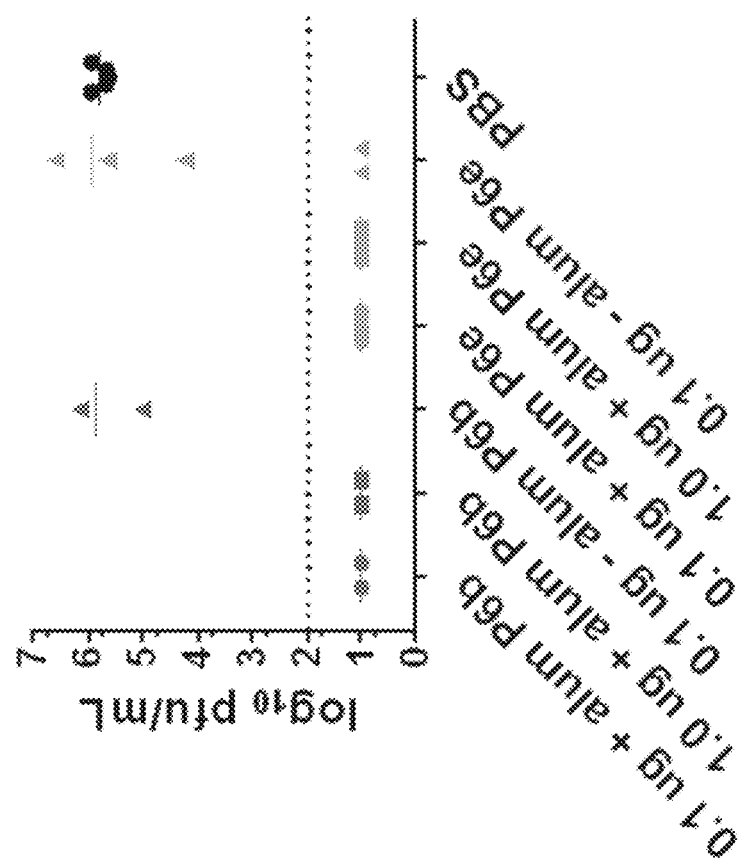
FIG. 15 shows the serum viremia of individual AG129 mice two days post-challenge, reported as PFU/mL. Solid lines represent the mean of a group. The limit of detection (2.0 $\log_{10}$) is represented by a dashed line.
Figure 16:
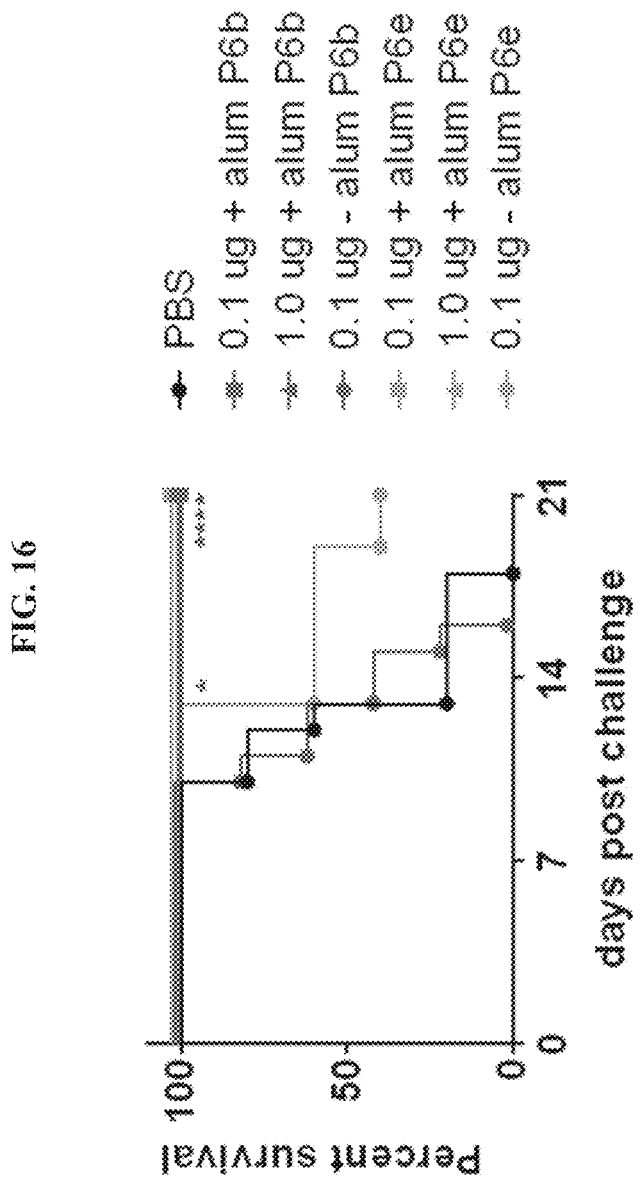
FIG. 16 shows the survival analysis of AG129 test groups post-challenge.

All groups were also monitored for mortality, morbidity and weight loss for 21 days post challenge. Viremia following challenge was detected and quantitated by plaque titration. Mice vaccinated with a low or high dose of PIZV candidates formulated with alum (groups 1, 2, 4 and 5) were fully protected from lethal ZIKAV challenge, as assessed by the plaque reduction neutralization test (PRNT) assay, as well as a comparable secondary neutralization assay (Table 8). No weight loss or clinical signs of illness were observed in vaccinated mice, none had detectable infectious viremia three days post challenge, and all mice vaccinated with either low or high dose antigen+ alum adjuvant survived to 21 days post-challenge (FIGS. 14-16). In contrast, challenge of all nave mice resulted in high viremia on day 2 post challenge and morbidity/mortality between day 10 and 18 post challenge (median survival=D13). Additionally, challenge of mice vaccinated with a non-alum-adjuvanted low dose vaccine derived from strain P6b resulted in high viremia on day 2 post challenge and a median survival day similar to the placebo control group, while mice vaccinated with a non-alum-adjuvanted low dose derived from clone e remained partially protected with a median survival of 19 days. These results indicate immunization is more effective with alum, secondary immunization may be a requirement, and that low dose was as effective as high dose.

TABLE 8

Serum neutralizing antibody titers

| Pool | Serum neutralizing antibody titers Terminal (post challenge) | |
| --- | --- | --- |
| | PRNT$_{50}$ | Secondary assay |
| Alum (1, 2, 4, 5) | 10240 | 20480 |
| No alum (3, 6) | 2560 | 2560 |
| PBS (7) | 1280 | 1280 |

Additionally, the presence of NS1 in the vaccine drug substance (DS) produced from whole inactivated P7b and P7e virus (one additional passage from the P6b and P6e strains, respectively) was tested. A sandwich ELISA was performed using plates pre-coated with a monoclonal antibody reactive to both Asian and African lineages of Zika virus NS1, but non-cross-reactive to Dengue NS1. Duplicate 2-, 4-, 8-, 16-, and 32-fold dilutions of DS were prepared, and were compared to a standard curve using recombinant purified NS1 in duplicate at a concentration of 0-8 ng/mL. Duplicate dilutions of DS buffer alone were prepared as negative controls. Bound NS1 was detected with anti-NS1 HRP-conjugate, and absorbance (A450-A630) of the wells with DS buffer alone was subtracted from the absorbance measured in the wells containing the matching DS samples. Results of the sandwich ELISA are shown in Table 9 below. Interestingly, NS1 was observed to co-purify with the vaccine drug substance preparations, suggesting that viral NS1 may be an immunogenic component of the whole inactivated virus vaccine.

TABLE 9

NS1 ELISA

| Strain in vaccine preparation | Sample OD | Predicted log ng/mL | Std Error | Lower 95% | Upper 95% | Dilution Factor | Predicted concentration (ng/mL) |
| --- | --- | --- | --- | --- | --- | --- | --- |
| P7b | 3.61 | 0.951 | 0.018 | 0.915 | 0.986 | 32 | -285 |
| P7e | 3.79 | 0.980 | 0.023 | 0.935 | 1.024 | 32 | -306 |

The threshold of neutralizing antibody (Nab) needed to confer protection from wild-type Zika virus challenge after passive transfer of antibodies was next tested. (Tables 10A and B).

TABLE 10A design of passive transfer study in AG129 mice

| Group | Test Article | Serum dilution | Predicted Nab titer before IP |
| --- | --- | --- | --- |
| 1 | 100 μL | 1/3 | 6827/3.83 |
| 2 | 100 μL | 1/9 | 2276/3.36 |
| 3 | 100 μL | 1/27 | 759/2.88 |
| 4 | 100 μL | 1/81 | 253/2.40 |
| 5 | 100 μL | 1/243 | 84/1.93 |
| 6 | 100 μL | 1/729 | 28/1.45 |
| 7 | 100 μL | 1/2187 | 9/0.97 |
| 8 | 100 μL | PBS | — |

TABLE 10B

Timing of passive transfer study in AG129 mice

| Description | Study Day |
| --- | --- |
| Passive transfer | Day 0 |
| Primary Bleed (AM) | Day 1 |
| Challenge (PM) | Day 1 |
| Viremia Bleed | Day 4 |
| Terminal Bleed | Day 29 for survivors |

Figure 17:
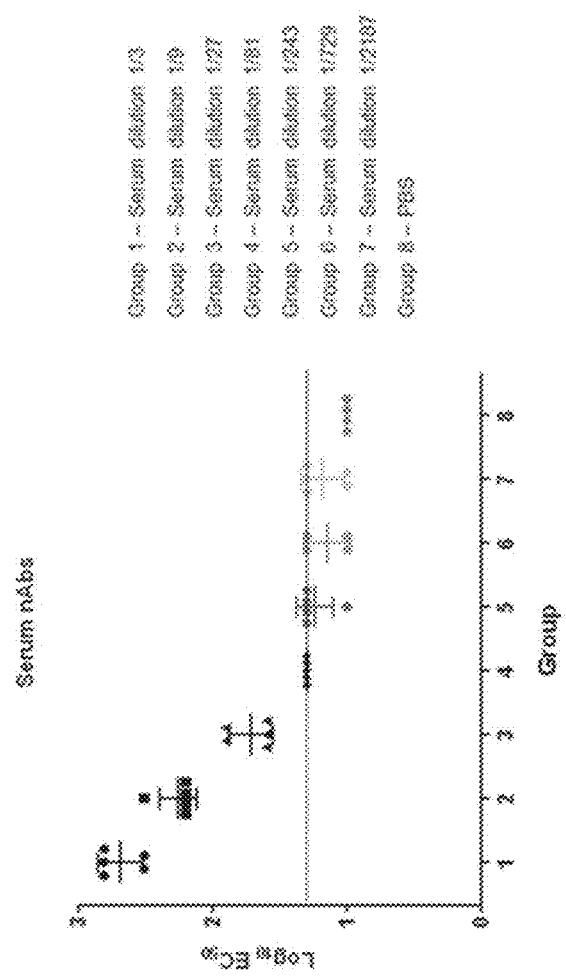
FIG. 17 shows the pre-challenge serum circulating ZIKAV neutralizing antibody (Nab) titers following passive transfer of pooled sera from vaccinated and challenged AG129 mice.

Pooled serum from vaccinated and challenged AG129 mice was serially diluted 3-fold in PBS and intraperitoneally injected into 7 groups (N=5/group) of 5-6 week old AG129 mice. Pre-immune AG129 mouse serum was used as placebo control (group 8). Following passive transfer (1 6-19 hours later), whole blood was collected and serum was separated by centrifugation from each mouse prior to virus challenge for determination of circulating neutralizing antibody titer (FIG. 17). Just prior to virus challenge, groups of mice (designated groups 1, 2, 3, 4, 5, 6, 7, 8) had mean log 10 neutralizing antibody titers of 2.69, 2.26, 1.72, 1.30, <1.30, <1.30, <1.30, <1.30, respectively.

Twenty four hours following passive transfer of ZIKV nAbs, mice were intraperitoneally challenged with 104 pfu of ZIKV PRVABC59. Following challenge, animals were weighed daily and monitored 1-3 times a day for 28 days for signs of illness. A clinical score was given to each animal based on the symptoms (Table 11). Animals that were moribund and/or showed clear neurological signs (clinical score ≥2) were humanely euthanized and counted as non-survivors.

TABLE 11

Description of clinical scores given while monitoring for morbidity and mortality

| Score | Description |
| --- | --- |
| 0 | Normal appearance and behavior |
| 1 | Slightly ruffled fur and/or general loss of condition |
| 2 | Increases in above behavior/appearance, breathing changes, twitching, anti-social behavior |
| 3 | First signs of neuropathy - Severely hunched posture, partial paralysis (immobility, unsteady gait, flaccid hind legs, severe twitching), or full paralysis |
| 4 | Found dead without showing signs of score of 2 or 3 first |

Figure 18:
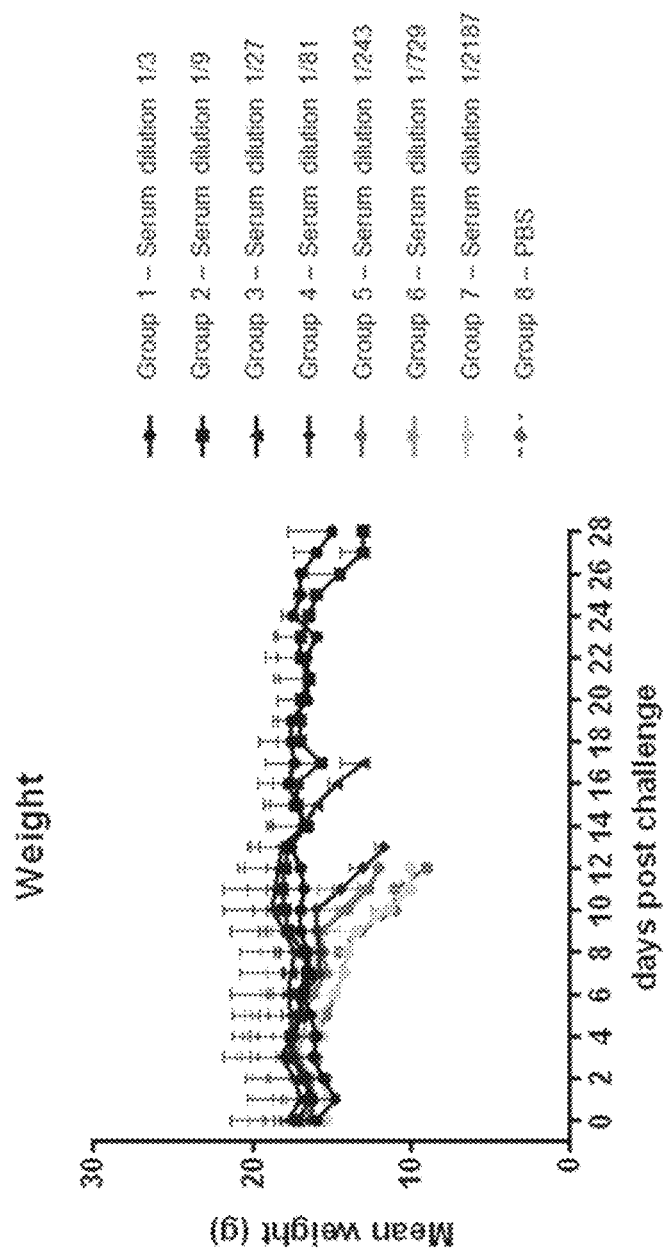
FIG. 18 shows the mean body weight of passive transfer and control mice challenged with Zika virus.
Figure 19:
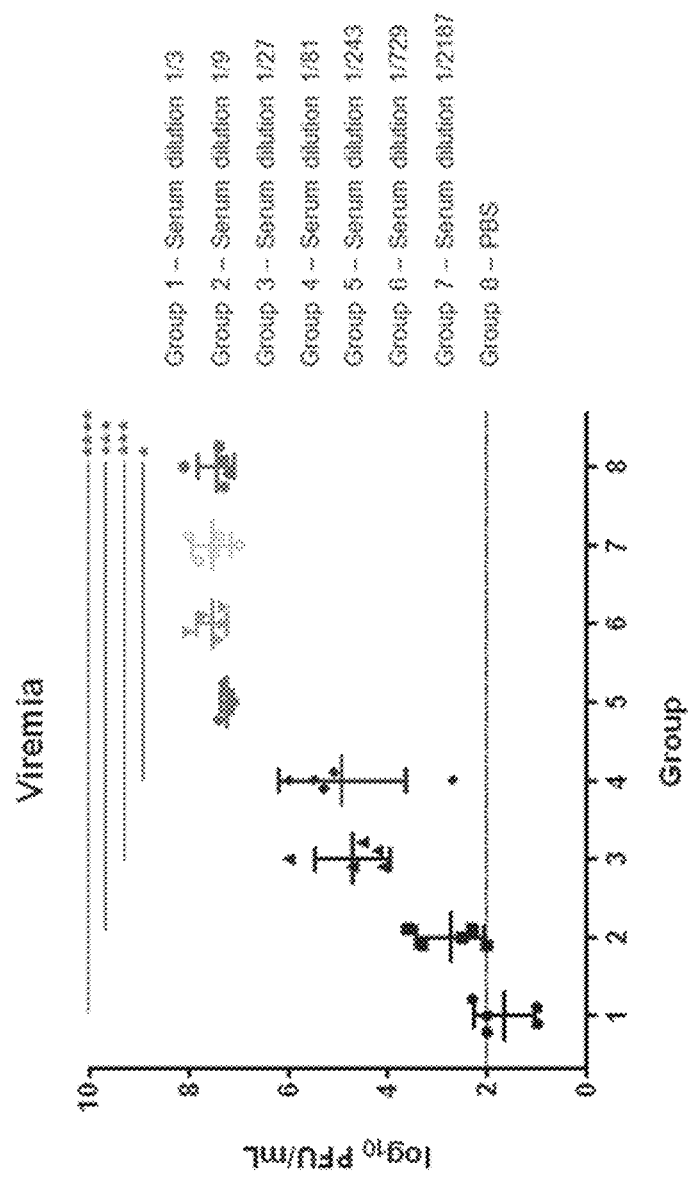
FIG. 19 shows the serum viremia of individual AG129 mice three days post-challenge, reported as PFU/mL.

Signs of disease began appearing nine days after challenge in the control group (group 8) and groups 5-7, with a corresponding loss in weight (FIG. 18). Whole blood was collected and serum was separated by centrifugation from each animal three days post challenge. Serum samples were analyzed for the presence of infectious ZIKV using a plaque titration assay (FIG. 19). The mean infectious titer (log 10 pfu/mL) for mice in groups 1-8 were: 1.66, 2.74, 4.70, 4.92, 7.24, 7.54, 7.54 and 7.46, respectively. Importantly, mice in groups 1-4 with detectable levels of ZIKV neutralizing antibodies (>1.30 log 10) had statistically significant lower levels (102.5- to 106.0-fold lower titers) of viremia (p=0.0001, 0.0003, 0.0007 and 0.0374) than control mice. These results suggested that detectable levels of ZIKV neutralizing antibodies (>1.30 log 10) reduced viremia in a dose-dependent manner.

Figure 20:
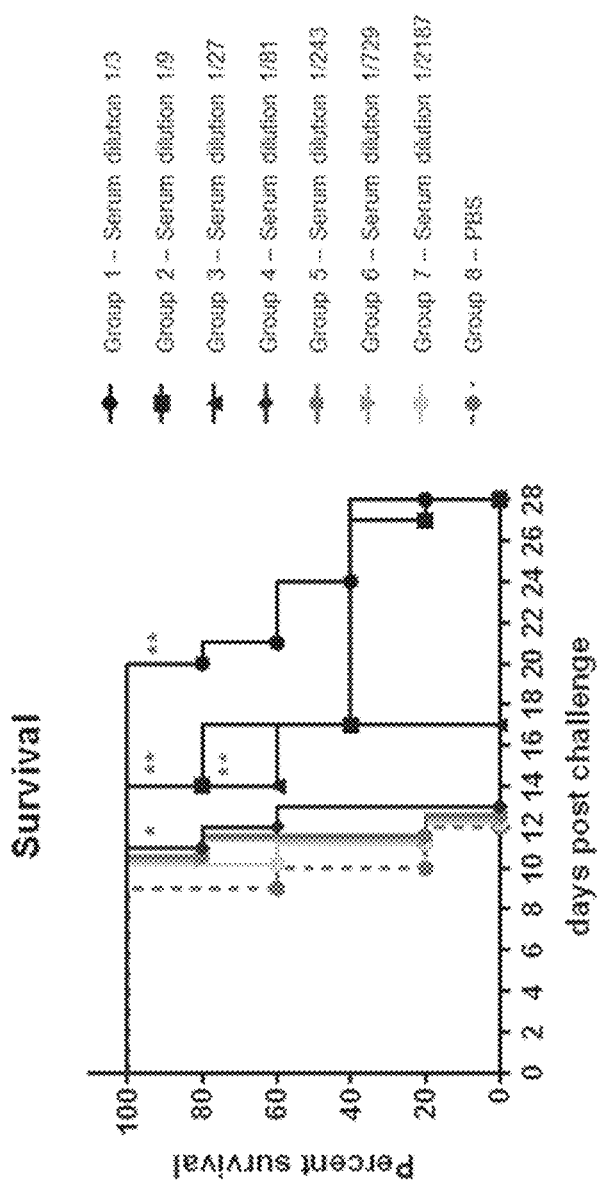
FIG. 20 shows the survival analysis of passive transfer and control mice challenged with Zika virus.

The median survival day of mice in groups 1-8 were: not determined, day 17, day 17, day 13, day 11, day 11, day 11, and day 10, respectively (FIG. 20). Importantly, the survival curves for groups of mice with detectable ZIKV neutralizing antibody titers (groups 1-4) were statistically different compared to the control group (group 8) (p=0.0019, 0.0019, 0.0019, 0.0153, respectively). These results suggested that detectable levels (>1.30 log 10) of ZIKV neutralizing antibodies delayed onset of disease in a dose-dependent manner.

Figure 21:
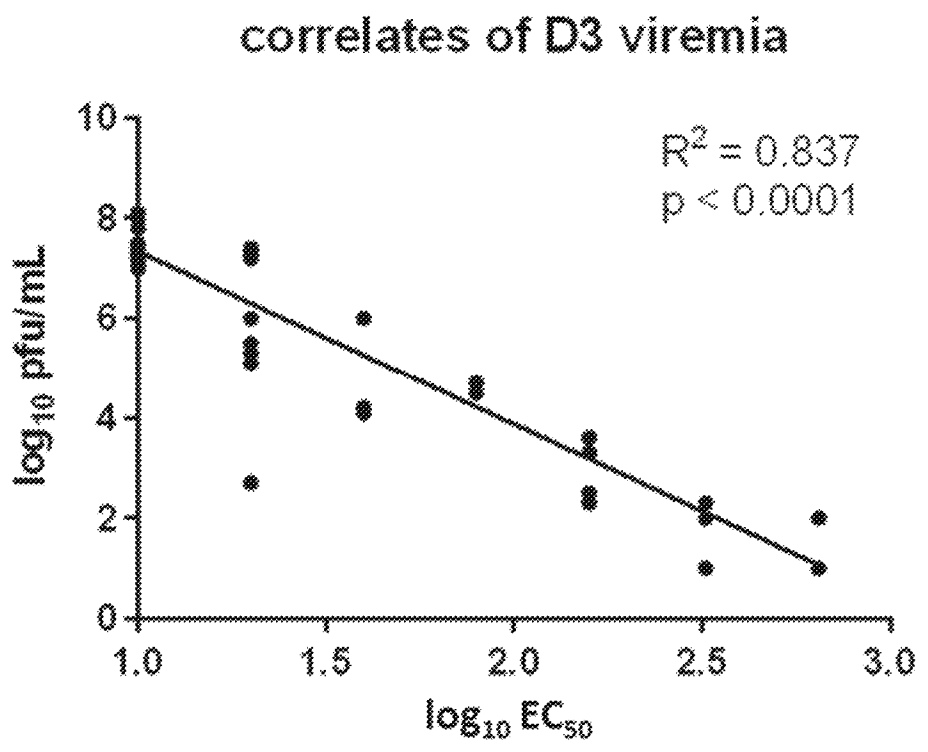

Finally, the ZIKV neutralizing antibody titer of each animal was graphed against its corresponding viremia titer and linear regression analysis was performed. A highly inversely correlated relationship between ZIKV neutralizing antibody titers and viremia levels at day 3 post-challenge was observed (FIG. 21). A summary of the results from the passive transfer studies is shown in Table 12 below.

TABLE 12

Summary of passive transfer results

| Group | Serum dilution | Circulating ZIKV nAb GMT | Viremia (D3) log10 pfu/mL | % survival (D28) | Median survival day |
|---|---|---|---|---|---|
| 1 | 1/3 | 2.69 ± 0.17 | 1.66 ± 0.62 | 20 | 24 |
| 2 | 1/9 | 2.26 ± 0.13 | 2.73 ± 0.68 | 0 | 17 |
| 3 | 127 | 1.72 ± 0.16 | 4.69 ± 0.77 | 0 | 17 |
| 4 | 1/81 | 1.30 ± 0.16 | 4.94 ± 1.29 | 0 | 13 |
| 5 | 1/243 | <1.30 | 7.25 ± 0.10 | 0 | 11 |
| 6 | 1/729 | <1.30 | 7.54 ± 0.31 | 0 | 11 |
| 7 | 1/2187 | <1.30 | 7.52 ± 0.39 | 0 | 11 |
| 8 | PBS | <1.30 | 7.47 ± 0.37 | 0 | 10 |

While no groups of mice receiving ZIKAV neutralizing antibodies were fully protected from lethal ZIKAV challenge in this experiment, reduced viremia levels and delayed onset of disease in a dose-dependent manner among the groups of mice with detectable levels of circulating ZIKAV neutralizing antibody titers was demonstrated.

Taken together, preclinical data from both CD-1 and AG129 mouse studies indicate that a PIZV derived from separate and well-characterized viral clones are immunogenic and able to provide protection against challenge with wild-type ZIKAV. Importantly, a low and high vaccine dose elicited a similar neutralizing antibody response after two doses, and provided similar levels of protection against lethal ZIKAV challenge. Interestingly, mice vaccinated with an unadjuvanted PIZV candidate also showed partial protection from ZIKAV challenge. Vaccine antisera significantly diminished viremia in passively immunized AG129 mice, and prolonged survival against lethal ZIKAV challenge. These results also demonstrate that the well-characterized PIZV candidates were highly efficacious against ZIKAV infection in the highly ZIKAV-susceptible AG129 mouse model.

Additionally, it was found that the sequence of a PRV-ABC59 (from PRVABC59 P6e) at passage 7 was genetically identical to that of passage 6. This was surprising given that flaviviruses are generally regarded as genetically labile. PRVABC59 P6e was selected as the pre-master virus seed due in part to its genetic stability over 7 passages. Without wishing to be bound by theory, it is believed that this enhanced genetic stability may be due to the single amino acid substitution (W98G) in the wing domain of NS1, as this was the only mutation observed in the Vero cell-adapted PRVABC59 P6 genome. Additionally, genetic stability and homogeneity is advantageous in that it reduces variability and increases reproducible production of subsequent strains that may be used for vaccine formulation.

Example 3: Preclinical Assessment of the Phenotype of the P6a and P6e Strains

Materials and Methods

AG129 mice (lacking interferon α/β and γ receptors) are susceptible to ZIKV infection and disease, including severe pathologies in the brain. 14-week-old AG129 mice were intraperitoneally infected with 104 and 103 pfu of the ZIKV passage 6 clones a (P6a) and e (P6e).

Mice were weighed and monitored daily (up to 28 days) for clinical signs of illness (weight loss, ruffled fur, hunched posture, lethargy, limb weakness, partial/full paralysis). Additionally, analysis of viremia was performed by plaque titration of serum samples collected three days post-challenge as described in Example 1.

Results

Figure 22:
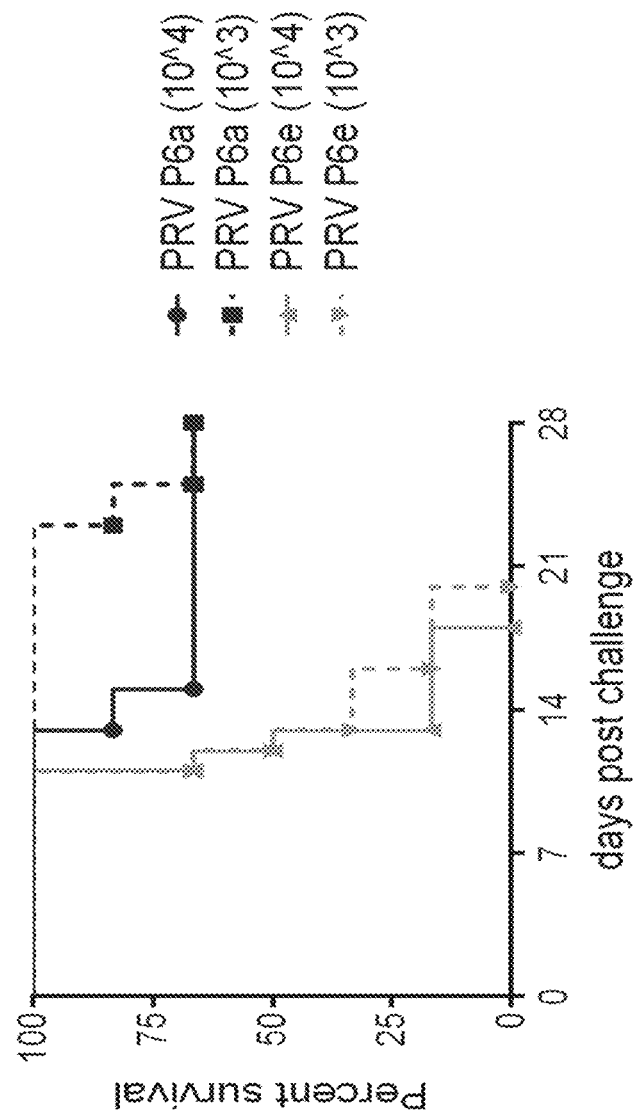
FIG. 22 shows the survival analysis of AG129 mice after infection with Zika virus preMVS stocks of P6a and P6e using a Kaplan Meier survival curve.
Figure 23:
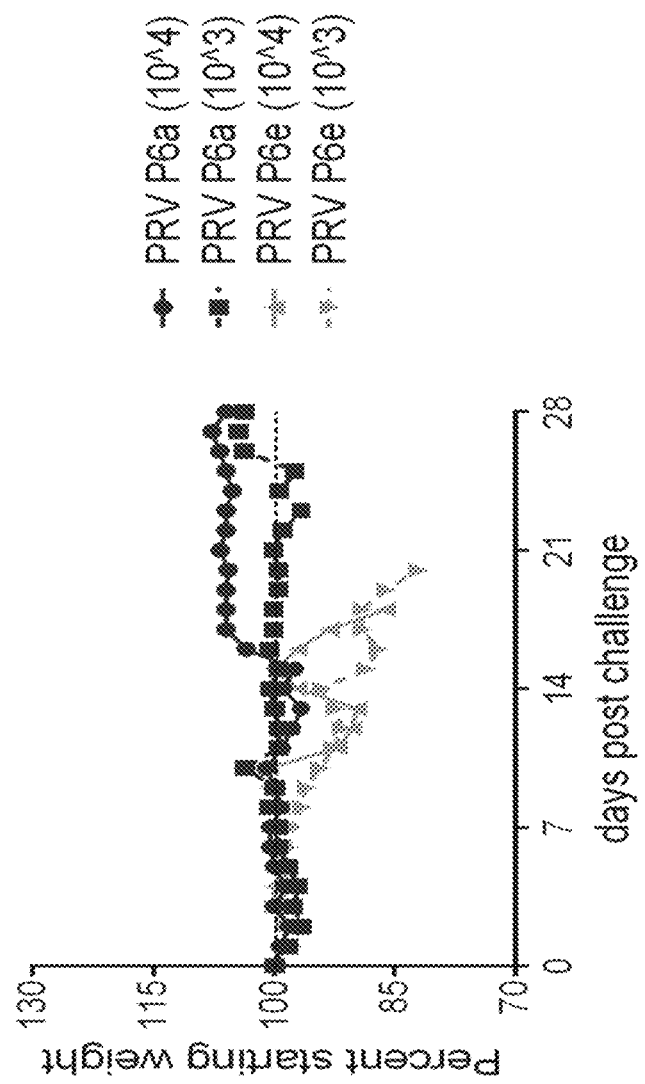
FIG. 23 shows the mean body weight as expressed in percentage of starting weight at time of invention after infection with Zika virus preMVS stocks of P6a and P6e. The dashed line represents 100% of starting weight for reference.
Figure 24:
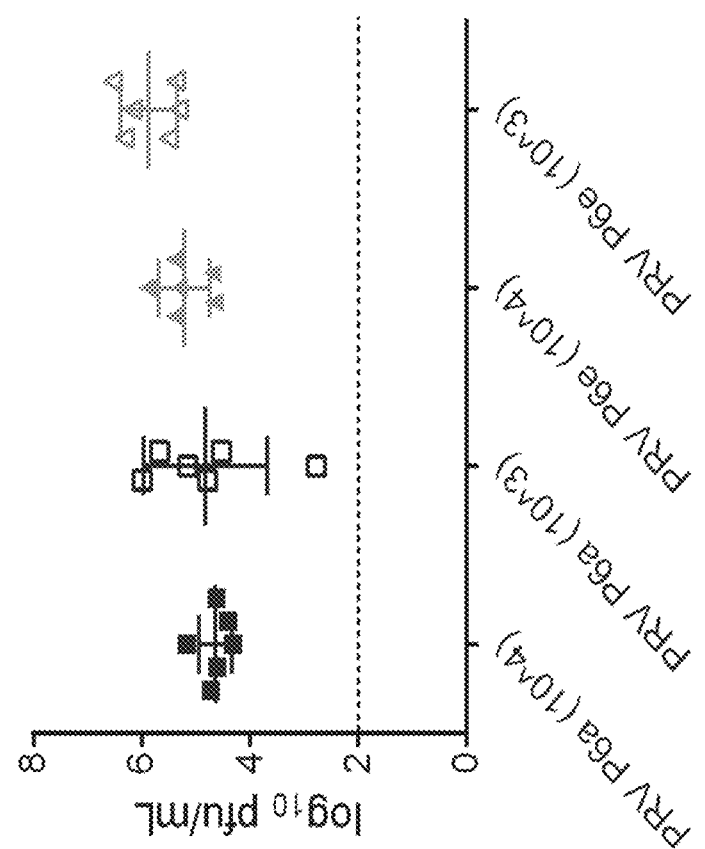
FIG. 24 shows the serum viremia of individual AG129 mice three days post-infection with Zika virus preMVS stocks of P6a and P6e, reported as PFU/mL. The dashed line represents the limit of detection of the assay.

Infection with P6e resulted in 100% mortality (median survival time=12.5 days), while infection with P6a resulted in only 33% mortality (median survival time=undetermined) (FIG. 22). In agreement with this, preMVS P6e infected mice showed greater weight loss as compared to PRVABC59 P6a infected mice (3). No statistical difference was found in mean group viremia levels between groups of mice infected with PRVABC59 P6a or P6e (FIG. 24). These data suggest that growth kinetics alone may not be a key determinant (since both strains produced similar viremia, and similar peak titers in vitro) and that a characteristic of the Envelope protein could be important for virulence (of a wildtype strain) and immunogenicity (of an inactivated candidate).

Example 4: Clinical Immunogenicity and Efficacy of a Purified Inactivated Zika Virus Vaccine (PIZV) Derived from P6e Strains The following example describes a clinical immunogenicity and efficacy study of a purified inactivated Zika virus vaccine (PIZV) in Flavivirus nave patients.

A lot of purified inactivated Zika virus vaccine (PIZV), suitable for use in clinical immunogenicity and efficacy studies, was generated and characterized.

The inactivated Zika virus active agent is no longer able to infect host cells, which can be infected with a Zika virus which has not been inactivated. For example, the inactivated Zika virus is no longer able to infect Vero cells and exert a cytopathic effect on the Vero cells.

The amount of the purified inactivated Zika virus can be determined by a Bradford assay (Bradford et al. (1976) Anal. Biochem. 72: 248-254) using defined amounts of recombinant Zika envelope protein to establish the standard curve.

The purity of the purified Zika virus can be determined by size exclusion chromatography. In the current example, the main peak of the purified Zika virus in the size exclusion chromatography was more than 85% of the total area under the curve in the size exclusion chromatography.

The investigational vaccine (PIZV) refers to Zika purified formalin-inactivated virus formulated with 200 ng aluminum hydroxide, Al(OH)3, as adjuvant, in phosphate buffered saline solution (PBS). The final liquid formulated product is filled into single-use vials and sealed with tamper-evident seals. The investigational vaccine is administered IM (intramuscularly) as a 2-dose regimen of 0.5 mL at 2, 5, or 10 ng antigen per dose, 28 days apart.

Sodium chloride (NaCl) 0.9% solution for injection is being used as placebo. It is supplied in single-use vials. It is a sterile, clear, colorless liquid solution of sodium chloride without preservative designed for parenteral use only. The placebo is administered IM as a 2-dose regimen of 0.5 mL per dose, 28 days apart.

Test Methods

PRNT assay: Neutralizing antibody titers were determined by a plaque reduction neutralization test (PRNT) as described previously (See Protection of Rhesus monkeys against dengue virus challenge after tetravalent live attenuated dengue virus vaccination. J. Infect. Dis. 193, 1658-1665 (2006). Muthumani K, Griffin BD, Agarwal S, et al. In vivo protection against ZIKV infection and pathogenesis through passive antibody transfer and active immunisation with a prMEnv DNA vaccine. NPJ Vaccines 2016; 1: 16021). The Zika strain used for PRNT assay development was PRV-ABC59.

Immuno Outcome Measures:

Definitions

Sero-positivity (PRNT): titers of >LOD (Limit of detection)
Sero-negativity (PRNT): titers of <LOD (Limit of detection)
Seroconversion (PRNT): Post vaccination titers of >LOD in initially seronegative subjects
LOD (PRNT)=10
Assigned value for below LOD=5
LLoQ (Lower Limit of Qualification, PRNT)=26
Assigned value for below LLoQ (Lower Limit of Qualification)=13

Reporter virus particle (RVP) neutralization assay: Neutralizing antibody titers were analyzed by titration of serum samples with a constant amount of Zika RVPs in Vero cells grown in 96-well plates. RVPs contained the prME proteins of Zika (strain SPH2012) and a Dengue-based Renilla luciferase reporter. Briefly, sera were heat inactivated at 56° C. for 30 min, diluted, and then incubated at 37° C. with RVPs. The serum/RVP mixture was then mixed with Vero cells and incubated for 72 hours at 37° C.±2° C./5% CO2 before detection with luciferase substrate. Data was analyzed using JMP11 non-linear 4 parameter analysis, normalized to a positive tracking control and effective dose 50% (EC50) was reported.

Study Description

A Phase 1, Randomized, Observer-Blind, Placebo-Controlled, Safety, Immunogenicity, and Dose Ranging Study of Purified Inactivated Zika Virus Vaccine (PIZV) in Flavivirus Nave and Primed Healthy Adults Aged 18 to 49 Years The study design is shown in FIG. 25. This study was designed to sequentially enroll flavivirus-nave and flavivirus-primed healthy adults between the ages of 18 and 49 years. The two sequential cohorts are each comprised of 120 subjects (planned) randomly allocated to one of 4 groups of 30 subjects, to receive either one of three dosages of the PIZV vaccine or saline placebo. The vaccination regimen consists of 2 doses administered 28 days apart. The data in this example only relates to the Flavivirus nave subjects (n=124), further data with Flavivirus primed subjects are to be expected. This example provides data from a first interim analysis following Day 57 (28 days post-dose 2) for the "flavivirus-nave cohort". Data from the flavivirus-primed cohort are not part of this interim analysis, as recruitment for this group was still ongoing at the time first interim analysis.

In summary, subjects were randomized into four study groups, who received two doses of either placebo (saline) or purified inactivated Zika vaccine (PIZV) with a concentration of 2 µg, 5 µg and 10 µg. The study involved intramuscular injection of the vaccine (or placebo) at day 1 and day 29, with blood samples being taken on day −15, 1, 8, 29, 36, 57, 211, 393, 767 of the study. Blood samples on day −15 were used to determine Flavivirus serostatus screening and eligibility screening. Samples on day 1, 29, 57 were for immunogenicity assessment. Safety lab testing was carried out on days 8 and 36. Persistence of immunity will be assessed on day 211, 393 and 767.

Based on the data from 28 days post dose 2, the purified inactivated Zika virus vaccine (PIZV) was safe and immunogenic in Flavivirus-nave adults aged between 18-49 yrs.

Primary Objectives

The primary objective of the study was to describe the safety of two doses of PIZV given 28 days apart and to select a dose level from three different antigen concentrations (2, 5 or 10 µg) for use in subsequent clinical studies. The primary endpoints were: the percentages of subjects experiencing solicited local and systemic adverse events (AEs) during the 7-day period after administration of each dose of PIZV or placebo, and the percentages of subjects experiencing non-serious unsolicited AEs and serious adverse events (SAES) during the 28-day period after vaccination.

Secondary Objectives

The secondary objectives were to describe the immune response to the purified inactivated Zika virus vaccine (PIZV) at 28 days post dose 1 and 28 days post dose 2 in flavivirus nave adults. The secondary endpoints related to these objectives are geometric mean titers (GMTs) of neutralizing anti-ZIKV antibodies, seropositivity rates (SPR) and seroconversion rates (SCR) at the considered timepoints.

Analysis of the data was performed by a separate set of unblinded statisticians and programmers, who had access to the individual treatment assignments. All personnel involved in the conduct of the trial were blinded to the individual subject treatment assignments. The study team had access to the group level unblinded results only.

Study Population

A total of 124 subjects were enrolled in the flavivirus-nave cohort and included in the Safety Set (SS), comprised of all randomized subjects who have received at least one dose of PIZV or placebo. Among those, 118 (95.2% of the SS) were included in the Full Analysis Set (FAS) of randomized subjects who had received at least one dose of the investigational vaccine (PIZV)/placebo, provided valid serology results at baseline and at least once post-vaccination. One hundred and thirteen (113) subjects (91.1% of the SS) were included in the Per Protocol Set (PPS) of subjects in the FAS who had no major protocol violations relevant for the immunogenicity analysis. The analysis sets are presented in Table 14.

TABLE 14

Analysis sets

| | Number of Subjects (%) | | | | |
|---|---|---|---|---|---|
| | Placebo (N = 30) | 2 μg PIZV (N = 31) | 5 μg PIZV (N = 31) | 10 μg PIZV N = 32 | Total (N = 124) |
| Safety Set (SS) | 30 (100%) | 31 (100%) | 31 (100%) | 32 (100%) | 124 (100%) |
| Full Analysis Set (FAS) | 29 (96.7%) | 28 (90.3%) | 31 (100%) | 30 (93.8%) | 118 (95.2%) |
| Per-Protocol Set (PPS) | 28 (93.3%) | 26 (83.9%) | 29 (93.5%) | 30 (93.8%) | 113 (91.1%) |

Safety Set = all randomized subjects who received at least one (1) dose of PIZV or placebo
Full Analysis Set = all randomized subjects who received at least one dose of PIZV/placebo and provided valid baseline and at least one post-vaccination serology result
Per Protocol Set = all subjects in the FAS who had no major protocol violations Subjects in the SS were 35.3±8.91 years of age (mean±standard deviation), and were distributed as 28.2% in the 18-29 years age-range and 71.8% in the 30-49 years age-range. Women represented 54.8% of the cohort. Study participants were White (81.5%), Black (14.5%), and "Non-Hispanic" (93.5%) regarding race and ethnicity. The mean BMI in the SS was 27.5±4.05 (mean±standard deviation). Demographic characteristics (age, sex, height, weight, BMI and ethnicity) were overall similar across the four study groups. Women were more represented in the placebo group, where they constituted 66% of the study participants, than in the other groups, where gender distribution was more balanced. The demographics and baseline characteristics are presented in Table 15.

Safety laboratory parameters and vital signs were checked at study entry as part of inclusion criteria. These specified that vital signs had to be within normal limits (i.e., below Grade 1 as indicated in the FDA Toxicity Grading Scale) and that safety laboratory tests had to be within normal limits or not be above Grade 1 as defined in the FDA Toxicity Grading Scale.

TABLE 15

Demographic and Baseline Characteristics (Safety Set)

| | Number of Subjects (%) | | | | |
|---|---|---|---|---|---|
| | Placebo (N = 30) | 2 ug (N = 31) | 5 ug (N = 31) | 10 ug (N = 32) | Total (N = 124) |
| Age (Years) | | | | | |
| n | 30 | 31 | 31 | 32 | 124 |
| Mean (SD) | 36.5 (9.00) | 34.9 (9.52) | 35.8 (8.86) | 34.1 (8.50) | 35.3 (8.91) |
| Median | 39.5 | 36.0 | 36.0 | 33.5 | 36.0 |
| Minimum, Maximum | 18, 49 | 18, 48 | 20, 49 | 20, 49 | 18, 49 |
| Age (years) (n [%]) | | | | | |
| 18-29 | 8 (26.7) | 9 (29.0) | 9 (29.0) | 9 (28.1) | 35 (28.2) |
| 30-49 | 22 (73.3) | 22 (71.0) | 22 (71.0) | 23 (71.9) | 89 (71.8) |
| Sex (n [%]) | | | | | |
| Male | 10 (33.3) | 15 (48.4) | 13 (41.9) | 18 (56.3) | 56 (45.2) |
| Female | 20 (66.7) | 16 (51.6) | 18 (58.1) | 14 (43.8) | 68 (54.8) |
| Ethnicity (n [%]) | | | | | |
| Hispanic or Latino | 1 (3.3) | 1 (3.2) | 2 (6.5) | 4 (12.5) | 8 (6.5) |
| Not-Hispanic or Latino | 29 (96.7) | 30 (96.8) | 29 (93.5) | 28 (87.5) | 116 (93.5) |
| Not Reported | 0 | 0 | 0 | 0 | 0 |
| Unknown | 0 | 0 | 0 | 0 | 0 |
| Race (n [%]) | | | | | |
| American Indian or Alaskan Native | 2 (6.7) | 0 | 0 | 0 | 2 (1.6) |
| Asian | 0 | 0 | 0 | 0 | 0 |
| Black or African American | 6 (20.0) | 5 (16.1) | 3 (9.7) | 4 (12.5) | 18 (14.5) |
| Native Hawaiian or Other Pacific Islander | 0 | 0 | 0 | 0 | 0 |
| White | 22 (73.3) | 26 (83.9) | 26 (83.9) | 27 (84.4) | 101 (81.5) |
| Multiracial | 0 | 0 | 2 (6.5) | 1 (3.1) | 3 (2.4) |

TABLE 15-continued

| Demographic and Baseline Characteristics (Safety Set) | | | | | |
|---|---|---|---|---|---|
| | Number of Subjects (%) | | | | |
| | Placebo (N = 30) | 2 ug (N = 31) | 5 ug (N = 31) | 10 ug (N = 32) | Total (N = 124) |
| BMI (kg/m$^2$) | | | | | |
| n | 30 | 31 | 31 | 32 | 124 |
| Mean (SD) | 28.169 (4.0388) | 27.527 (4.7632) | 27.541 (3.7165) | 26.750 (3.6511) | 27.485 (4.0452) |
| Median | 28.861 | 27.900 | 27.831 | 25.965 | 27.607 |
| Minimum, Maximum | 20.86, 34.64 | 20.13, 34.83 | 18.84, 34.14 | 18.80, 34.37 | 18.80, 34.83 |

BMI = Weight (kg)/height$^2$ (m$^2$).
Note 1:
Age is calculated using the Date of Informed Consent.
Note 2:
Subject included in Multiracial Category only if multiple Race categories selected.

Safety/Reactogenicity

The overall reporting incidence of solicited local adverse events (AEs) was higher in the groups that received the vaccine (PIZV) than in the placebo group. Pain was the most frequently reported solicited AE at the injection site. After dose 1, pain was experienced by 30.0% to 38.7% of subjects in the PIZV groups compared to 13.8% in the placebo group. After dose 2, incidences of pain were similar to those following dose 1: 29.6% to 40% in the PIZV groups, and 14.3% in the placebo group. Intensity of pain was reported as mild after dose 1 and mild to moderate after dose 2, with 2 subjects in the 5 ng PIZV group (6.7%) and one subject in the 10 μg PIZV group (3.3%) reporting moderate pain. Other solicited local AEs (erythema, swelling and induration) were reported by not more than 9.7% of the subjects.

The onset of pain occurred on day 1 for 90% of the subjects or day 2 (for 3 subjects). Pain was not reported beyond day 5 by any subject in the placebo or PIZV groups.

Solicited systemic AEs of any nature were reported by 30% to 48.4% of the subjects across the PIZV groups and by 41.4% in the Placebo group after dose 1. After dose 2, incidences were 10% to 33.3% across the PIZV groups and 27.6% in the Placebo group. Overall 81.3% (dose 1) and 75% (dose 2) of the solicited systemic AEs were judged as related to study vaccination. After both doses, the most reported systemic events were headache, fatigue and myalgia.

Most systemic AEs were reported as mild, i.e. not interfering with daily activity. A few occurrences were moderate in intensity:
after dose 1, for 6.7-12.9% of subjects in the PIZV groups and 17.2% of placebo recipients;
after dose 2, for 0-3.3% of subjects across the PIZV groups and 10.3% in the placebo group.

There was a single report of a severe AE: one subject in the placebo group experienced fever. This study participant presented a temperature of 39.4° C., measured orally, 4 days after receiving the second study vaccination. This fever was not judged as study-related by the investigator.

Solicited systemic AEs were variably reported throughout the 7-day period in the four groups. The onset of events for fever, fatigue, arthralgia and myalgia was mainly during the 2 days following vaccination and was variable for headache and malaise. Fever was reported during the 2 days following vaccination, except for the subject reporting severe fever in the placebo group on day 4.

The incidence of solicited local and systemic adverse events 7 days after vaccination are shown in Table 16.

TABLE 16

| Incidence of solicited local and systemic adverse events 7 days after vaccination (Safety set) | | | | | | | | |
|---|---|---|---|---|---|---|---|---|
| | Dose 1 | | | | Dose 2 | | | |
| | Placebo (N = 30) | 2 μg PIZV (N = 31) | 5 μg PIZV (N = 31) | 10 μg PIZV (N = 32) | Placebo (N = 30) | 2 μg PIZV (N = 31) | 5 μg PIZV (N = 31) | 10 μg PIZV (N = 32) |
| Local AEs n (%) | | | | | | | | |
| Any | 4 (13.8) | 9 (30.0) | 12 (38.7) | 13 (41.9) | 5 (17.9) | 8 (29.6) | 11 (36.7) | 12 (40.0) |
| Pain | 4 (13.8) | 9 (30.0) | 10 (32.3) | 12 (38.7) | 4 (14.3) | 8 (29.6) | 11 (36.7) | 12 (40.0) |
| Erythema | 0 | 0 | 0 | 1 (3.2) | 1 (3.6) | 0 | 1 (3.3) | 1 (3.3) |
| Swelling | 0 | 0 | 0 | 0 | 0 | 0 | 2 (6.7) | 0 |
| Induration | 0 | 0 | 3 (9.7) | 2 (6.5) | 0 | 0 | 1 (3.3) | 0 |
| Systemic AEs n (%) | | | | | | | | |
| Any | 12 (41.4) | 9 (30.0) | 12 (38.7) | 15 (48.4) | 8 (27.6) | 9 (33.3) | 3 (10.0) | 8 (26.7) |
| Fever | 1 (3.4) | 0 | 0 | 1 (3.2) | 2 (7.1) | 0 | 0 | 0 |
| Headache | 9 (31.0) | 5 (16.7) | 8 (25.8) | 4 (12.9) | 3 (10.3) | 4 (14.8) | 1 (3.3) | 6 (20.0) |
| Fatigue | 6 (20.7) | 7 (23.3) | 6 (19.4) | 10 (32.3) | 6 (20.7) | 3 (11.1) | 2 (6.7) | 5 (16.7) |
| Arthralgia | 1 (3.4) | 1 (3.3) | 1 (3.2) | 3 (9.7) | 1 (3.4) | 2 (7.4) | 0 | 1 (3.3) |
| Myalgia | 3 (10.3) | 3 (10.0) | 5 (16.1) | 4 (12.9) | 2 (6.9) | 2 (7.4) | 1 (3.3) | 2 (6.7) |
| Malaise | 4 (13.8) | 2 (6.7) | 2 (6.5) | 4 (12.9) | 2 (6.9) | 0 | 0 | 3 (10.0) |

N = number of subjects with information available; n (%) = number (percentage) of subjects reporting a specific AE.

In total 30.6% of the subjects reported unsolicited AEs (not including prolonged solicited AEs) in the 28 days following any dose: 21.9-38.7% in the PIZV groups and 36.7% in the placebo group. These AEs were mainly infections, infestations (13.7%) and nervous system disorders (3.2%: headache, migraine, dizziness). All were mild to moderate in intensity.

Unsolicited AEs were considered as related to the study vaccination for three subjects (2.4%). The events reported were:

at post dose 1, dizziness for one subject in the 5 ng PIZV group and flushing for one subject in the 2 ng PIZV group;

at post dose 2, eye pruritus and lacrimation increased for one subject in the 10 ng PIZV group.

These were mild to moderate in intensity, started on day 1 or 2 after vaccination, had a duration of 1 to 3 days and were all resolved.

One subject discontinued with the study vaccination due to a headache after dose 1. This subject received PIZV and experienced the headache 1 day after vaccination. The headache was resolved 36 days after its onset. No serious adverse event (SAE) was reported during the period from dose 1 up to 28 days post dose 2.

The few changes from the baseline observed for blood safety laboratory parameters in the 7 days following vaccination, e.g. from normal to mild or from mild to moderate AEs, occurred in comparable percentages of subjects across the four groups. Urinalysis parameters were either normal at all time-points or the grading category was similar across groups and visits.

Immunogenicity

Table 17 presents the geometric antibody titers of Zika virus neutralizing antibodies (EC50) as measured by PRNT as well as seropositivity rates and seroconversion rates after each vaccine dose.

The PIZV vaccine was immunogenic in flavivirus-naïve adults. All subjects were seronegative at baseline. Vaccination of subjects initially seronegative for antibodies against Zika virus elicited seropositivity in all subjects after two doses of PIZV vaccine of any dosage: seroconversion rates ranged from 69.23% to 96.43% post-dose 1 and were 100% post-dose 2. All subjects in the placebo group remained seronegative throughout the period considered.

A dose-ranging effect was observed on seropositivity rates post-dose 1 and on GMTs after each dose. After the first dose, almost all subjects (96.4%) who had received the 10 ng PIZV dose had mounted neutralizing antibodies against the Zika virus. The second dose led to a more than 10-fold increase in GMT from dose 1, in the three PIZV groups.

TABLE 17

Seropositivity, seroconversion rates and GMTs of Zika virus neutralizing antibodies ($EC_{50}$) (PRNT) before and 28 days after administration of each dose of PIZV (Per Protocol Set)

| | | Placebo (N = 28) | 2 µg PIZV (N = 26) | 5 µg PIZV (N = 29) | 10 µg PIZV (N = 30) |
|---|---|---|---|---|---|
| Sero-positivity rate (95% CI) | Pre-dose 1 | 0 | 0 | 0 | 0 |
| | Post-dose 1 | 0 | 69.23 (48.21, 85.67) | 82.14 (63.11, 93.94) | 96.43 (81.65, 99.91) |
| | Post-dose 2 | 0 | 100 (85.75, 100.00) | 100 (87.66, 100.00) | 100 (87.66, 100.00) |
| Sero-conversion rate (95% CI) | Post-dose 1 | 0 | 69.23 (48.21, 85.67) | 82.14 (63.11, 93.94) | 96.43 (81.65, 99.91) |
| | Post-dose 2 | 0 | 100 (85.75, 100.00) | 100 (87.66, 100.00) | 100 (87.66, 100.00) |
| GMTs (95% CI) | Pre-dose 1 | 5.00 | 5.00 | 5.00 | 5.00 |
| | Post-dose 1 | 5.00 | 38.06 (17.53, 82.66) | 93.76 (44.34, 198.30) | 291.41 (161.74, 525.06) |
| | Post-dose 2 | 5.00 | 1100.75 (741.07, 1635.00) | 1992.33 (1401.28, 2832.70) | 3689.89 (2676.75, 5086.49) |

N = number of subjects in the PPS with PRNT data available;
Seropositivity is defined as titer ≥10; Seroconversion is defined as: seronegative subjects at baseline (titer <10) have titer ≥10 post-vaccination; Results <10 are assigned a titer of 5; Titers ≥10 (limit of detection) and <26 (lower limit of quantification) are assigned a value of 13.

Figure 26:
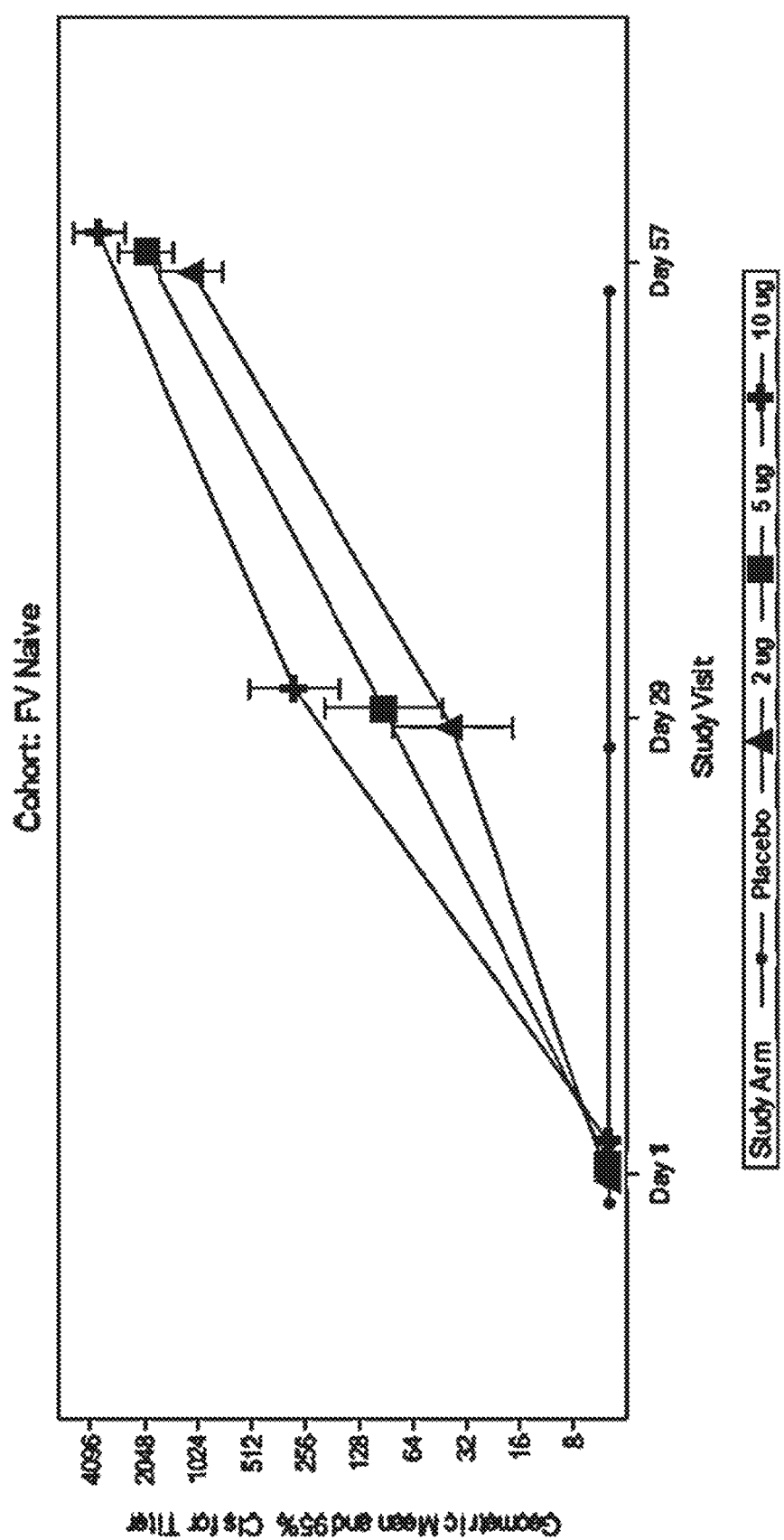
FIG. 26 shows the Geometric Mean Titers (GMTs) determined using PRNT of the Subjects in Example 4
Figure 27:
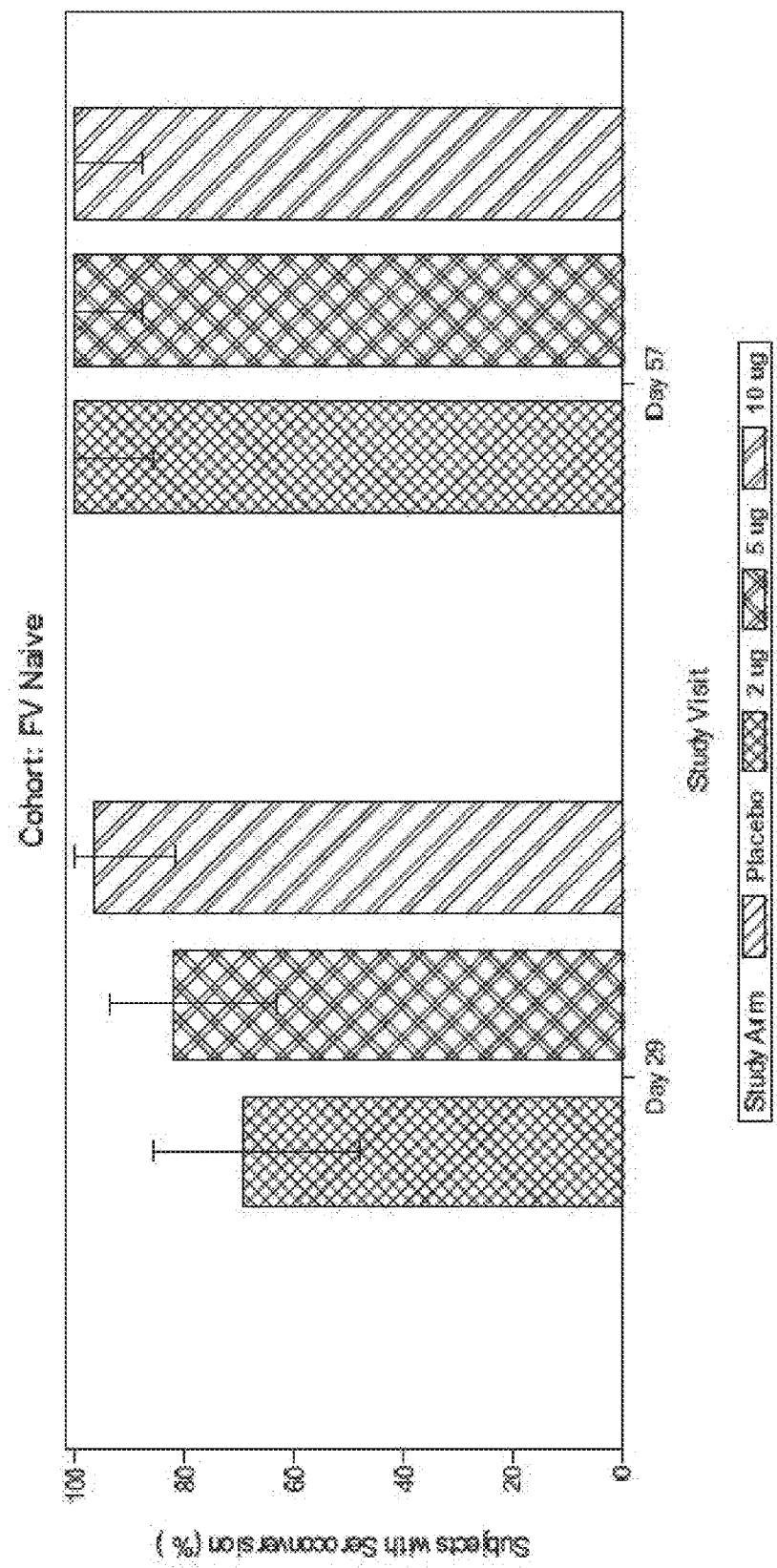
FIG. 27 shows the percentage of subjects achieving seroconversion determined using PRNT at Day 29 (day 28 after prime dose) and Day 57 (28 days after boost dose) of the study described in Example 4.

The Geometric mean titers determined using PRNT, according to table 17, are shown graphically in FIG. 26. The percentage of subjects achieving seroconversion determine using PRNT according to table 17, are shown graphically in FIG. 27.

Figure 28:
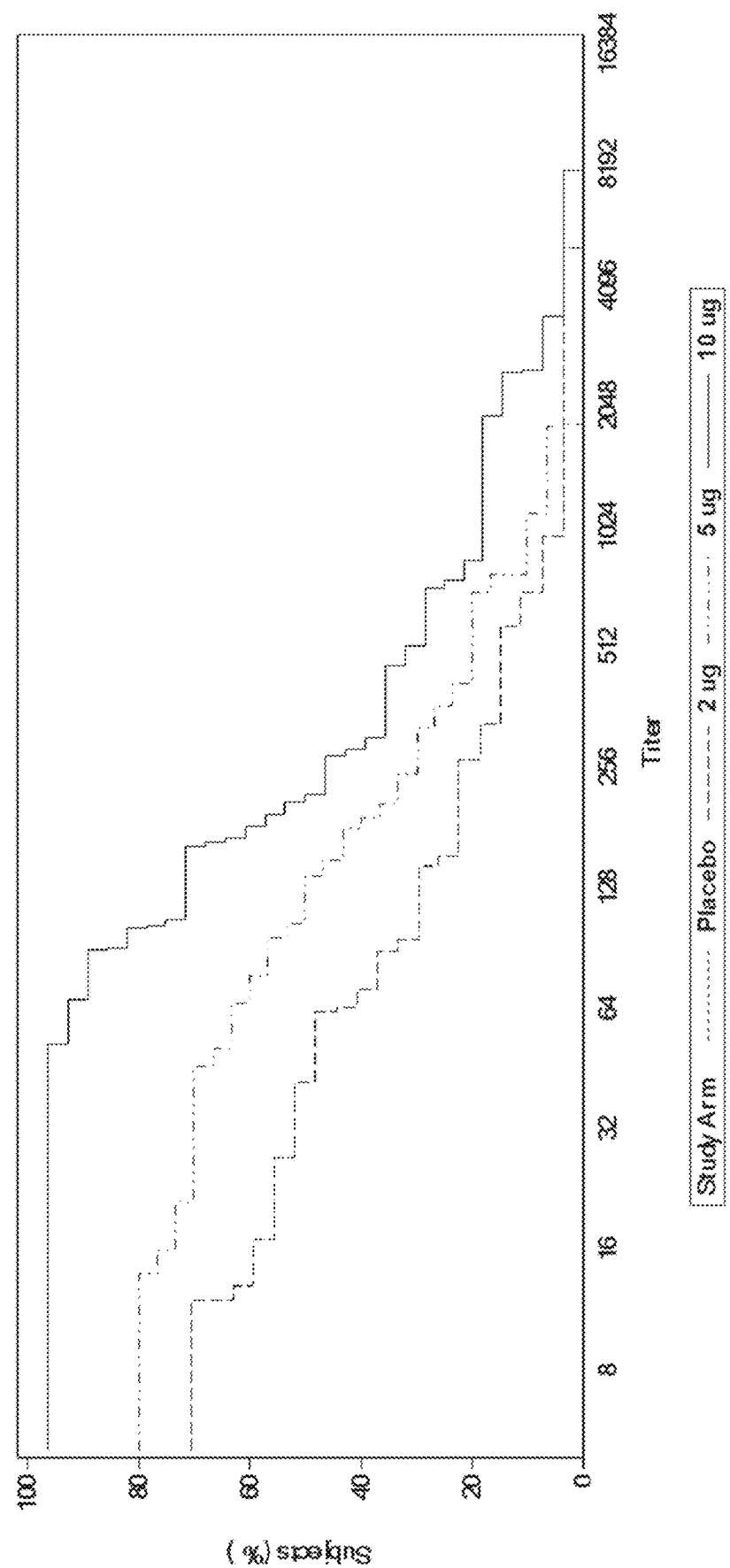
FIG. 28 shows the plot of the percentage of subjects achieving a particular Geometric Mean Titer (determined using PRNT) on day 29 (day 28 after prime dose) of the study described in Example 4.
Figure 29:
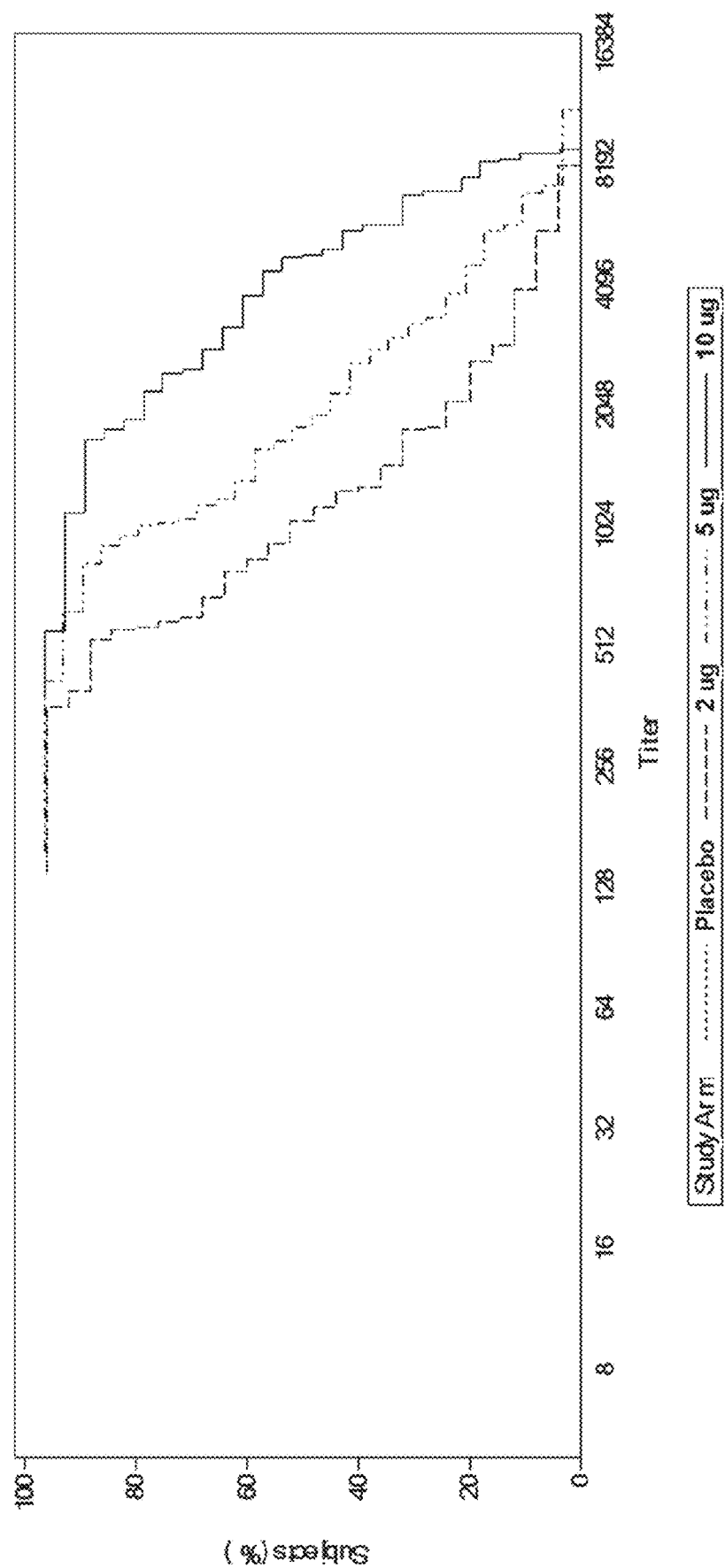
FIG. 29 shows the plot of the percentage of subjects achieving a particular Geometric Mean Titer (determined using PRNT) on day 57 (day 56 after prime dose) of the study described in Example 4.

The distribution of neutralization titers, after dose 1 and after dose 2, are shown in reverse cumulative distribution curves in FIGS. 28 and 29 respectively.

In addition to measuring immune response with the PRNT assay, the samples were also tested with the RVP neutralization assay. Table 18 presents the geometric antibody titers of Zika virus neutralizing antibodies (EC50) as measured by the RVP assay. The RVP assay results show a similar dose-ranging effect of the PRNT data, with gradually higher GMTs with increasing PIZV doses.

TABLE 18

| | | Placebo (N = 27) | 2 µg PIZV (N = 26) | 5 µg PIZV (N = 28) | 10 µg PIZV (N = 30) |
|---|---|---|---|---|---|
| | Pre-dose 1 | 34 (27, 43) | 34 (26, 44) | 32 (27, 39) | 46 (39, 53) |
| GMTs | Post-dose 1 | 28 (22, 36) | 360 (242, 536) | 656 (442, 972) | 1310 (875, 1961) |
| (95% CI) | Post-dose 2 | 31 (25, 40) | 3148 (1988, 4986) | 6212 (4126, 9354) | 13604 (9560, 19359) |

GMTs of Zika virus neutralizing antibodies ($EC_{50}$) (RVP) before and 28 days after vaccination (Per Protocol Set)

N = number of subjects in the PPS with RVP data available.

CONCLUSION

The PIZV vaccine was well tolerated and safe for all antigen doses evaluated in the flavivirus-nave cohort. Solicited systemic AEs were reported in all groups with no apparent increase with increasing dose strength and intensity was mild to moderate. Local solicited AEs reported were also mild to moderate in intensity across the groups. Unsolicited symptoms were reported with similar frequencies in the four study groups. Overall, the vaccine was immunogenic in flavivirus-naïve subjects and a positive dose-ranging response was observed.

What is claimed is:

1. An immunogenic composition comprising a Zika virus having a tryptophan to glycine mutation at position 98 (Trp98Gly) of SEQ ID NO: 1, or at a position corresponding to position 98 of SEQ ID NO: 1, wherein the Zika virus is an inactivated whole virus.

2. The immunogenic composition of claim 1, wherein the Zika virus comprises an envelope protein (Env) having an amino acid sequence that has at least 85%, at least 90%, at least 95%, at least 96%, at least 97%, at least 98%, at least 99%, or 100% sequence identity with the amino acid sequence encoded by the corresponding sequence in SEQ ID NO: 2.

3. The immunogenic composition of claim 1, wherein the sequence encoding the envelope protein (Env) is the same as the corresponding sequence in SEQ ID NO: 2.

4. The immunogenic composition of claim 1, wherein the Zika virus comprises a genomic sequence characterized by SEQ ID NO: 2, encoding a glycine at nucleotide position 292 of the NS1 gene.

5. The immunogenic composition of claim 1, wherein the Zika virus was chemically inactivated with formaldehyde.

6. The immunogenic composition of claim 1, further comprising an adjuvant.

7. The immunogenic composition of claim 6, wherein the adjuvant is an aluminum salt.

8. The immunogenic composition of claim 7, wherein the adjuvant is aluminum hydroxide.

9. A method for inducing an immune response against Zika virus in a subject in need thereof, comprising administering to the subject an immunogenic amount of the or immunogenic composition of claim 1.

10. The method of claim 9, wherein the immunogenic composition is administered as a first (prime) and a second (boost) administration.

11. The method of claim 9, wherein the administration of the immunogenic composition induces the generation of neutralizing antibodies to Zika virus in the subject.

* * * * *

SEQUENCE LISTING

<160> NUMBER OF SEQ ID NOS: 27

<210> SEQ ID NO 1
<211> LENGTH: 351
<212> TYPE: PRT
<213> ORGANISM: Zika virus

<400> SEQUENCE: 1

```
Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
            20                  25                  30

Lys Tyr His Pro Asp Ser Pro Arg Arg Leu Ala Ala Ala Val Lys Gln
        35                  40                  45

Ala Trp Glu Asp Gly Ile Cys Gly Ile Ser Ser Val Ser Arg Met Glu
    50                  55                  60

Asn Ile Met Trp Arg Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
        115                 120                 125

Thr Asn Asn Ser Phe Val Val Asp Gly Asp Thr Leu Lys Glu Cys Pro
    130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Lys Glu
            180                 185                 190

Ala Val His Ser Asp Leu Gly Tyr Trp Ile Glu Ser Glu Lys Asn Asp
        195                 200                 205

Thr Trp Arg Leu Lys Arg Ala His Leu Ile Glu Met Lys Thr Cys Glu
    210                 215                 220

Trp Pro Lys Ser His Thr Leu Trp Thr Asp Gly Ile Glu Glu Ser Asp
225                 230                 235                 240
```

```
Leu Ile Ile Pro Lys Ser Leu Ala Gly Pro Leu Ser His His Asn Thr
                245                 250                 255

Arg Glu Gly Tyr Arg Thr Gln Met Lys Gly Pro Trp His Ser Glu Glu
            260                 265                 270

Leu Glu Ile Arg Phe Glu Glu Cys Pro Gly Thr Lys Val His Val Glu
        275                 280                 285

Glu Thr Cys Gly Thr Arg Gly Pro Ser Leu Arg Ser Thr Thr Ala Ser
    290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr
            340                 345                 350

<210> SEQ ID NO 2
<211> LENGTH: 10675
<212> TYPE: DNA
<213> ORGANISM: Zika virus

<400> SEQUENCE: 2
gttgttgatc tgtgtgaatc agactgcgac agttcgagtt tgaagcgaaa gctagcaaca      60
gtatcaacag gttttatttt ggatttggaa acgagagttt ctggtcatga aaaacccaaa     120
aaagaaatcc ggaggattcc ggattgtcaa tatgctaaaa cgcggagtag cccgtgtgag     180
cccctttggg ggcttgaaga ggctgccagc cggacttctg ctgggtcatg ggcccatcag     240
gatggtcttg gcgattctag ccttttttgag attcacggca atcaagccat cactgggtct     300
catcaataga tggggttcag tggggaaaaa agaggctatg gaaacaataa agaagttcaa     360
gaaagatctg gctgccatgc tgagaataat caatgctagg aaggagaaga agagacgagg     420
cgcagatact agtgtcggaa ttgttggcct cctgctgacc acagctatgg cagcggaggt     480
cactagacgt gggagtgcat actatatgta cttggacaga aacgatgctg gggaggccat     540
atcttttcca accacattgg ggatgaataa gtgttatata cagatcatgg atcttggaca     600
catgtgtgat gccaccatga gctatgaatg ccctatgctg gatgaggggg tggaaccaga     660
tgacgtcgat tgttggtgca acacgacgtc aacttgggtt gtgtacggaa cctgccatca     720
caaaaaaggt gaagcacgga gatctagaag agctgtgacg ctcccctccc attccaccag     780
gaagctgcaa acgcggtcgc aaacctggtt ggaatcaaga gaatacacaa agcacttgat     840
tagagtcgaa aattggatat tcaggaaccc tggcttcgcg ttagcagcag ctgccatcgc     900
ttggcttttg ggaagctcaa cgagccaaaa agtcatatac ttggtcatga tactgctgat     960
tgccccggca tacagcatca ggtgcatagg agtcagcaat agggactttg tggaaggtat    1020
gtcaggtggg acttgggttg atgttgtctt ggaacatgga ggttgtgtca ccgtaatggc    1080
acaggacaaa ccgactgtcg acatagagct ggttacaaca acagtcagca acatggcgga    1140
ggtaagatcc tactgctatg aggcatcaat atcagacatg gcttctgaca gccgctgccc    1200
aacacaaggt gaagcctacc ttgacaagca atcagacact caatatgtct gcaaaagaac    1260
gttagtggac agaggctggg gaaatggatg tggacttttt ggcaaaggga gcctggtgac    1320
atgcgctaag tttgcatgct ccaagaaaat gaccgggaag agcatccagc cagagaatct    1380
ggagtaccgg ataatgctgt cagttcatgg ctcccagcac agtgggatga tcgttaatga    1440
cacaggacat gaaactgatg agaatagagc gaaagttgag ataacgccca attcaccgag    1500
```

```
agccgaagcc accctggggg gttttggaag cctaggactt gattgtgaac cgaggacagg   1560
ccttgacttt tcagatttgt attacttgac tatgaataac aagcactggt tggttcacaa   1620
ggagtggttc cacgacattc cattaccttg gcacgctggg gcagacaccg gaactccaca   1680
ctggaacaac aaagaagcac tggtagagtt caaggacgca catgccaaaa ggcaaactgt   1740
cgtggttcta gggagtcaag aaggagcagt tcacacggcc cttgctggag ctctggaggc   1800
tgagatggat ggtgcaaagg gaaggctgtc ctctggccac ttgaaatgtc gcctgaaaat   1860
ggataaactt agattgaagg gcgtgtcata ctccttgtgt actgcagcgt tcacattcac   1920
caagatcccg gctgaaacac tgcacgggac agtcacagtg gaggtacagt acgcagggac   1980
agatggacct tgcaaggttc cagctcagat ggcggtggac atgcaaactc tgaccccagt   2040
tgggaggttg ataaccgcta accccgtaat cactgaaagc actgagaact ctaagatgat   2100
gctggaactt gatccaccat ttggggactc ttacattgtc ataggagtcg gggagaagaa   2160
gatcacccac cactggcaca ggagtggcag caccattgga aaagcatttg aagccactgt   2220
gagaggtgcc aagagaatgg cagtcttggg agacacagcc tggactttg gatcagttgg    2280 aggcgctctc aactcattgg gcaagggcat ccatcaaatt tttggagcag ctttcaaatc   2340 attgttttgga ggaatgtcct ggttctcaca aattctcatt ggaacgttgc tgatgtggtt   2400
gggtctgaac acaaagaatg gatctatttc ccttatgtgc ttggccttag ggggagtgtt   2460
gatcttctta tccacagccg tctctgctga tgtggggtgc tcggtggact ctcaaagaa    2520 ggagacgaga tgcggtacag gggtgttcgt ctataacgac gttgaagcct ggagggacag   2580
gtacaagtac catcctgact cccccgtag attggcagca gcagtcaagc aagcctggga    2640
agatggtatc tgcgggatct cctctgtttc aagaatggaa acatcatgt ggagatcagt    2700 agaagggag ctcaacgcaa tcctggaaga gaatggagtt caactgacgg tcgttgtggg   2760
atctgtaaaa aaccccatgt ggagaggtcc acagagattg cccgtgcctg tgaacgagct   2820
gccccacggc tggaaggctt gggggaaatc gtatttcgtc agagcagcaa agacaaataa   2880
cagctttgtc gtggatggtg acacactgaa ggaatgccca ctcaaacata gagcatggaa   2940
cagctttctt gtggaggatc atgggttcgg ggtatttcac actagtgtct ggctcaaggt   3000
tagagaagat tattcattag agtgtgatcc agccgttatt ggaacagctg ttaagggaaa   3060
ggaggctgta cacagtgatc taggctactg gattgagagt gagaagaatg acacatggag   3120
gctgaagagg gcccatctga tcgagatgaa acatgtgaa tggccaaagt cccacacatt    3180
gtggacagat ggaatagaag agagtgatct gatcatacc aagtctttag ctgggccact    3240
cagccatcac aataccagag agggctacag gacccaaatg aaagggccat ggcacagtga   3300
agagcttgaa attcggtttg aggaatgcc aggcactaag gtccacgtgg aggaaacatg    3360
tggaacaaga ggaccatctc tgagatcaac cactgcaagc ggaagggtga tcgaggaatg   3420
gtgctgcagg gagtgcacaa tgcccccact gtcgttccgg gctaaagatg gctgttggta   3480
tggaatggag ataaggccca ggaaagaacc agaaagcaac ttagtaaggt caatggtgac   3540
tgcaggatca actgatcaca tggaccactt ctcccttgga gtgcttgtga tcctgctcat   3600
ggtgcaggaa gggctgaaga agagaatgac cacaaagatc atcataagca catcaatggc   3660
agtgctggta gctatgatcc tgggaggatt ttcaatgagt gacctggcta agcttgcaat   3720
tttgatgggt gccaccttcg cggaaatgaa cactggagga gatgtagctc atctggcgct   3780
gatagcggca ttcaaagtca gaccagcgtt gctggtatct ttcatcttca gagctaattg   3840 gacacccgt gaaagcatgc tgctggcctt ggcctcgtgt ctttttgcaaa ctgcgatctc   3900
```

```
cgccttggaa ggcgacctga tggttctcat caatggtttt gctttggcct ggttggcaat    3960
acgagcgatg gttgttccac gcactgataa catcaccttg gcaatcctgg ctgctctgac    4020
accactggcc cggggcacac tgcttgtggc gtggagagca ggccttgcta cttgcggggg    4080
gtttatgctc ctctctctga agggaaaagg cagtgtgaag aagaacttac catttgtcat    4140
ggccctggga ctaaccgctg tgaggctggt cgaccccatc aacgtggtgg gactgctgtt    4200
gctcacaagg agtgggaagc ggagctggcc ccctagcgaa gtactcacag ctgttggcct    4260
gatatgcgca ttggctggag ggttcgccaa ggcagatata gagatggctg gcccatggc    4320 cgcggtcggt ctgctaattg tcagttacgt ggtctcagga aagagtgtgg acatgtacat    4380
tgaaagagca ggtgacatca catgggaaaa agatgcggaa gtcactggaa acagtccccg    4440
gctcgatgtg gcgctagatg agagtggtga tttctccctg gtggaggatg acggtccccc    4500
catgagagag atcatactca aggtggtcct gatgaccatc tgtggcatga acccaatagc    4560 cataccctt gcagctggag cgtggtacgt atacgtgaag actggaaaaa ggagtggtgc    4620
tctatgggat gtgcctgctc ccaaggaagt aaaaaagggg gagaccacag atggagtgta    4680
cagagtaatg actcgtagac tgctaggttc aacacaagtt ggagtgggag ttatgcaaga    4740
gggggtcttt cacactatgt ggcacgtcac aaaaggatcc gcgctgagaa gcggtgaagg    4800
gagacttgat ccatactggg gagatgtcaa gcaggatctg gtgtcatact gtggtccatg    4860
gaagctagat gccgcctggg atgggcacag cgaggtgcag ctcttggccg tgcccccgg    4920 agagagagcg aggaacatcc agactctgcc cggaatattt aagacaaagg atggggacat    4980
tggagcggtt gcgctggatt acccagcagg aacttcagga tctccaatcc tagacaagtg    5040
tgggagagtg ataggacttt atggcaatgg ggtcgtgatc aaaaacggga gttatgttag    5100
tgccatcacc caagggagga gggaggaaga gactcctgtt gagtgcttcg agccctcgat    5160
gctgaagaag aagcagctaa ctgtcttaga cttgcatcct ggagctggga aaaccaggag    5220
agttcttcct gaaatagtcc gtgaagccat aaaaacaaga ctccgtactg tgatcttagc    5280
tccaaccagg gttgtcgctg ctgaaatgga ggaggccctt agagggcttc cagtgcgtta    5340
tatgacaaca gcagtcaatg tcacccactc tggaacagaa atcgtcgact taatgtgcca    5400
tgccaccttc acttcacgtc tactacagcc aatcagagtc cccaactata atctgtatat    5460
tatggatgag gcccacttca cagatcctc aagtatagca gcaagaggat acatttcaac    5520
aagggttgag atgggcgagg cggctgccat cttcatgacc gccacgccac caggaaccg    5580 tgacgcattt ccggactcca actcaccaat tatggacacc gaagtggaag tcccagagag    5640
agcctggagc tcaggctttg attgggtgac ggatcattct ggaaaaacag tttggtttgt    5700
tccaagcgtg aggaacggca atgagatcgc agcttgtctg acaaaggctg aaaacgggt    5760 catacagctc agcagaaaga cttttgagac agagttccag aaaacaaaac atcaagagtg    5820
ggactttgtc gtgacaactg acatttcaga gatgggcgcc aactttaaag ctgaccgtgt    5880
catagattcc aggagatgcc taaagccggt catacttgat ggcgagagag tcattctggc    5940
tggacccatg cctgtcacac atgccagcgc tgcccagagg aggggcgca taggcaggaa    6000 tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
gcttaggacg gagcaaagga agaccttgt ggaactcatg aaaagaggag atcttcctgt    6240
```

```
ttggctggcc tatcaggttg catctgccgg aataacctac acagatagaa gatggtgctt    6300
tgatggcacg accaacaaca ccataatgga agacagtgtg ccggcagagg tgtggaccag    6360
acacggagag aaaagagtgc tcaaaccgag gtggatggac gccagagttt gttcagatca    6420
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg gagaccctag agaccataat gcttttgggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt tcctattgct ggtggtgctc atacctgagc cagaaaagca    6840
aagatctccc caggacaacc aaatggcaat catcatcatg gtagcagtag gtcttctggg    6900
cttgattacc gccaatgaac tcggatggtt ggagagaaca aagagtgacc taagccatct    6960
aatgggaagg agagaggagg gggcaaccat aggattctca atggacattg acctgcggcc    7020
agcctcagct tgggccatct atgctgcctt gacaactttc attaccccag ccgtccaaca    7080
tgcagtgacc acctcataca acaactactc cttaatggcg atgccacgc aagctggagt    7140 gttgtttggc atgggcaaag ggatgccatt ctacgcatgg gactttggag tcccgctgct    7200
aatgataggt tgctactcac aattaacacc cctgaccctta atagtggcca tcattttgct    7260
cgtggcgcac tacatgtact tgatcccagg gctgcaggca gcagctgcgc gtgctgccca    7320 gaaagagaacg gcagctggca tcatgaagaa ccctgttgtg gatggaatag tggtgactga    7380
cattgacaca atgacaattg accccccaagt ggagaaaaag atgggacagg tgctactcat    7440
agcagtagcc gtctccagcg ccatactgtc gcggaccgcc tgggggtggg gggaggctgg    7500
ggctctgatc acagccgcaa cttccacttt gtgggaaggc tctccgaaca agtactggaa    7560
ctcctctaca gccacttcac tgtgtaacat ttttaggggga agttacttgg ctggagcttc    7620
tctaatctac acagtaacaa gaaacgctgg cttggtcaag agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg gcaacgggag ccatgctgt gtcccgagga agtgcaaagc tgagatggtt    7860
ggtggagcgg ggatacctgc agccctatgg aaaggtcatt gatcttggat gtggcagagg    7920
gggctggagt tactacgtcg ccaccatccg caaagttcaa gaagtgaaag gatacacaaa    7980
aggaggccct ggtcatgaag aacccgtgtt ggtgcaaagc tatgggtgga acatagtccg    8040
tcttaagagt ggggtggacg tctttcatat ggcggctgag ccgtgtgaca cgttgctgtg    8100
tgacataggt gagtcatcat ctagtcctga agtggaagaa gcacggacgc tcagagtcct    8160
ctccatggtg ggggattggc ttgaaaaaag accaggagcc ttttgtataa aagtgttgtg    8220
cccatacacc agcactatga tggaaaccct ggagcgactg cagcgtaggt atgggggagg    8280
actggtcaga gtgccactct cccgcaactc tacacatgag atgtactggg tctctggagc    8340
gaaaagcaac accataaaaa gtgtgtccac cacgagccag ctcctcttgg ggcgcatgga    8400
cgggcctagg aggccagtga aatatgagga ggatgtgaat ctcggctctg gcacgcgggc    8460
tgtggtaagc tgcgctgaag ctcccaacat gaagatcatt ggtaaccgca ttgaaaggat    8520
ccgcagtgag cacgcggaaa cgtggttctt tgacgagaac cacccatata ggacatgggc    8580
ttaccatgga agctatgagg cccccacaca agggtcagcg tcctctctaa taaacgggt    8640
```

-continued

```
tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760 agaccccaa gaaggcactc gtcaggttat gagcatggtc tcttcctggt tgtggaaaga     8820
gctaggcaaa cacaaacggc cacgagtctg caccaaagaa gagttcatca acaaggttcg    8880
tagcaatgca gcattagggg caatatttga agaggaaaaa gagtggaaga ctgcagtgga    8940
agctgtgaac gatccaaggt tctgggctct agtggacaag gaaagagagc accacctgag    9000
aggagagtgc cagagctgtg tgtacaacat gatgggaaaa agagaaaaga aacaagggga    9060
atttggaaag gccaagggca gccgcgccat ctggtatatg tggctagggg ctagatttct    9120
agagttcgaa gcccttggat tcttgaacga ggatcactgg atggggagag agaactcagg    9180
aggtggtgtt gaagggctgg gattacaaag actcggatat gtcctagaag agatgagtcg    9240
tataccagga ggaaggatgt atgcagatga cactgctggc tgggacaccc gcattagcag    9300
gtttgatctg gagaatgaag ctctaatcac caaccaaatg gagaaagggc acagggcctt    9360
ggcattggcc ataatcaagt acacatacca aaacaaagtg gtaaaggtcc ttagaccagc    9420
tgaaaaaggg aaaacagtta tggacattat ttcgagacaa gaccaaaggg ggagcggaca    9480
agttgtcact tacgctctta acacatttac caacctagtg gtgcaactca ttcggaatat    9540
ggaggctgag gaagttctag agatgcaaga cttgtggctg ctgcggaggt cagagaaagt    9600
gaccaactgg ttgcagagca acggatggga taggctcaaa cgaatggcag tcagtggaga    9660
tgattgcgtt gtgaagccaa ttgatgatag gtttgcacat gccctcaggt tcttgaatga    9720
tatgggaaaa gttaggaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc aaatgtggca    9960 gctccttat ttccacagaa gggacctccg actgatggcc aatgccattt gttcatctgt    10020
gccagttgac tgggttccaa ctgggagaac tacctggtca atccatggaa agggagaatg    10080
gatgaccact gaagacatgc ttgtggtgtg aacagagtg tggattgagg agaacgacca    10140
catggaagac aagaccccag ttacgaaatg gacagacatt ccctatttgg gaaaagggga    10200
agacttgtgg tgtggatctc tcataggca cagaccgcgc accacctggg ctgagaacat    10260
taaaaacaca gtcaacatgg tgcgcaggat cataggtgat gaagaaaagt acatggacta    10320
cctatccacc caagttcgct acttgggtga agaagggtct acacctggag tgctgtaagc    10380
accaatctta atgttgtcag gcctgctagt cagccacagc ttggggaaag ctgtgcagcc    10440 tgtgacccccc caggagaag ctgggaaacc aagcctatag tcaggccgag aacgccatgg    10500
cacggaagaa gccatgctgc ctgtgagccc ctcagaggac actgagtcaa aaaaccccac    10560
gcgcttggag gcgcaggatg ggaaaagaag gtggcgacct tccccaccct tcaatctggg    10620
gcctgaactg gagatcagct gtggatctcc agaagaggga ctagtggtta gagga        10675
```

<210> SEQ ID NO 3
<211> LENGTH: 20
<212> TYPE: DNA
<213> ORGANISM: artificial
<220> FEATURE:
<223> OTHER INFORMATION: oligo 1 (CpG 1826)

<400> SEQUENCE: 3

```
tccatgacgt tcctgacgtt                                                    20

<210> SEQ ID NO 4
<211> LENGTH: 18
<212> TYPE: DNA
<213> ORGANISM: artificial
<220> FEATURE:
<223> OTHER INFORMATION: oligo 2 (CpG 1758)

<400> SEQUENCE: 4
tctcccagcg tgcgccat                                                      18

<210> SEQ ID NO 5
<211> LENGTH: 30
<212> TYPE: DNA
<213> ORGANISM: artificial
<220> FEATURE:
<223> OTHER INFORMATION: oligo 3

<400> SEQUENCE: 5
accgatgacg tcgccggtga cggcaccacg                                         30

<210> SEQ ID NO 6
<211> LENGTH: 24
<212> TYPE: DNA
<213> ORGANISM: artificial
<220> FEATURE:
<223> OTHER INFORMATION: oligo 4 (CpG 2006)

<400> SEQUENCE: 6
tcgtcgtttt gtcgttttgt cgtt                                               24

<210> SEQ ID NO 7
<211> LENGTH: 20
<212> TYPE: DNA
<213> ORGANISM: artificial
<220> FEATURE:
<223> OTHER INFORMATION: oligo 5 (CpG 1668)

<400> SEQUENCE: 7
tccatgacgt tcctgatgct                                                    20

<210> SEQ ID NO 8
<211> LENGTH: 31
<212> TYPE: PRT
<213> ORGANISM: Zika virus

<400> SEQUENCE: 8

Phe Thr Lys Ile Pro Ala Glu Thr Leu His Gly Thr Val Thr Val Glu
1               5                   10                  15

Val Gln Tyr Ala Gly Thr Asp Gly Pro Cys Lys Val Pro Ala Gln
            20                  25                  30

<210> SEQ ID NO 9
<211> LENGTH: 31
<212> TYPE: PRT
<213> ORGANISM: Zika virus

<400> SEQUENCE: 9

Phe Thr Lys Ile Pro Ala Glu Thr Leu His Gly Thr Val Thr Val Glu
1               5                   10                  15

Val Gln Tyr Ala Gly Thr Asp Gly Pro Cys Lys Val Pro Ala Gln
            20                  25                  30
```

```
<210> SEQ ID NO 10
<211> LENGTH: 31
<212> TYPE: PRT
<213> ORGANISM: West Nile Virus

<400> SEQUENCE: 10

Phe Leu Gly Thr Pro Ala Asp Thr Gly His Gly Thr Val Val Leu Glu
1               5                   10                  15

Leu Gln Tyr Thr Gly Thr Asp Gly Pro Cys Lys Val Pro Ile Ser
            20                  25                  30

<210> SEQ ID NO 11
<211> LENGTH: 31
<212> TYPE: PRT
<213> ORGANISM: Japanese Encephalitis Virus

<400> SEQUENCE: 11

Phe Ala Lys Asn Pro Ala Asp Thr Gly His Gly Thr Val Val Ile Glu
1               5                   10                  15

Leu Thr Tyr Ser Gly Ser Asp Gly Pro Cys Lys Ile Pro Ile Val
            20                  25                  30

<210> SEQ ID NO 12
<211> LENGTH: 31
<212> TYPE: PRT
<213> ORGANISM: Saint Louis Encephalitis Virus

<400> SEQUENCE: 12

Phe Ser Lys Asn Pro Ala Asp Thr Gly His Gly Thr Val Ile Val Glu
1               5                   10                  15

Leu Gln Tyr Thr Gly Ser Asn Gly Pro Cys Arg Val Pro Ile Ser
            20                  25                  30

<210> SEQ ID NO 13
<211> LENGTH: 30
<212> TYPE: PRT
<213> ORGANISM: Yellow Fever Virus

<400> SEQUENCE: 13

Phe Val Lys Asn Pro Thr Asp Thr Gly His Gly Thr Val Val Met Gln
1               5                   10                  15

Val Lys Val Ser Lys Gly Ala Pro Cys Arg Ile Pro Val Ile
            20                  25                  30

<210> SEQ ID NO 14
<211> LENGTH: 31
<212> TYPE: PRT
<213> ORGANISM: Dengue virus

<400> SEQUENCE: 14

Leu Glu Lys Glu Val Ala Glu Thr Gln His Gly Thr Val Leu Val Gln
1               5                   10                  15

Val Lys Tyr Glu Gly Thr Asp Ala Pro Cys Lys Ile Pro Phe Ser
            20                  25                  30

<210> SEQ ID NO 15
<211> LENGTH: 31
<212> TYPE: PRT
<213> ORGANISM: Dengue virus

<400> SEQUENCE: 15

Val Val Lys Glu Ile Ala Glu Thr Gln His Gly Thr Ile Val Ile Arg
1               5                   10                  15
```

```
Val Gln Tyr Glu Gly Asp Gly Ser Pro Cys Lys Ile Pro Phe Glu
            20                  25                  30

<210> SEQ ID NO 16
<211> LENGTH: 31
<212> TYPE: PRT
<213> ORGANISM: Dengue virus

<400> SEQUENCE: 16

Leu Lys Lys Glu Val Ser Glu Thr Gln His Gly Thr Ile Leu Ile Lys
1               5                   10                  15

Val Glu Tyr Lys Gly Glu Asp Ala Pro Cys Lys Ile Pro Phe Ser
            20                  25                  30

<210> SEQ ID NO 17
<211> LENGTH: 31
<212> TYPE: PRT
<213> ORGANISM: Dengue virus

<400> SEQUENCE: 17

Ile Asp Lys Glu Met Ala Glu Thr Gln His Gly Thr Thr Val Val Lys
1               5                   10                  15

Val Lys Tyr Glu Gly Ala Gly Ala Pro Cys Lys Val Pro Ile Glu
            20                  25                  30

<210> SEQ ID NO 18
<211> LENGTH: 29
<212> TYPE: PRT
<213> ORGANISM: Zika virus

<400> SEQUENCE: 18

Ser Val Lys Asn Pro Met Gly Arg Gly Pro Gln Arg Leu Pro Val Pro
1               5                   10                  15

Val Asn Glu Leu Pro His Gly Trp Lys Ala Trp Gly Lys
            20                  25

<210> SEQ ID NO 19
<211> LENGTH: 29
<212> TYPE: PRT
<213> ORGANISM: Zika virus

<400> SEQUENCE: 19

Ser Val Lys Asn Pro Met Trp Arg Gly Pro Gln Arg Leu Pro Val Pro
1               5                   10                  15

Val Asn Glu Leu Pro His Gly Trp Lys Ala Trp Gly Lys
            20                  25

<210> SEQ ID NO 20
<211> LENGTH: 29
<212> TYPE: PRT
<213> ORGANISM: West Nile Virus

<400> SEQUENCE: 20

Lys Gln Glu Gly Met Tyr Lys Ser Ala Pro Lys Arg Leu Thr Ala Thr
1               5                   10                  15

Thr Glu Lys Leu Glu Ile Gly Trp Lys Ala Trp Gly Lys
            20                  25

<210> SEQ ID NO 21
<211> LENGTH: 29
<212> TYPE: PRT
<213> ORGANISM: Japanese Encephalitis Virus
```

-continued

<400> SEQUENCE: 21

Lys Pro Val Gly Arg Tyr Arg Ser Ala Pro Lys Arg Leu Ser Met Thr
1               5                   10                  15

Gln Glu Lys Phe Glu Met Gly Trp Lys Ala Trp Gly Lys
            20                  25

<210> SEQ ID NO 22
<211> LENGTH: 29
<212> TYPE: PRT
<213> ORGANISM: Saint Louis Encephalitis Virus

<400> SEQUENCE: 22

Glu Asp Pro Lys Tyr Tyr Lys Arg Ala Pro Arg Arg Leu Lys Lys Leu
1               5                   10                  15

Glu Asp Glu Leu Asn Tyr Gly Trp Lys Ala Trp Gly Lys
            20                  25

<210> SEQ ID NO 23
<211> LENGTH: 29
<212> TYPE: PRT
<213> ORGANISM: Yellow Fever Virus

<400> SEQUENCE: 23

```
Asp Pro Lys Asn Val Tyr Gln Arg Gly Thr His Pro Phe Ser Arg Ile
1               5                   10                  15

Arg Asp Gly Leu Gln Tyr Gly Trp Lys Thr Trp Gly Lys
            20                  25
```

<210> SEQ ID NO 24
<211> LENGTH: 29
<212> TYPE: PRT
<213> ORGANISM: Dengue virus

<400> SEQUENCE: 24

```
Asp Val Ser Gly Ile Leu Ala Gln Gly Lys Lys Met Ile Arg Pro Gln
1               5                   10                  15

Pro Met Glu His Lys Tyr Ser Trp Lys Ser Trp Gly Lys
            20                  25
```

<210> SEQ ID NO 25
<211> LENGTH: 29
<212> TYPE: PRT
<213> ORGANISM: Dengue virus

<400> SEQUENCE: 25

```
Asp Ile Lys Gly Ile Met Gln Ala Gly Lys Arg Ser Leu Arg Pro Gln
1               5                   10                  15

Pro Thr Glu Leu Lys Tyr Ser Trp Lys Thr Trp Gly Lys
            20                  25
```

<210> SEQ ID NO 26
<211> LENGTH: 29
<212> TYPE: PRT
<213> ORGANISM: Dengue virus

<400> SEQUENCE: 26

```
Asp Ile Thr Gly Val Leu Glu Gln Gly Lys Arg Thr Leu Thr Pro Gln
1               5                   10                  15

Pro Met Glu Leu Lys Tyr Ser Trp Lys Thr Trp Gly Lys
            20                  25
```

```
<210> SEQ ID NO 27
<211> LENGTH: 29
<212> TYPE: PRT
<213> ORGANISM: Dengue virus

<400> SEQUENCE: 27

Asp Val Lys Gly Val Leu Thr Lys Gly Lys Arg Ala Leu Thr Pro Pro
1               5                   10                  15

Val Asn Asp Leu Lys Tyr Ser Trp Lys Thr Trp Gly Lys
            20                  25
```